(12) United States Patent
Yao et al.

(10) Patent No.: US 11,560,427 B2
(45) Date of Patent: Jan. 24, 2023

(54) HEAVY-CHAIN ANTIBODIES (VHHS) AGAINST CLAUDIN 18A2 AND USE THEREOF

(71) Applicant: ZHEJIANG DOER BIOLOGICS CORPORATION, Hangzhou (CN)

(72) Inventors: Gaofeng Yao, Hangzhou (CN); Yali Lu, Hangzhou (CN); Zhenxing Zhou, Hangzhou (CN); Yilin Fang, Hangzhou (CN); Li'na Zhu, Hangzhou (CN); Changkui Li, Hangzhou (CN); Hongta Zhang, Hangzhou (CN); Xiaofang Wen, Hangzhou (CN); Jiali Dong, Hangzhou (CN); Yanshan Huang, Hangzhou (CN)

(73) Assignee: ZHEJIANG DOER BIOLOGICS CO., LTD., Hangzhou (CN)

( * ) Notice: Subject to any disclaimer, the term of this patent is extended or adjusted under 35 U.S.C. 154(b) by 0 days.

(21) Appl. No.: 17/422,204

(22) PCT Filed: Dec. 6, 2019

(86) PCT No.: PCT/CN2019/123537
§ 371 (c)(1),
(2) Date: Jan. 12, 2022

(87) PCT Pub. No.: WO2020/147451
PCT Pub. Date: Jul. 23, 2020

(65) Prior Publication Data
US 2022/0259303 A1 Aug. 18, 2022

(30) Foreign Application Priority Data
Jan. 15, 2019 (CN) .......................... 201910033995.4

(51) Int. Cl.
*C07K 16/28* (2006.01)
*A61K 47/68* (2017.01)
*A61P 35/00* (2006.01)
*A61K 35/17* (2015.01)
*C12N 5/0783* (2010.01)
*C12N 15/62* (2006.01)
*A61K 39/00* (2006.01)

(52) U.S. Cl.
CPC .............. *C07K 16/28* (2013.01); *A61K 35/17* (2013.01); *A61K 47/68* (2017.08); *A61P 35/00* (2018.01); *C12N 5/0636* (2013.01); *C12N 15/62* (2013.01); *A61K 2039/505* (2013.01)

(58) Field of Classification Search
None
See application file for complete search history.

(56) References Cited

FOREIGN PATENT DOCUMENTS

| CN | 107667118 | 2/2018 | |
|---|---|---|---|
| CN | 107960056 | 4/2018 | |
| CN | 108047331 | 5/2018 | |
| WO | WO-2018102795 A2 * | 6/2018 | ............ A61K 35/17 |

* cited by examiner

*Primary Examiner* — Peter J Reddig

(57) ABSTRACT

The present disclosure relates to the field of biology, in particular, to an anti-CLD18A2 VHH. The present disclosure provides an anti-CLD18A2 VHH. A complementarity determining region (CDR) of the anti-CLD18A2 VHH includes CDR1-CDR3 having amino acid sequences as shown below: CDR1 having an amino acid sequence represented by one of SEQ ID NO. 4-11, CDR2 having an amino acid sequence represented by one of SEQ ID NO. 19-26, and CDR3 having an amino acid sequence represented by one of SEQ ID NO.33-39. The anti-CLD18A2 VHH of the present disclosure can specifically bind to the epitope on CLD18A2, and the corresponding fusion protein thereof has good specificity and affinity for CLD18A2, and has a noticeable tumor suppression effect.

20 Claims, 5 Drawing Sheets
Specification includes a Sequence Listing.

HEAVY-CHAIN ANTIBODIES (VHHS) AGAINST CLAUDIN 18A2 AND USE THEREOF

The content of the following submission on ASCII text file is incorporated herein by reference in its entirety: a computer readable form (CRF) of the Sequence Listing (file name: 210042_ST25.txt, date recorded: Dec. 29, 2021, size: 153 KB).

TECHNICAL FIELD

The present disclosure relates to the field of biology, in particular, to an anti-CLD18A2 VHH and use thereof.

BACKGROUND

A claudin 18 (CLD18) is a transmembrane protein with a molecular weight of about 28 kiloDalton (kD), located in the tight junction of epithelium and endothelium, and tightly connected between adjacent cells. Claudins on cell surfaces of normal epithelial tissues can hardly be contacted due to the dense intercellular space. However, the space between tumor cells is relatively sparse. Therefore, claudins on tumor cells become a potential target for extracellular antibodies and immunotherapy. CLD18 has four hydrophobic regions, which serve as transmembrane regions to form two extracellular domains, in which a hydrophobic region 1 and a hydrophobic region 2 form a circular extracellular domain 1, and a hydrophobic region 3 and a hydrophobic region 4 form a circular extracellular domain 2. Due to different gene splicing, CLD18 can turn into two kinds of spliced bodies: CLD18A1 and CLD18A2. CLD18A1 is expressed in the normal lung, while CLD18A2 is only expressed in gastric cells. More importantly, CLD18A2 is only present in differentiated short-lived gastric epithelial cells, but not in gastric stem cells (Niimi T et al. Biol. 2001; 21(21):7380-7390.). These characteristics show that CLD18A2 is a clinically valuable therapeutic target for the treatment of gastric cancer and other CLD18A2 positive tumors.

Successful application of monoclonal antibodies in cancer detection and biologically targeted therapy has caused a revolution in tumor therapy. However, traditional monoclonal antibodies with an excessively large molecular weight (about 150 kD) can hardly penetrate tissues, resulting in low effective concentration in the tumor area and insufficient therapeutic effect. Traditional antibodies have a high risk of immunogenicity, but once they are humanized, it is difficult for the modified antibodies to retain the affinity of the parent antibodies. In addition, many factors, such as a long development period, high production cost, and low stability, limited the application and popularization of fully humanized traditional antibodies in clinical practice. Heavy-chain antibodies (VHHs) that recently emerged include the smallest functional antigen-binding fragments derived from heavy-chain antibodies in adult camels, with high stability and high affinity for antigen binding. Compared with conventional antibodies, VHHs have many unique properties: 1) The sequence encoding of VHHs has high homology with human VH families 3 and 4, making them weak in immunogenicity; 2) VHH has a small molecular weight, only about 15 kDa, and the simple structure of the VHH makes it easy to be massively expressed in microorganisms and easy to be purified; 3) VHHs can recognize a large number of epitopes, including some epitopes that are hidden in molecular clefts; 4) Due to their small molecular weight, VHHs can easily penetrate tissue and reach positions that are difficult to reach by conventional antibodies; 5) VHHs have high solubility and stability under denaturing or high-temperature environments. The unique properties and low cost of VHHs have greatly expanded their application range. Therefore, VHHs have great value in the treatment and diagnosis of diseases and also have excellent development prospects in the antibody-targeted diagnosis and treatment of tumors.

However, there is no specific VHH targeting the epitope of CLD18A2 at present. Therefore, it is of great value to develop new VHHs with high specificities and potency against CLD18A2.

SUMMARY

The present disclosure provides an anti-CLD18A2 VHH for solving the problems.

The present disclosure provides an anti-CLD18A2 VHH. A complementarity determining region (CDR) of the anti-CLD18A2 VHH includes CDR1-CDR3 having amino acid sequences as shown below: CDR1 having an amino acid sequence represented by one of SEQ ID NO. 4-11, CDR2 having an amino acid sequence represented by one of SEQ ID NO. 19-26, and CDR3 having an amino acid sequence represented by one of SEQ ID NO.33-39.

In some embodiments of the present disclosure, the complementarit determining region CDR of the anti-CLD18A2 VHH includes CDR1-CDR3 having amino acid sequences as shown below:

(1) CDR1 having an amino acid sequence represented by SEQ ID NO. 4, CDR2 having an amino acid sequence represented by SEQ ID NO. 19, and CDR3 having an amino acid sequence represented by SEQ ID NO. 33; or (2) CDR1 having an amino acid sequence represented by SEQ ID NO. 5, CDR2 having an amino acid sequence represented by SEQ ID NO. 20, and CDR3 having an amino acid sequence represented by SEQ ID NO. 34; or (3) CDR1 having an amino acid sequence represented by SEQ ID NO. 6, CDR2 having an amino acid sequence represented by SEQ ID NO. 21, and CDR3 having an amino acid sequence represented by SEQ ID NO. 35; or (4) CDR1 having an amino acid sequence represented by SEQ ID NO. 7, CDR2 having an amino acid sequence represented by SEQ ID NO. 22, and CDR3 having an amino acid sequence represented by SEQ ID NO. 36; or (5) CDR1 having an amino acid sequence represented by SEQ ID NO. 8, CDR2 having an amino acid sequence represented by SEQ ID NO. 23, and CDR3 having an amino acid sequence represented by SEQ ID NO. 37; or (6) CDR1 having an amino acid sequence represented by SEQ ID NO. 9, CDR2 having an amino acid sequence represented by SEQ ID NO. 24, and CDR3 having an amino acid sequence represented by SEQ ID NO. 38; or (7) CDR1 having an amino acid sequence represented by SEQ ID NO. 10, CDR2 having an amino acid sequence represented by SEQ ID NO. 25, and CDR3 having an amino acid sequence represented by SEQ ID NO. 36; or (8) CDR1 having an amino acid sequence represented by SEQ ID NO. 11, CDR2 having an amino acid sequence represented by SEQ ID NO. 26, and CDR3 having an amino acid sequence represented by SEQ ID NO. 39.

In some embodiments of the present disclosure, the anti-CLD18A2 VHH includes a frame region FR, which includes FR1-FR4 having amino acid sequences as shown below:

(1) FR1 having an amino acid sequence represented by SEQ ID NO. 1, FR2 having an amino acid sequence represented by SEQ ID NO. 12, FR3 having an amino acid sequence represented by SEQ ID NO. 27, and FR4 having an amino acid sequence represented by SEQ ID NO. 40; or (2) FR1 having an amino acid sequence represented by SEQ ID NO. 2, FR2 having an amino acid sequence represented by SEQ ID NO. 13, FR3 having an amino acid sequence represented by SEQ ID NO. 28, and FR4 having an amino acid sequence represented by SEQ ID NO. 41; or (3) FR1 having an amino acid sequence represented by SEQ ID NO. 3, FR2 having an amino acid sequence represented by SEQ ID NO. 14, FR3 having an amino acid sequence represented by SEQ ID NO. 29, and FR4 having an amino acid sequence represented by SEQ ID NO. 41; or (4) FR1 having an amino acid sequence represented by SEQ ID NO. 1, FR2 having an amino acid sequence represented by SEQ ID NO. 15, FR3 having an amino acid sequence represented by SEQ ID NO. 30, and FR4 having an amino acid sequence represented by SEQ ID NO. 41; or (5) FR1 having an amino acid sequence represented by SEQ ID NO. 2, FR2 having an amino acid sequence represented by SEQ ID NO. 16, FR3 having an amino acid sequence represented by SEQ ID NO. 31, and FR4 having an amino acid sequence represented by SEQ ID NO. 41; or (6) FR1 having an amino acid sequence represented by SEQ ID NO. 2, FR2 having an amino acid sequence represented by SEQ ID NO. 13, FR3 having an amino acid sequence represented by SEQ ID NO. 31, and FR4 having an amino acid sequence represented by SEQ ID NO. 41; or (7) FR1 having an amino acid sequence represented by SEQ ID NO. 1, FR2 having an amino acid sequence represented by SEQ ID NO. 17, FR3 having an amino acid sequence represented by SEQ ID NO. 30, and FR4 having an amino acid sequence represented by SEQ ID NO. 41; or (8) FR1 having an amino acid sequence represented by SEQ ID NO. 2, FR2 having an amino acid sequence represented by SEQ ID NO. 18, FR3 having an amino acid sequence represented by SEQ ID NO. 32, and FR4 having an amino acid sequence represented by SEQ ID NO. 41.

In some embodiments of the present disclosure, the amino acid sequence of the anti-CLD18A2 VHH includes:

a) an amino acid sequence represented by one of SEQ ID NO. 42-49; or b) an amino acid sequence with at least 80% sequence identity with one of SEQ ID NO. 42-49 and has the function of the amino acid sequence defined in a).

In some embodiments of the present disclosure, the anti-CLD18A2 VHH is a humanized antibody. Preferably, the amino acid sequence of the anti-CLD18A2 VHH is represented by one of SEQ ID NO. 67-90.

Another aspect of the present disclosure provides a fusion protein of an anti-CLD18A2 VHH, including a first domain, and a second domain for prolonging the half-life of the VHH in vivo and/or having a binding effect on effector cells.

In some embodiments of the present disclosure, the second domain includes one or more of a serum albumin fragment, polyethylene glycol fragment, and HSA-binding VHH.

In some embodiments of the present disclosure, the second domain includes an immunoglobulin Fc region, preferably selected from a human immunoglobulin Fc region.

In some embodiments of the present disclosure, the human immunoglobulin Fc region includes a mutation for altering an Fc-mediated effector function, and the effector function includes one or more of CDC activity, ADCC activity, and ADCP activity.

In some embodiments of the present disclosure, the immunoglobulin is selected from one or more of IgG, IgA1, IgA2, IgD, IgE, and IgM, and the IgG is selected from one or more of IgG1, IgG2, IgG3, and IgG4 subtypes.

In some embodiments of the present disclosure, the amino acid sequence of the immunoglobulin Fc region is selected from one of SEQ ID NO. 91-95.

In some embodiments of the present disclosure, the second domain includes a molecule that has an affinity for the CD3 receptor present on T cells and/or is capable of binding to the CD3 receptor present on T cells.

In some embodiments of the present disclosure, a connecting peptide is provided between the first domain and the second domain.

In some embodiments of the present disclosure, the connecting peptide is selected from a flexible polypeptide chain composed of alanine and/or serine and/or glycine, and the length of the connecting peptide is 3-40 amino acids.

Another aspect of the present disclosure provides an isolated polynucleotide, which encodes the VHH or the fusion protein.

Another aspect of the present disclosure provides an expression vector, which includes the isolated polynucleotide.

Another aspect of the present disclosure provides an antibody expression system, which includes the expression vector or incorporates the exogenous polynucleotide in the genome.

Another aspect of the present disclosure provides a method for preparing the VHH or the fusion protein, including the following steps: culturing the antibody expression system under conditions suitable for expressing the antibody, thereby expressing the antibody, and purifying and isolating the antibody.

Another aspect of the present disclosure provides an immunoconjugate, which includes the VHH or the fusion protein.

In some embodiments of the present disclosure, the immunoconjugate further includes a coupling portion, and the coupling portion includes one or more of a detectable label, a cytotoxin, a radioisotope, and a biologically active protein.

Another aspect of the present disclosure provides a detection kit, which includes the VHH, the fusion protein, or the immunoconjugate.

Another aspect of the present disclosure provides a pharmaceutical composition, which includes the VHH, the fusion protein, or the immunoconjugate.

In some embodiments of the present disclosure, the pharmaceutical composition further includes a pharmaceutically acceptable carrier.

Another aspect of the present disclosure provides a cell, which includes a membrane-bound polypeptide, and the cell is a T lymphocyte, a macrophage, or an NK cell. The polypeptide includes an antigen recognition domain, a hinge region, a transmembrane region, and an intracellular signal domain; the antigen recognition domain includes the VHH.

Another aspect of the present disclosure provides the use of the VHH, the fusion protein, the immunoconjugate, the pharmaceutical composition, or the cell in the preparation of a drug for diagnosing, treating, or preventing a disease associated with cells expressing CLD18A2.

In some embodiments of the present disclosure, the disease associated with cells expressing CLD18A2 is selected from a tumor, and the tumor is selected from the group consisting of gastric cancer, esophageal cancer, pancreatic cancer, lung cancer, ovarian cancer, colon cancer, liver cancer, head and neck cancer, and gallbladder cancer.

DETAILED DESCRIPTION

Figure 1:
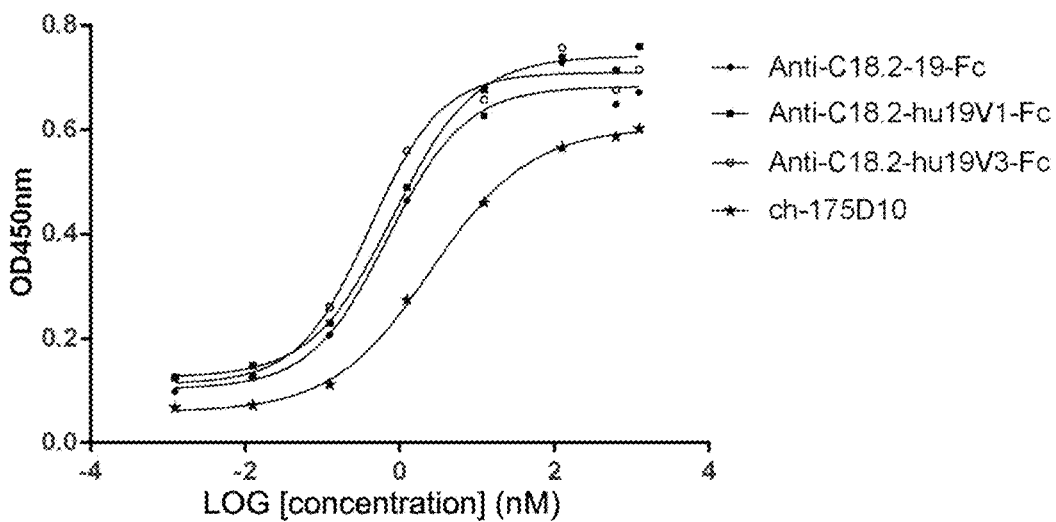
FIG. 1 shows the binding curve (Elisa) of the Anti-C18.2-Fc fusion protein of the present disclosure against the cell surface antigen CLD18A2.

After in-depth research, the present disclosure provides a VHH capable of specifically binding to the epitope on CLD18A2, and further provides a fusion protein including the VHH, an immunoconjugate, and cells expressing a chimeric antigen receptor targeting CLD18A2. The protein or cells have good specificity and affinity for CLD18A2, and have a noticeable tumor suppression effect. The present disclosure is completed on this basis.

The term "antibody" or "immunoglobulin" herein, whether it refers to a heavy chain antibody or a conventional 4-chain antibody, is used as a general term to include a full-length antibody, a single chain thereof, and all portions, domains, or fragments thereof (including but not limited to antigen binding domains or fragments, such as VHH domains or VH/VL domains, respectively). In addition, the term "sequence" as used herein (for example, in terms such as "immunoglobulin sequence", "antibody sequence", "single variable domain sequence", "VHH sequence" or "protein sequence") should generally be understood to include both a corresponding amino acid sequence and nucleic acid sequence or nucleotide sequence encoding the sequence, unless a more limited explanation is required herein.

The term "monoclonal antibody" refers to antibody composed of a single molecule. Monoclonal antibodies show single binding specificity and affinity for specific epitopes.

The term "domain" (of polypeptide or protein) refers to a folded protein structure that can maintain its tertiary structure independently of the rest of the protein. Generally speaking, a domain is responsible for a single functional property of a protein, and in many cases, can be added, removed, or transferred to other proteins without losing functions of the rest of the protein and/or the domain.

The terms "Heavy-chain antibody (VHH)" and "nanobody" have the same meaning and refer to the variable region of the heavy chain of an antibody, a heavy-chain antibody (VHH) consisting of only one heavy chain variable region. "Heavy-chain antibody (VHH)" or "nanobody" is one of the smallest antigen-binding fragments with complete functions. Usually, a heavy-chain antibody (VHH) consisting of only one heavy chain variable region is constructed by cloning the variable region of the heavy chain that naturally lacks light chains and heavy chain constant region 1 (CH1) from the serum of alpaca.

The term "heavy-chain antibody (VHH)" refers to an immunoglobulin domain essentially consisting of four "frame regions", which are referred to as "frame region 1" or "FR1", "frame region 2" or "FR2", "frame region 3" or "FR3", and "frame region 4" or "FR4" in the art and hereinafter. The frame regions are separated by three "complementarity determining regions" or "CDRs" which are referred to as "complementarity determining region 1" or "CDR1", "complementarity determining region 2" or "CDR2", and "complementarity determining region 3" or "CDR3" in the art and hereinafter. Therefore, the general structure or sequence of a heavy-chain antibody (VHH) can be expressed as follows: FR1-CDR1-FR2-CDR2-FR3-CDR3-FR4. Heavy-chain antibodies (VHHs) have antigen-binding sites that endow the antibody with specificity for antigens.

The terms "heavy chain single domain antibody", "VHH domain", "VHH", "VHH antibody fragment", "VHH antibody", and "nanobody" ("Nanobody" is a trademark of Ablynx NV, Ghent, Belgium) can be used interchangeably.

The term "IMGT numbering system" refers to an integrated information system specifically for immunoglobulin (IG), T cell receptor (TCR), and major histocompatibility complex (MHC) of humans and other vertebrates, namely THE INTERNATIONAL IMMUNOGENETICS INFORMATION SYSTEM® (Lafranc et al., 2003, Dev.Comp.Immunol. 27(1):55-77). Log in to IMGT (http://www.imgt.org/IMGT_vquest) to analyze light chain and heavy chain genes of an antibody to determine the framework regions (FR) and complementarity determining regions (CDR) of the variable region. The "position" of the CDR in the structure of the immunoglobulin variable domain is conserved among species and exists in a structure called a loop. Therefore, CDR and frame can be easily identified by using a numbering system that aligns sequences of variable domains according to structural characteristics. This information can be used to transplant and replace a CDR residue of immunoglobulins of one species into the frame of an acceptor normally derived from human antibodies. Unless otherwise specified, in the specification, claims, and drawings of the present disclosure, anti-CLD18A2 VHHs are numbered following the IMGT numbering method to determine the CDR regions and FR regions.

The term "specific binding" means a binding that is selective for a certain antigen and can be distinguished from unwanted or non-specific interactions. The capacity of an antigen-binding module to bind to specific antigenic determinants can be obtained by enzyme-linked immunosorbent assay (ELISA) or other techniques well known to those skilled in the art, such as surface plasmon resonance (BIAcore) (Liljeblad et al., Glyco J17, 323-329 (2000)) and immunofluorescence.

The term "humanized antibody" refers to a molecule having an antigen-binding site substantially derived from an immunoglobulin of a non-human species, and the remaining immunoglobulin structure of the molecule is based on the structure and/or sequence of a human immunoglobulin. The antigen-binding site may include a complete variable domain fused to a constant domain, or only a complementarity determining region (CDR) grafted into an appropriate frame region in the variable domain. The antigen-binding site may be of a wild-type, or modified by one or more amino acid substitutions, for example, modified to be more similar to human immunoglobulins. Some humanized antibodies retain all CDR sequences intact (e.g., a humanized VHH containing all three CDRs from alpaca). Some other humanized antibodies make one or more CDRs changed compared to the parent antibodies.

The term "effector function" when referring to antibodies refers to biological activities that can be attributed to the Fc region of the antibody and vary with the isotype of the antibody. Examples of antibody effector functions include C1 q binding and complement-dependent cytotoxicity (CDC), Fc receptor binding, antibody-dependent cell-mediated cytotoxicity (ADCC), antibody-dependent cellular phagocytosis (ADCP), cytokine secretion, down-regulation of cell surface receptors (such as B cell receptors), and B cell activation.

The term "antibody-dependent cell-mediated cytotoxicity" or "ADCC" refers to a form of cytotoxicity, in which secreted immunoglobulins bound to the Fc receptors (FcR) present on certain cytotoxic cells (such as natural killer (NK) cells, neutrophils, and macrophages) and endow cytotoxic effector cells with the ability to specifically bind to target cells carrying the antigen, and then kill the target cells using a cytotoxin. Antibodies "arm" the cytotoxic cells and are absolutely necessary for the killing. NK cells, the main cells mediating ADCC, only express FcγRIII, while monocytes express FcγRI, FcγRII, and FcγRIII. FcR is known to be expressed on hematopoietic cells (see, for example, Ravetch and Kinet, 1991, Annu. Rev. Immunol. 9:457-92). To assess the ADCC activity of a target molecule, an in vitro ADCC assay may be performed (see, for example, U.S. Pat. Nos. 5,500,362 and 5,821,337). The effector cells suitable for the assay include peripheral blood mononuclear cells (PBMC) and natural killer cells (NK).

The term "Complement-dependent cytotoxicity" or "CDC" is another method of cell killing directed by antibodies. For complement activation, IgM is the most effective isotype. Both IgG1 and IgG3 are also very effective in directing CDC through the classical complement activation pathway. Preferably, in this cascade, the formation of antigen-antibody complexes leads to exposure of multiple C1 q binding sites adjacent to CH2 domains of participating antibody molecules (e.g., IgG molecules) (C1q is one of the three subcomponents of complement C1). Preferably, the exposed C1q binding sites convert the previously lowaffinity C1q-IgG interaction into a high-affinity interaction, triggering a cascade that includes a series of other complement proteins and causing the chemotactic/activating C3a and C5a release from effector cells. The complement cascade finally forms a membrane attack complex, which creates pores in the cell membrane to allow water and solutes to move freely in to and out of the cell.

The term "CD3" refers to the multiple subunit complex of the human CD3 protein. The CD3 complex is composed of 6 different polypeptide chains. These polypeptide chains include CD3γ chain (SwissProt P09693), CD3δ chain (SwissProt P04234), two CD3ε chains (SwissProt P07766), and a CD3 chain homodimer (SwissProt 20963) associated with T cell receptor a and 13 chains. The term "CD3" includes any CD3 variants, isomers, and orthologs, which are naturally expressed by cells (including T cells), or may be expressed on cells transfected with genes or cDNAs encoding these polypeptides, unless otherwise stated. Cluster of differentiation 3 (CD3) on the surface of T cells is a co-receptor for T cell receptors and assists in the activation of cytotoxic T cells.

"Sequence identity" between two polypeptide sequences indicates the percentage of identical amino acids between the sequences. "Sequence similarity" indicates the percentage of identical or representative conservative amino acids among different sequences. Methods for evaluating the degree of sequence identity between amino acid sequence or nucleotide sequences are known to those skilled in the art. For example, amino acid sequence identity is usually measured using sequence analysis software. For example, the BLAST program of the NCBI database can be used to determine identity.

The terms "chimeric antigen receptor" and "CAR" are artificial receptors that mimic the function of TCR, and are composed of an antigen recognition domain, a hinge region, a transmembrane region, and an intracellular signal domain connected in sequence. When the antigen (receptor) on the tumor cell surface binds to the antibody (ligand) of the chimeric antigen receptor, the signal is transmitted into the cell through the hinge region and the transmembrane region. The intracellular signal domain then converts the signal into an activation signal to activate the effector cells. The effector cells kill tumor cells by secreting perforin or cytokines. At the same time, the effector cells themselves are also amplified to further enhance the immune killing effect.

The "effective amount" of an agent refers to the amount necessary to cause physiological changes in the cells or tissues to which the agent is administered.

A "therapeutically effective amount" of an agent such as a pharmaceutical composition refers to an amount to achieve desired therapeutic or preventive results at the necessary dosage and time period. For example, a therapeutically effective amount of an agent can eliminate, reduce, delay, minimize or prevent the adverse effects of a disease.

An "individual" or "subject" is a mammal. Mammals include, but are not limited to, domesticated animals (such as cows, sheep, cats, dogs, and horses), primates (humans and non-human primates such as monkeys), rabbits, and rodents (such as mice and rats). Preferably, the individual or subject is a human.

The term "pharmaceutical composition" refers to a formulation that makes the active ingredient contained therein biologically active, and does not contain other ingredients that have unacceptable toxicity to a subject to whom the composition is administered.

"Pharmaceutically acceptable carrier" refers to ingredients other than the active ingredients in the pharmaceutical composition that are not toxic to the subject. Pharmaceutically acceptable carriers include, but not limited to, buffers, excipients, stabilizers, or preservatives.

The term "treatment/prevention" (and grammatical variants thereof) refers to an attempt to change the natural course of a disease in an individual to be treated, and may be for prevention, or clinical intervention implemented during the course of clinical pathology. The desired therapeutic effects include, but are limited to, preventing the occurrence or recurrence of a disease, alleviating symptoms, reducing any direct or indirect pathological consequences of disease, preventing metastasis, slowing the rate of disease progression, improving or alleviating the disease state, and avoiding or improving the prognosis. In some embodiments, the antibody of the present disclosure is used to delay the formation of a disease or delay the progression of a disease.

The term "antigen" is a predetermined antigen to which an antibody can selectively bind. The target antigen may be a polypeptide, protein, nucleic acid, cell, lipid, hapten, or other naturally occurring or synthetic compound. In some embodiments of the present disclosure, the target antigen is a cell expressing CLD18A2, more preferably, the target antigen is a portion of the expressed CLD18A2 molecule.

The term "whole-cell subtractive screening method" is a high-throughput screening technology developed in phage display technology in recent years. The whole-cell subtractive screening method uses paired cells during subtractive panning a phage library, and short peptides that bind to target cells with high affinity can be screened in a short time.

An "epitope" is a site on the surface of an antigen molecule that is recognized and bound by a single antibody molecule, such as a localized region on the surface of the antigen that is capable of binding to one or more antigen-binding regions of an antibody and that has antigenic or immunogenic activity for triggering an immune response in animals such as mammals (for example, humans). The epitope with immunogenic activity is the portion of the polypeptide that triggers an antibody response in the animals. An epitope having antigenic activity is an antibody-bound portion of a polypeptide as determined by any method well known in the art, including, for example, by immunoassay. Antigenic epitopes are not necessarily immunogenic. Epitopes are often composed of chemically active surface clusters of molecules (such as amino acids or sugar side chains) and have specific three-dimensional structural characteristics as well as specific charge characteristics. The epitopes may be linear epitopes or conformational epitopes. Linear epitopes are formed by contiguous amino acid sequences in proteins. Conformational epitopes are formed by amino acids that are not contiguous in the protein sequence, but come together after the protein is folded into three-dimensional structure. An induced epitope is formed when the three-dimensional structure of a protein altered after activation or binding to another protein or ligand. In certain embodiments, the CLD18A2 epitope is a three-dimensional structure. In other embodiments, the CLD18A2 epitope is a linear structure. Generally, antigens have several different epitopes and react with many different antibodies.

VHH

A first aspect of the present disclosure provides an anti-CLD18A2 VHH. A complementarity determining region (CDR) of the anti-CLD18A2 VHH includes CDR1-CDR3 having amino acid sequences as shown below: CDR1 having an amino acid sequence represented by one of SEQ ID NO. 4-11, CDR2 having an amino acid sequence represented by one of SEQ ID NO. 19-26, and CDR3 having an amino acid sequence represented by one of SEQ ID NO.33-39. In some specific embodiments of the present disclosure, the CDR of the anti-CLD18A2 VHH includes CDR1-CDR3 having amino acid sequences as shown below:

(1) CDR1 having an amino acid sequence represented by SEQ ID NO. 4, CDR2 having an amino acid sequence represented by SEQ ID NO. 19, and CDR3 having an amino acid sequence represented by SEQ ID NO. 33; or (2) CDR1 having an amino acid sequence represented by SEQ ID NO. 5, CDR2 having an amino acid sequence represented by SEQ ID NO. 20, and CDR3 having an amino acid sequence represented by SEQ ID NO. 34; or (3) CDR1 having an amino acid sequence represented by SEQ ID NO. 6, CDR2 having an amino acid sequence represented by SEQ ID NO. 21, and CDR3 having an amino acid sequence represented by SEQ ID NO. 35; or (4) CDR1 having an amino acid sequence represented by SEQ ID NO. 7, CDR2 having an amino acid sequence represented by SEQ ID NO. 22, and CDR3 having an amino acid sequence represented by SEQ ID NO. 36; or (5) CDR1 having an amino acid sequence represented by SEQ ID NO. 8, CDR2 having an amino acid sequence represented by SEQ ID NO. 23, and CDR3 having an amino acid sequence represented by SEQ ID NO. 37; or (6) CDR1 having an amino acid sequence represented by SEQ ID NO. 9, CDR2 having an amino acid sequence represented by SEQ ID NO. 24, and CDR3 having an amino acid sequence represented by SEQ ID NO. 38; or (7) CDR1 having an amino acid sequence represented by SEQ ID NO. 10, CDR2 having an amino acid sequence represented by SEQ ID NO. 25, and CDR3 having an amino acid sequence represented by SEQ ID NO. 36; or (8) CDR1 having an amino acid sequence represented by SEQ ID NO. 11, CDR2 having an amino acid sequence represented by SEQ ID NO. 26, and CDR3 having an amino acid sequence represented by SEQ ID NO. 39;

The anti-CLD18A2 antigen VHH of the present disclosure may include a frame region FR, which includes FR1-FR4 having amino acid sequences as shown below:

(1) FR1 having an amino acid sequence represented by SEQ ID NO. 1, FR2 having an amino acid sequence represented by SEQ ID NO. 12, FR3 having an amino acid sequence represented by SEQ ID NO. 27, and FR4 having an amino acid sequence represented by SEQ ID NO. 40; or (2) FR1 having an amino acid sequence represented by SEQ ID NO. 2, FR2 having an amino acid sequence represented by SEQ ID NO. 13, FR3 having an amino acid sequence represented by SEQ ID NO. 28, and FR4 having an amino acid sequence represented by SEQ ID NO. 41; or (3) FR1 having an amino acid sequence represented by SEQ ID NO. 3, FR2 having an amino acid sequence represented by SEQ ID NO. 14, FR3 having an amino acid sequence represented by SEQ ID NO. 29, and FR4 having an amino acid sequence represented by SEQ ID NO. 41; or (4) FR1 having an amino acid sequence represented by SEQ ID NO. 1, FR2 having an amino acid sequence represented by SEQ ID NO. 15, FR3 having an amino acid sequence represented by SEQ ID NO. 30, and FR4 having an amino acid sequence represented by SEQ ID NO. 41; or (5) FR1 having an amino acid sequence represented by SEQ ID NO. 2, FR2 having an amino acid sequence represented by SEQ ID NO. 16, FR3 having an amino acid sequence represented by SEQ ID NO. 31, and FR4 having an amino acid sequence represented by SEQ ID NO. 41; or (6) FR1 having an amino acid sequence represented by SEQ ID NO. 2, FR2 having an amino acid sequence represented by SEQ ID NO. 13, FR3 having an amino acid sequence represented by SEQ ID NO. 31, and FR4 having an amino acid sequence represented by SEQ ID NO. 41; or (7) FR1 having an amino acid sequence represented by SEQ ID NO. 1, FR2 having an amino acid sequence represented by SEQ ID NO. 17, FR3 having an amino acid sequence represented by SEQ ID NO. 30, and FR4 having an amino acid sequence represented by SEQ ID NO. 41; or (8) FR1 having an amino acid sequence represented by SEQ ID NO. 2, FR2 having an amino acid sequence represented by SEQ ID NO. 18, FR3 having an amino acid sequence represented by SEQ ID NO. 32, and FR4 having an amino acid sequence represented by SEQ ID NO. 41.

The amino acid sequence of the anti-CLD18A2 VHH of the present disclosure may include: a) an amino acid sequence represented by one of SEQ ID NO. 42-49; or b) an amino acid sequence that has at least 80% sequence identity with one of SEQ ID NO. 42-49 and has the function of the amino acid sequence defined in a). Specifically, the amino acid sequence in b) specifically refers to: a polypeptide fragment obtained by substituting, deleting or adding one or more (specifically 1-50, 1-30, 1-20, 1-10, 1-5, or 1-3) amino acids in an amino acid sequence as shown in one of SEQ ID No.42-49, or by adding one or more (specifically 1-50, 1-30, 1-20, 1-10, 1-5, or 1-3) amino acids to the N-terminal and/or C-terminal of an amino acid sequence as shown in one of SEQ ID No.42-49, and having a function (for example, the ability specifically bind to CLD18A2) of a polypeptide fragment as shown in one of SEQ ID No.42-49. The amino acid sequence in b) may have at least 80%, at least 85%, at least 90%, at least 93%, at least 95%, at least 97%, or at least 99% homology with one of SEQ ID No.42-49. The anti-CLD18A2 VHH of the present disclosure can specifically bind to cells expressing CLD18A2. For example, the anti-CLD18A2 VHH may bind to cells expressing CLD18A2 or may not bind to cells that do not express CLD18A2 but express CLD18A1. That is, the anti-CLD18A2 VHH only recognizes CLD18A2 but not CLD18A1.

The anti-CLD18A2 VHH of the present disclosure may be a humanized antibody. Humanization can effectively reduce the immunogenicity of the antibody. The humanized VHH can retain at least one functional property of the antibody, for example, the ability to specifically bind to CLD18A2. In a specific embodiment of the present disclosure, the amino acid sequence of the anti-CLD18A2 humanized VHH is represented by one of SEQ ID NO. 67-90.

Fusion Protein

A second aspect of the present disclosure provides a fusion protein of an anti-CLD18A2 VHH, including a first domain of the VHH provided in the first aspect of the present disclosure, and a second domain for prolonging the half-life in vivo and/or binding to effector cells. The fusion protein may specifically bind to cells expressing CLD18A2.

In the second domain, the fragment for prolonging the half-life in vivo may include a serum albumin fragment, a polyethylene glycol fragment, or an HSA-binding domain (for example, an HSA-binding VHH), and the like. In the second domain, the fragment that binds effector cells may include an immunoglobulin Fc region, preferably selected from a human immunoglobulin Fc region. The human immunoglobulin Fc region includes a mutation for altering an Fc-mediated effector function, and the effector function includes one or more of CDC activity, ADCC activity, and ADCP activity. The immunoglobulin may be selected from one or more of IgG, IgA1, IgA2, IgD, IgE, and IgM, and the IgG may be specifically selected from one or more of IgG1, IgG2, IgG3, and IgG4 subtypes. The immunoglobulin Fc region contained in the VHH fusion protein allows the fusion protein to form a dimer, while prolonging the half-life of the fusion protein in vivo and increasing the Fc-mediated functions. In a specific embodiment of the present disclosure, the immunoglobulin Fc region may be an Fc region of human IgG1, more specifically a wild-type IgG1 Fc sequence, which may be introduced with a mutation for altering an Fc-mediated effector function, for example, a) a mutation for altering Fc-mediated CDC activity; b) a mutation for altering Fc-mediated ADCC activity; or c) a mutation for altering Fc-mediated ADCP activity. In another specific embodiment of the present disclosure, the amino acid sequence of the immunoglobulin Fc region is selected from one of SEQ ID NO. 91-95. In the second domain, the fragment that binds to effector cells may further include a molecule that has a high affinity for cluster of differentiation 3 (CD3) on T cells or a molecule that binds to cluster of differentiation 3 (CD3) on T cells. Preferably, the molecule is an anti-CD3 VHH having an amino acid sequence shown in SEQ ID NO.131.

In the anti-CLD18A2 VHH fusion protein of the present disclosure, a connecting peptide may be provided between the first domain and the second domain. The connecting peptide may be a flexible polypeptide chain composed of alanine (A) and/or serine (S) and/or glycine (G). The length of the connecting peptide may be 3-40 amino acids, preferably 3-9 amino acids, 9-12 amino acids, 12-16 amino acids, 16-20 amino acids, 20-25 amino acids, 25-30 amino acids, 30-35 amino acids, or 35-40 amino acids. In another specific embodiment of the present disclosure, the connecting peptide may be 8 or 15 or 35 amino acids.

In a preferred embodiment, by using serum from healthy people as the source of complement, the Anti-C18.2-Fc killed CLD18A2 positive cells, and the proportion of cell lysis is higher than that of the positive control ch-175D10.

In another preferred embodiment, the Anti-CLDN18×CD3 fusion protein has a tumor recognition portion Anti-C18.2, and the other arm of the molecule is specific for T cell antigens (effector cell binding arm) (mainly CD3). By binding to target antigens at the same time, T lymphocytes are directed to tumor cells and activated at the tumor cells, where the T lymphocytes can perform their cytolytic function. The anti-CD3 portion can bind to CD3 in the TCR receptor complex on the surface of T cells, and can provide the first signal for activation of T cells (similar to the binding of MHC-peptide complexes on antigen-presenting cells to TCR), which facilitates the activation of T cells. The Anti-CLDN18×CD3 fusion protein contains a a domain for CD3 binding and enrichment of T cells around tumor cells and improve the killing efficiency of T cells on tumor cells.

Isolated Polynucleotide

A third aspect of the present disclosure provides an isolated polynucleotide, which encodes the VHH provided by the first aspect of the present disclosure or the fusion protein provided by the second aspect of the present disclosure. The polynucleotide may be RNA, DNA, cDNA, or the like. The method for providing the isolated polynucleotide should be known to those skilled in the art. For example, the isolated polynucleotide may be prepared by automated DNA synthesis and/or recombinant DNA technology, or may be isolated from a suitable natural source. In a specific embodiment of the present disclosure, the nucleic acid sequence of the isolated polynucleotide is shown in one of SEQ ID NO:119-130.

Expression Vector

A fourth aspect of the present disclosure provides an expression vector, which includes the isolated polynucleotide provided by the third aspect of the present disclosure. The method for constructing the expression vector should be known to those skilled in the art. For example, the expression vector may be constructed by in vitro recombinant DNA, DNA synthesis, in vivo recombination, and other methods. More specifically, the expression vector may be constructed by inserting the isolated polynucleotide into a multiple cloning site of an expression vector. The expression vector of the present disclosure generally refers to various commercially available expression vectors that are well known in the art. For example, the expression vectors may be bacterial plasmids, bacteriophages, yeast plasmids, plant cell viruses, mammalian cell viruses such as adenoviruses and retroviruses, or other vectors. The vector may further include one or more regulatory sequences operatively connected to the polynucleotide sequence, and the regulatory sequences may include a suitable promoter sequence. The promoter sequence is usually operatively connected to the coding sequence of the amino acid sequence to be expressed. The promoter may be any nucleotide sequence that shows transcriptional activity in the selected host cell, including mutant, truncated, and hybrid promoters, and may be obtained from genes encoding extracellular or intracellular polypeptides that are homologous or heterologous to the host cell. The regulatory sequence may further include a suitable transcription terminator sequence, which is a sequence recognized by the host cell to terminate transcription. The terminator sequence is connected to the 3'end of the nucleotide sequence encoding the polypeptide. Any terminator that is functional in the selected host cell can be used in the present disclosure.

Generally speaking, a suitable vector may contain an origin of replication that functions in at least one organism, a promoter sequence, a convenient restriction enzyme site, and one or more selectable markers. For example, these promoters may include, but are not limited to, the lac or trp promoters of *Escherichia coli* (*E. coli*), the lambda phage PL promoter, eukaryotic promoters (including CMV immediate early promoter, HSV thymidine kinase promoter, early and late SV40 promoters, methanol oxidase promoter of *Pichia pastoris*) and other well-known promoters that are capable of controlling gene expression in prokaryotic cells or eukaryotic cells or viruses. Marker genes may be used to provide phenotypic characters for the selection of transformed host cells. For example, marker genes may include but are not limited to dihydrofolate reductase, neomycin resistance, and green fluorescent protein (GFP) for eukaryotic cell culture, or tetracycline resistance or ampicillin resistance for *E. coli*. When the polynucleotide is expressed, the expression vector may further include an enhancer sequence. The transcription will be enhanced if the enhancer sequence is inserted into the vector. Enhancers are cis-acting factors of DNA, typically containing about 10-300 base pairs. Enhancers act on promoters to enhance gene transcription.

Expression System

A fifth aspect of the present disclosure provides an antibody expression system, which includes the expression vector provided by the fourth aspect of the present disclosure or incorporates the exogenous polynucleotide provided by the third aspect of the present disclosure in the genome. Any cell suitable for the expression of an expression vector can act as a host cell. For example, the host cell may be a prokaryotic cell, such as a bacterial cell; or a lower eukaryotic cell, such as a yeast cell; or a higher eukaryotic cell, such as a mammalian cell, specifically including but not limited to *E. coli* and Streptomyces; or a bacterial cell of *Salmonella typhimurium*; or a fungal cell such as a yeast cell, a filamentous fungi cell or a plant cell; or an insect cell of Drosophila S2 or Sf9; or one or more of CHO cell, COS cell, HEK293 cell, and an animal cell such as a Bowes melanoma cell. The method for constructing the expression system should be known to those skilled in the art. For example, the methods for constructing the expression system may include, but are not limited to, one or more of microinjection, gene gun, electroporation, virus-mediated transformation, electron bombardment, and calcium phosphate precipitation.

Immunoconjugate

A sixth aspect of the present disclosure provides an immunoconjugate, which includes the VHH provided by the first aspect of the present disclosure or the fusion protein provided by the second aspect of the present disclosure. The immunoconjugate usually includes a coupling portion, and the coupling portion may include, but is not limited to, one or more of a detectable label, a cytotoxin, a radioisotope, and a biologically active protein. The method for preparing the immunoconjugate should be known to those skilled in the art. For example, the VHH and/or fusion protein and the coupling portion may be connected directly or by a spacer of a suitable length so as to obtain the immunoconjugate through chemical crosslinking or genetic engineering fusion expression. For therapeutic purposes, therapeutic effector groups such as radioactive groups may be suitable. The radioactive groups are composed of radioisotopes or radionuclides (e.g., $^{3}$H, $^{14}$C, $^{15}$N, $^{33}$P, $^{35}$S, $^{90}$Y, $^{99}$Tc, $^{111}$n, $^{123}$I, $^{125}$I, $^{131}$I, $^{201}$Tl, $^{213}$Bi), a toxin or a cytotoxic group such as a cytostatic agent, or a group including the same. On the other hand, the polypeptide of the present disclosure may be coupled with a labeling group (labeled polypeptide), which can then be used, for example, for diagnostic purposes. Suitable labeling groups may be selected from radioisotopes (such as those mentioned above), groups containing radioisotopes or radionuclides, fluorescent groups (e.g., fluorescent proteins (such as GFP and RFP), dyes, rhodamine, fluorescein and derivatives thereof (such as FITC and cyanine dyes)), enzyme groups (e.g., horseradish peroxidase, alkaline phosphatase, β-galactosidase), chemiluminescent groups, biotin groups, metal particles (e.g., gold particles), magnetic particles (for example, having a core containing magnetite ($Fe_{3}O_{4}$) and/or maghemite ($Fe_{2}O_{3}$)), predetermined polypeptide groups, and the like.

Detection Kit

A seventh aspect of the present disclosure provides a detection kit, which includes the VHH provided by the first aspect of the present disclosure, the fusion protein provided by the second aspect of the present disclosure, or the immunoconjugate provided by the sixth aspect of the present disclosure. The kit may further include a container, a control (a negative or positive control), a buffer, an auxiliary agent and the like as needed, which can be selected by those skilled in the art based on specific conditions.

The present disclosure further provides a detection method, which can be used to detect CLD18A2 protein. The detection method may include: obtaining a cell and/or tissue sample; dissolving the sample in a medium; and detecting the CLD18A2 protein in the dissolved sample. In a specific embodiment of the present disclosure, the detection object may be a cell-containing sample existing in a cell preservation solution. In another specific embodiment of the present disclosure, the VHH is further conjugated with fluorescent dyes, chemicals, polypeptides, enzymes, isotopes, or tags that can be used for detection or can be detected by other reagents.

Pharmaceutical Composition

An eighth aspect of the present disclosure provides a pharmaceutical composition, which includes the anti-CLD18A2 VHH provided by the first aspect of the present disclosure, the anti-CLD18A2 VHH fusion protein provided by the second aspect of the present disclosure, or the immunoconjugate provided by the sixth aspect of the present disclosure.

The pharmaceutical composition may further include various pharmaceutically acceptable carriers in the art. The pharmaceutically acceptable carriers are non-toxic to the recipient at the dose and concentration used, and may specifically include, but are not limited to: buffers, such as acetate, Tris, phosphate, citrate and other organic acids; antioxidants, including ascorbic acid and methionine; preservatives (such as octadecyl dimethyl benzyl ammonium chloride; hexamethonium chloride; benzalkonium chloride, benzethonium chloride; phenol, butanol or benzyl alcohol; alkyl ester of p-hydroxybenzoic acid, such as methyl p-hydroxybenzoate or propyl p-hydroxybenzoate; catechol; resorcinol; cyclohexanol; 3-pentanol; and m-cresol); proteins, such as serum albumin, gelatin or immunoglobulin; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrin; chelating agents, such as EDTA; tension conditioning agents, such as trehalose and sodium chloride; sugars, such as sucrose, mannitol, trehalose or sorbitol; surfactants, such as polysorbate; salt-forming counterions, such as sodium; metal complexes (such as Zn-protein complexes); and/or non-ionic surfactants, such as TWEEN®, PLURONICS® or polyethylene glycol (PEG). Pharmaceutical preparations for in vivo administration are generally sterile. Methods for achieving sterility of pharmaceutical preparations should be known to those skilled in the art. For example, sterility may be realized by methods such as the sterile membrane filtration method. Those skilled in the art may select a suitable pharmaceutically acceptable carrier according to the required dosage form of the pharmaceutical composition, so as to prepare the pharmaceutical composition into different dosage forms. For example, the pharmaceutical composition of the present disclosure may be prepared into various dosage forms, including but not limited to tablets, injections, lyophilized agents, and the like.

In the pharmaceutical composition, the content of the fusion protein and immunoconjugate is usually an effective amount, and the content of the active ingredient corresponding to the effective amount can be determined according to the subject to be treated and the specific administration mode. For example, based on the total mass of the pharmaceutical composition, the content of the fusion protein and immunoconjugate may be about 0.01-99%, 0.1-70%, 1-30%, 0.01-0.05%, 0.05-0.1%, 0.1-0.3%, 0.3-0.5%, 0.5-1%, 1-3%, 3-5%, 5-10%, 10-20%, 20-30%, 30-50%, 50-70%, or 70-99%.

The fusion protein, immunoconjugate, and pharmaceutical composition of the present disclosure may be administered as a single effective component, or may be administered in combination, that is, in combination with other agents. For example, the combination therapy may be the combination of the fusion protein, immunoconjugate, or pharmaceutical composition with at least one other anti-tumor drug. For another example, the combination may be the combined use of the fusion protein, immunoconjugate or pharmaceutical composition with immune checkpoint inhibitors. The immune checkpoint inhibitors include, but are not limited to, one or more PD-1 inhibitors, PD-L1 inhibitors, and CTLA-4 inhibitors, and the inhibitors may preferably be monoclonal antibodies.

Cells Expressing Chimeric Antigen Receptors Targeting CLD18A2

A ninth aspect of the present disclosure provides a cell expressing a chimeric antigen receptor (CAR) targeting CLD18A2. The cell-targeting CLD18A2 usually includes a polypeptide acting as a chimeric antigen receptor, and the polypeptide may include an antigen recognition domain, a hinge region, a transmembrane region, and an intracellular signal domain. Methods for constructing the chimeric antigen receptor should be known to those skilled in the art. For example, the transmembrane region may be selected from the following: a CD protein (such as CD4, CD8, CD3 or CD28), a T cell receptor subunit (such as $\alpha$, $\beta$, $\gamma$, or $\delta$), an IL-2 receptor subunit ($\alpha$ chain), a low-affinity nerve growth factor receptor (LNGFR or p75) subunit ($\beta$ chain or $\gamma$ chain), or a subunit of the Fc receptor. In a specific embodiment of the present disclosure, the transmembrane region includes a transmembrane domain of CD4, CD8, or CD28. In another specific embodiment of the present disclosure, the transmembrane region includes a transmembrane region of CD4 or CD8 (for example, CD8$\alpha$ chain, as described in NCBI reference number: NP_001139345.1, or a fragment thereof). In another specific embodiment of the present disclosure, the CAR further includes a hinge region between the antigen recognition domain and the transmembrane region. In another specific embodiment of the present disclosure, the hinge is selected from CD8 (for example, CD8$\alpha$), or the CH2 and/or CH3 domains of IgG1 or IgG4. Preferred examples of intracellular signal domains for CAR may be the cytoplasmic sequences of natural T cell receptors (TCR) and co-receptors that act synergistically to initiate signal transduction after antigen binding, or any derivatives or variants of these sequences, or any synthetic sequences having the same function. Intracellular signal domains can be divided into two categories: those that initiate antigen-dependent primary activation, and those that act in an antigen-independent manner to provide secondary or co-stimulatory signals. The primary activation effector domain may contain a signal transduction motif, which is known as an immunoreceptor tyrosine-based activation motif (ITAM). ITAM is a well-defined signal transduction motif, usually present in the cytoplasmic tail of a variety of receptors, and acting as a binding site for syk/zap70 tyrosine kinases. As non-limiting examples, examples of ITAMs used in the present disclosure may include those derived from CD3$\zeta$, FcR$\gamma$, FcR$\beta$, FcR$\epsilon$, CD3$\gamma$, CD3$\delta$, CD3$\epsilon$, CD5, CD22, CD79a, CD79b, and CD66d. In a specific embodiment of the present disclosure, the intracellular signal domain includes a CD3$\zeta$ signal transduction domain (also referred to as CD247). Natural TCR contains CD3$\zeta$ signal transduction molecules, so TCR constructs using this effector domain is most similar to TCR constructs occurring in nature. In another specific embodiment of the present disclosure, the CD3$\zeta$ signal transduction domain includes a sequence described in NCBI Reference No: NP_932170, or a fragment thereof with activating or stimulating activity. As described in the present disclosure, the intracellular signal domain can also provide secondary or co-stimulatory signals. T cells further include co-stimulatory molecules that bind to cognate co-stimulatory ligands on antigen-presenting cells so as to enhance T cell responses, for example, by increasing proliferation activation, differentiation, and the like. Therefore, in a specific embodiment of the present disclosure, the intracellular signal domain further includes a co-stimulatory domain. In another specific embodiment of the present disclosure, the co-stimulatory domain includes an intracellular domain of a co-stimulatory molecule, which is selected from CD28, CD27, 4-1BB (CD137), OX40 (CD134), ICOS (CD278), CD30, CD40, PD-1 (CD279), CD2, CD7, NKG2C (CD94), B7-H3 (CD276), or any combination thereof. In yet another embodiment, the co-stimulatory domain includes an intracellular domain of a co-stimulatory molecule, which is selected from CD28, CD27, 4-1BB, OX40, ICOS, or any combination thereof. In another specific embodiment of the present disclosure, the co-stimulatory domain includes CD28, for example, as described in NCBI Reference No: NP_006130, or a fragment thereof having an activating or stimulating activity.

Methods for constructing cells targeting CLD18A2 through the chimeric antigen receptor should be known to those skilled in the art. For example, the cells may be T lymphocytes, macrophages and/or NK cells. When the VHH binds to the CLD18A2 antigen, the T lymphocytes, macrophages, and/or NK cells can be activated and/or stimulated to kill cells expressing CLD18A2.

In a preferred embodiment of the present disclosure, the antigen recognition domain includes the VHH provided in the first aspect of the present disclosure, the hinge is selected from CD8, the transmembrane region is CD28 (labeled as CD28a in the embodiments), the co-stimulatory domain in the intracellular signal domain is selected from CD28 (labeled as CD28b in the embodiments) or a combination of CD28 and CD137, and the intracellular signal domain further includes a CD3 signal transduction domain. In a preferred embodiment, the CAR-T cells targeting CLD18A2 have obvious killing effects in vitro and in vivo.

Use

A tenth aspect of the present disclosure provides the use of the VHH provided by the first aspect of the present disclosure, the fusion protein provided by the second aspect of the present disclosure, the immunoconjugate provided by the sixth aspect of the present disclosure, the pharmaceutical composition provided by the eighth aspect of the present disclosure, the polypeptide acting as a chimeric antigen receptor provided by the ninth aspect of the present disclosure, or the cell expressing chimeric antigen receptors targeting CLD18A2 provided by the ninth aspect of the present disclosure in the preparation of a drug for diagnosing, treating, or preventing diseases associated with cells expressing CLD18A2.

The "therapeutically effective amount" of the VHH, fusion protein, immunoconjugate, and pharmaceutical composition provided by the present disclosure preferably results in a reduction in the severity of disease symptoms, an increase in the frequency and duration of asymptomatic periods of the disease, or prevention of injury or disability caused by the pain of the disease. For example, for the treatment of CLD18A2 positive tumors (for example, gastric cancer), a "therapeutically effective amount" preferably inhibits cell growth or tumor growth by at least about 10% compared with untreated subjects, preferably by at least about 20%, more preferably by at least about 30%, more preferably by at least about 40%, more preferably by at least about 50%, more preferably by at least about 60%, more preferably by at least about 70%, and more preferably by at least about 80%. The ability to inhibit tumor growth may be evaluated in an animal model system that predicts the efficacy in human tumors. Alternatively, the ability to inhibit tumor growth may be evaluated by examining the ability to inhibit cell growth, and this inhibition can be determined in vitro by tests well known to those skilled in the art. A therapeutically effective amount of VHHs, fusion proteins, immunoconjugates, and pharmaceutical compositions can generally reduce the tumors volume or otherwise alleviate the symptoms of the subject. Those skilled in the art may select a suitable therapeutically effective amount according to the actual situation, for example, age of the subject, severity of the subject's symptoms, and the selected specific composition or administration route. The prescription of the treatment (for example, the decision on the dosage) may be determined by a physician, and the factors usually considered include, but not limited to, the disease to be treated, the condition of the individual patient, the administration site, the administration route, and others. A preventive effective amount refers to an amount effective to achieve a desired preventive effect with a necessary dosage and time period. Usually, but not necessarily, since the preventive dose is administered to a subject before the onset of the disease or in an early stage of the disease, the "preventive effective amount" is lower than the "therapeutically effective amount". Examples of diseases related to cells expressing CLD18A2 that can be diagnosed, treated, and/or prevented by the present disclosure may include all tumors expressing CLD18A2, specifically including but not limited to gastric cancer, esophageal cancer, pancreatic cancer, lung cancer, ovarian cancer, colorectal cancer, liver cancer, gallbladder cancer, and head and neck cancer. These cancers may be early-stage cancer, mid-stage cancer, or advanced cancer, such as metastatic cancer.

The embodiments of the present disclosure will be described below through exemplary embodiments. Those skilled in the art can easily understand other advantages and effects of the present disclosure according to contents disclosed by the specification. The present disclosure may also be implemented or applied through other different specific implementation modes. Various modifications or changes may be made to all details in the specification based on different points of view and applications without departing from the spirit of the present disclosure.

Before further describing the specific embodiments of the present disclosure, it is understood that the scope of the present disclosure is not limited to the specific embodiments described below; it is also to be understood that the terminology of the disclosure is used to describe the specific embodiments, and not to limit the scope of the disclosure;

When numerical values are given by the embodiments, it is to be understood that two endpoints of each numerical range and any one between the two may be selected unless otherwise stated. Unless otherwise defined, all technical and scientific terms used in the present disclosure have the same meaning as commonly understood by one skill in the art. In addition to the specific method, equipment, and material used in the embodiments, any method, equipment, and material in the existing technology similar or equivalent to the method, equipment, and material mentioned in the embodiments of the present disclosure may be used to realize the invention according to the grasp of the existing technology and the record of the invention by those skilled in the art.

Unless otherwise stated, the experimental methods, detection methods, and preparation methods disclosed in the present disclosure all employ conventional techniques of molecular biology, biochemistry, chromatin structure and analysis, analytical chemistry, cell culture, recombinant DNA technology in the technical field and related fields. These techniques are well described in the existing literature. For details, see Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; The series METHODS IN ENZYMOLOGY, Academic Press, San Diego; Wolffe, CHROMATIN STRUCTURE AND FUNCTION, Third Edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.) Humana Press, Totowa, 1999, and the like.

Embodiment 1: Construction and Detection of Cell Strains Expressing CLD18A2 pCDNA3.1 vectors (Life Technologies) containing the full-length genes of CLD18A1 (amino acid sequence, SEQ ID NO.96) and CLD18A2 (amino acid sequence, SEQ ID NO.97) are extracted respectively with a plasmid maxiprep extraction kit (Biomiga). The plasmids are subjected to sterile filtration and then electro-transfected into CHO-S cells. G418 (sigma) is added while plating in 96-well plate in order to screening for CHO-S-CLD18A1 and CHO-S-CLD18A2 stably transfected cell stains. The stably transfected cell stains on the 96-well plate are selected, then gradually amplified under the culture condition with added G418, and detected by Dot blotting with anti-Claudin18 antibody [34H14L15] (ABCAM) to identify CLD18A1 and CLD18A2 positive clones. NUGC-4-CLD18A1 and NUGC-4-CLD18A2 are constructed by the same method. The gastric adenocarcinoma cells NUGC-4 are purchased from Wuhan GeneCreate Biological Engineering Co., Ltd. Gastric adenocarcinoma cell line NUGC-4 is CLD18A2 negative according to the result of detection.

Embodiment 2: Construction of Anti-CLD18A2 VHH Library

A healthy alpaca (*Vicugna pacos*) is immunized with the CHO-S-CLD18A2 stably transfected cells in Embodiment 1 at $1.0\times10^7$ cells/ml, and is immunized with 1 ml Freund's complete adjuvant (Sigma). Twenty-one days later, the alpaca is immunized again for a total of 3 immunizations in order to stimulate B cells to express antigen-specific antibodies. One week after three immunizations, 30 ml of alpaca blood is collected by a vacuum blood collection tube. Lymphocytes are isolated by using the lymphocyte isolation medium (Tianjin HaoyangHuake Biological Technology Co., Ltd.), and the total RNA is extracted by Trizol. 3 μg total RNA is reverse transcribed into cDNA with a reverse transcription kit (Invitrogen) according to the manufacturer's instructions. VHH is amplified by nest-PCR with the following primers: the upstream primer 5'-CTTGGTGGTCCTGGCTGC-3' (SEQ ID NO.110) and the downstream primer 5'-GGTACGTGCTGTT-GAACTGTTCC-3' (SEQ ID NO.111) of the first round of PCR; the second round of PCR uses the first round of PCR as the template, the upstream primer is 5'-CATGC-CATGACTGTGGCCCAGGCGGCCCAGKTGCAGCTC-GTGGAGTC-3' (SEQ ID NO.112), and the downstream primer is 5'-CATGCCATGACTCGCGGCCGGCCTGGC-CATGGGGGTCTTCGCTGTGGTGCG-3' (SEQ ID NO.113) or 5'-CATGCCATGACTCGCGGCCGGCCTGG-CCGTCTTGTGGTTTTGGTGTCTTGGG-3' (SEQ ID NO.114) for amplification. The target VHH nucleic acid fragments are recovered, digested by the restriction endonuclease SfiI (NEB), inserted into a phage display vector pcomb3xSS (Addgene plasmid # 63890; RRID: Addgene_63890) digested by the same endonuclease, and connected by the T4 ligase (Takara). The ligation product is transformed into electrocompetent cells ER2738 to construct an Anti-CLD18A2 VHH library. The sample is plated by gradient dilution, and the content of the library is determined to be $1.23\times10^8$. At the same time, 24 clones are randomly selected for PCR detection, and the results show that the insertion rate of the constructed library is 100%.

Embodiment 3: Screening and Identification of Anti-CLD18A2 VHH 3.1 Screening of Anti-CLD18A2 VHH The constructed Anti-CLD18A2 VHH library is packaged with helper phagesM13KO7 (NEB), and the titer of recombinant phages of the display library is $5.7\times10^{13}$PFU/ml. CHO-S-CLD18A2 (18 ml, $7\times10^5$/ml) and CHO-S (15 ml, $3\times10^6$/ml) cells are centrifuged at 300 g for 5 min at 4° C. After centrifugation, the medium supernatant is removed, and the cells are resuspended with PBS. After a second centrifugation, the cells are blocked with 2% non-fat dry milk (diluted with PBS) at room temperature for 1 h. Recombinant phage library (about $5.7\times10^{11}$PFU) is added into the blocked CHO-S cells (about $4.5\times10^7$ cells), and the cells are incubated for 30 minutes at room temperature for two whole-cell subtractive screenings. The supernatant is added into pre-blocked CHO-S-CLD18A2 stably transfected cells (about $1.5\times10^7$). The cells are incubated at room temperature for 1 hour for binding. After another centrifugation, the cells are resuspended and washed with PBS for 5 times. The washed phages are bound to the cells followed by incubation with 1 ml 0.1M Glycine-HCl 1 mg/ml BSA (pH2.2) buffer for 10 minutes for elution, centrifugation to obtain supernatant, and neutralization with 1M pH 8.0 Tris-Cl. The titer of the phages is $3.6\times10^5$PFU/ml. The phage eluent is amplified, and the titer is $1\times10^{13}$ PFU/ml.

$2\times10^{11}$ PFU recombinant phages from the amplified library in the first round of panning are selected and incubated at room temperature for 30 minutes with $3\times10^7$ blocked CHO-S cells for subtractive screening. After centrifugation at 300 g for 5 min at 4° C., the supernatant is incubated with $1\times10^7$ blocked CHO-S-CLD18A1 cells at room temperature for 30 min, and the subtractive screening is carried out again. After the subtractive screening, the supernatant is incubated with $1.5\times10^7$ blocked CHO-S-CLD18A2 cells at room temperature for 1 hour for binding. After centrifugation at 300 g for 5 min at 4° C., re-suspending and washing with PBS. After washing with PBS for 5 times, incubating with 500 μl 0.1M gly-HCl 1 mg/ml BSA (pH2.2) for 10 min for elution. After centrifugation at 300 g for 5 min at 4° C., the supernatant is neutralized with 1M pH8.0 Tris-Cl. The phage titer of the second round of panning is 6×10⁵ PFU/ml. The phage eluent from the second round of panning is amplified and stored in 50% glycerol.

3.2 The First Round of Screening Using Phage Enzyme-Linked Immunoassay (ELISA)

Eighty clones are selected from the phage titer assay plate, eluted in the second round of panning, cultured in a 96-well plate, and infected and packaged with M13KO7 helper phages, to accumulated recombinant phages in the supernatant. CHO-S, CHO-S-CLD18A1, and CHO-S-CLD18A2 are plated in 96-well plates at 5×10$^5$ cells per well, and blocked with 3% BSA at room temperature for 1 h. The 96-well plates corresponding to the three blocked cells are centrifuged with a plate centrifuge at 2000 rpm for 10 min before carefully removing the supernatants. The monoclonal recombinant phage supernatant is diluted three-fold with 3% BSA in 96-well plates, then added to 96-well plates pre-coated with the three cells at 50 μl per well, and incubated for 1 h at room temperature. After washing with PBS for 3 times, adding 100 μl diluted HRP-anti-M13 antibody (Sino Biological Inc.) to each well and incubating at room temperature for 1 h. After washing with PBS for 3 times, adding TMB substrate and incubating at 37° C. After incubating for 5 min to develop color, adding 1M sulfuric acid to terminate the reaction, and reading the optical density at 450 nm (OD450 nm). Based on the ELISA results of the three 96-well plates of CHO-S, CHO-S-CLD18A1, and CHO-S-CLD18A2, those with an optical density (OD) value above 1.5 times of the negative well (the well corresponding to CHO-S) are identified as positive. Clones that are negative on CHO-S-CLD18A1 and positive on CHO-S-CLD18A2 are selected.

3.3 The Second Round of Screening by Enzyme-Linked Immunoassay (ELISA) with *E. coli* Expression Supernatant The clones selected according to the results of the 96-well plates of CHO-S, CHO-S-CLD18A1, and CHO-S-CLD18A2 cells are cultured. pcomb3XSS plasmids containing a single VHH sequence are extracted, and transformed into *E. coli* respectively to expression host Rosetta DE3. The respective expression clones are selected and cultured, then induced with 0.2 mM IPTG at 30° C. overnight to facilitate the periplasm-expressed proteins leakage into the culture medium supernatant. The culture medium supernatant of 16 clones are examined by ELISA again: adding 100 μl/well of 1:5000 diluted mouse anti his tag antibody (R&D Systems, Inc), incubating at room temperature for 1 h, washing, adding 100 μl/well of 1:10000 diluted HRP-Goat anti-mouse IgG antibody (Thermo Scientific), incubating for 1 h at room temperature, and adding TMB to develop color after washing. The negative control is a clone transfected with negative plasmid. The cell ELISA results are shown in Table 1, and the specific binding clones are further selected. These clones are sequenced respectively. Amino acid sequence alignment is performed. Clones with identical sequences are removed and finally 8 different clones are obtained. Table 1 exemplarily shows the obtained specific binding clones.

TABLE 1

| Clone No. | OD450 nm (CHO-S) | OD450 nm (CHO-S-CLD18A1) | OD450 nm (CHO-S-CLD18A2) | VHH amino acid SEQ ID NO |
|---|---|---|---|---|
| C18-1 | 0.121 | 0.122 | 0.682 | |
| C18-6 | 0.104 | 0.142 | 0.623 | 42 |
| C18-7 | 0.135 | 0.132 | 0.594 | 43 |
| C18-10 | 0.129 | 0.125 | 0.410 | |
| C18-15 | 0.101 | 0.189 | 0.685 | 44 |
| C18-19 | 0.132 | 0.121 | 0.565 | 45 |
| C18-20 | 0.112 | 0.128 | 0.528 | 46 |
| C18-28 | 0.103 | 0.121 | 0.470 | 47 |
| C18-32 | 0.105 | 0.107 | 0.526 | 48 |
| C18-34 | 0.119 | 0.505 | 0.513 | |
| C18-47 | 0.114 | 0.123 | 0.548 | |
| C18-52 | 0.531 | 0.486 | 0.571 | |
| C18-53 | 0.132 | 0.212 | 0.208 | |
| C18-63 | 0.138 | 0.292 | 0.221 | |
| C18-69 | 0.121 | 0.253 | 0.608 | 49 |
| C18-74 | 0.125 | 0.279 | 0.563 | |
| Negative control | 0.117 | 0.287 | 0.182 | |

Embodiment 4: Preliminary Evaluation and Identification of Anti-CLD18A2 VHH

4.1 Expression and Purification of Anti-CLD18A2 VHH in Host *E. coli*

The positive plasmid obtained by screening serves as a template in PCR. The upstream primer is 5'-gtttaactt-taagaaggagatatacatatgcaggtgcagctcgtggagtct-3' (SEQ ID NO.115), and the downstream primer is 5'-ggccgcaagcttgtcgacggagctcgaattcttactaatggtgatggt-gatggtgctg-3' (SEQ ID NO.116), and PCR amplification is performed with the high-fidelity DNA Polymerase GVP8 (General Biosystems (Anhui) Corporation Limited). The signal peptide sequence is retained at the 5'end of the sequences, and the HIS-tag coding sequence is retained at the 3'end of the sequence. The PCR product is electrophoresed, and a band of about 500 bp is recovered by excision from the gel. The recovered PCR product is connected with the pET32a+ vector (Novagen, digested with endonucleases NdeI and EcoRI) using a recombination kit (Novoprotein Scientific Inc). The *E. coli* expression plasmid is constructed and transformed into the *E. coli* competent TOP10F, spread on ampicillin-resistant plates and cultured overnight in an incubator at 37° C. Clones on the ampicillin-resistant plates are picked, respectively. The plasmids are extracted and sequenced to confirm the correct insertion of the sequence in the pET32a+ vector.

The *E. coli* expression plasmid confirmed by sequencing is transformed into the *E. coli* expression host Rosetta (DE3) to construct an *E. coli* expression strain. Recombinant clones are picked from the ampicillin-resistant plate, cultured, and induced to express overnight with 1 mM IPTG at 30° C. The bacteria culture that is induced overnight is subjected to ultrasonication. After centrifugation at 12000 g for 10 min at 4° C., the supernatant is extracted and purified by Ni chromatographic column (Bestchrom Biotechnology Co., Ltd.), and the final protein purity is above 90%.

4.2 Specific Binding of Anti-CLD18A2 VHH

CHO-S, CHO-S-CLD18A1, and CHO-S-CLD18A2 are plated in 96-well plates at 5×10$^5$ cells per well, and blocked with 3% BSA at room temperature for 1 h. The purified Anti-CLD18A2 VHH with HIS-tag is diluted to 2 µg/ml, add 100 µl to the blocked cells, and incubated for 1 h at room temperature. After washing, 100 µl/well of 1:5000 diluted mouse anti-his tag antibody (R&D Systems, Inc) was added and incubated at room temperature for 1 h. After washing, 100 µl/well of 1:10000 diluted HRP-Goat anti-mouse IgG antibody (Thermo Scientific) was added and incubated for 1 h at room temperature. After washing, TMB was added to develop color. The OD value is measured at 450 nm. The results are shown in Table 2.

TABLE 2

| Clone No. | Sample name | OD450 nm (CHO-S) | OD450 nm (CHO-S-CLD18A1) | OD450 nm (CHO-S-CLD18A2) |
|---|---|---|---|---|
| C18-6 | Anti-C18.2-6 | 0.112 | 0.124 | 0.719 |
| C18-7 | Anti-C18.2-7 | 0.121 | 0.132 | 0.658 |
| C18-15 | Anti-C18.2-15 | 0.101 | 0.125 | 0.671 |
| C18-19 | Anti-C18.2-19 | 0.115 | 0.123 | 0.668 |
| C18-20 | Anti-C18.2-20 | 0.128 | 0.130 | 0.621 |
| C18-28 | Anti-C18.2-28 | 0.124 | 0.129 | 0.598 |
| C18-32 | Anti-C18.2-32 | 0.119 | 0.142 | 0.586 |
| C18-69 | Anti-C18.2-69 | 0.122 | 0.128 | 0.573 |
|  | Negative control | 0.109 | 0.121 | 0.142 |

4.3 Affinity Evaluation of Anti-CLD18A2 VHH

CHO-S-CLD18A2 cells are plated in a 96-well plate at $5\times10^5$ cells per well, and blocked with 3% BSA at room temperature for 1 h. The purified Anti-CLD18A2 VHH fused with histidine tag is diluted in gradients with 1% BSA, added to the blocked cells, and incubated for 1 h at room temperature. After washing, 100 µl/well of 1:5000 diluted mouse anti-his tag antibody (R&D Systems, Inc) was added and incubated at room temperature for 1 h. After washing, 100 µl/well of 1:10000 diluted HRP-Goat anti-mouse IgG antibody (Thermo Scientific) was added and incubated for 1 h at room temperature. After washing, TMB was added to develop color. The OD value is detected at 450 nm. The software GraphPad Prism v5.0 is used for data processing and mapping analysis, and the EC50 value of Anti-CLD18A2 VHH against CLD18A2 on cells is obtained to reflect the affinity of the VHH to CLD18A2. The results are shown in Table 3.

TABLE 3

| Sample name | EC50 (nM) |
|---|---|
| Anti-C18.2-6 | 1.53 |
| Anti-C18.2-7 | 2.12 |
| Anti-C18.2-15 | 2.89 |
| Anti-C18.2-19 | 1.25 |
| Anti-C18.2-20 | 1.87 |
| Anti-C18.2-28 | 2.54 |
| Anti-C18.2-32 | 2.21 |
| Anti-C18.2-69 | 2.23 |

Embodiment 5: Humanization of Anti-CLD18A2 VHH

The humanization method is completed by the VHH humanization universal framework transplantation method established by Vincke C et al. (Vincke C, Loris R, Saerens D, Martinez-Rodriguez S, Muyldermans S, Conrath K. J Biol Chem. 2009; 284(5):

3273-3284). The general humanized VHH framework h-NbBcII10FGLA (PDB code: 3EAK) is designed based on sequence homology, and the corresponding CDR region is replaced with the CDR region of the Anti-CLD18A2 VHH. The individual amino acids of the FR2 region are further humanized according to the sequence of the humanized antibody DP-47. At least 3 humanized variants were formed per anti-CLD18A2 VHH. The antibody sequences before and after humanization are shown in Table 4:

TABLE 4

| Clone No. | Before humanization SEQ ID NO | Humanization 1(huV1) SEQ ID NO | Humanization 2(huV2) SEQ ID NO | Humanization 3(huV3) SEQ ID NO |
|---|---|---|---|---|
| C18-6 | 42 | 67 | 75 | 83 |
| C18-7 | 43 | 68 | 76 | 84 |
| C18-15 | 44 | 69 | 77 | 85 |
| C18-19 | 45 | 70 | 78 | 86 |
| C18-20 | 46 | 71 | 79 | 87 |
| C18-28 | 47 | 72 | 80 | 88 |
| C18-32 | 48 | 73 | 81 | 89 |
| C18-69 | 49 | 74 | 82 | 90 |

Embodiment 6: Preparation of Anti-CLD18A2 VHH Antibodies Using Mammalian Cells 6.1 Expression and Purification of Anti-CLD18A2 VHH and Fc Fusion Protein (Anti-C18.2-Fc)

The positive sequence obtained by screening and the humanized sequence serves as the templates. The upstream primer is 5'-gtgctgctgctgtgggtgccaggatc-caccgggcaggtgcagctcgtggagtc-3' (SEQ ID NO.117) and the downstream primer is 5'-gcaggacttgggctcagaa-gacacggtgaccagggtcccctggcc-3' (SEQ ID NO.118), and PCR amplification is performed with the high-fidelity DNA Polymerase GVP8 (General Biosystems (Anhui) Corporation Limited). The PCR product is electrophoresed, and a band of about 400 bp is recovered by excision from the gel. The recovered PCR product is connected with the pCDNA3.1 vector containing a signal peptide and human IgG1Fc sequence (amino acid sequence SEQ NO.91), to construct a cell expression plasmid in which the Anti-CLD18A2 VHH is fused with human IgG1 Fc. The cell expression plasmid in which the Anti-CLD18A2 VHH is fused with human IgG1 Fc is extracted using the endotoxin-free plasmid maxiprep extraction kit (Biomiga). The plasmid and the transfection reagent PEI (Polysciences, Inc.) are mixed evenly at 1:3, and then allowed to stand for 30 min. The mixture is added to HEK293F cells, incubated in a shaking incubator at 37° C., 5% $CO_2$ for 7 days, and centrifuged to collect the supernatant. The supernatant is adjusted to pH7.0 and then loaded onto a ProteinA affinity column (Bestchrom Biotechnology Co., Ltd.), and then eluted with 100% 0.1M Gly-HCl (pH3.0); the eluent is pre-added with 10% 1M Tris-HCl (pH 8.5). Diluting the 100% eluent to a conductivity of 4 ms/cm, adjusting the pH to 5.5, centrifuging (8000 rpm, 4° C., 10 min), adjusting the pH of the supernatant to 5.0, and loading the sample onto a DSP chromatographic column (Bestchrom Biotechnology Co., Ltd.), 0-60% eluents (20 mM NaAc, 0.5M NaCl, pH5.0) are eluted in linear gradients at a flow rate of 2 ml/min for 15 min.

6.2 Expression and Purification of Positive Control Antibody ch-175D10

The chimeric antibody (ch-175D10 in the patent of U.S. Pat. No. 9,751,934B2) is composed of the heavy chain (SEQ ID NO.118 in U.S. Pat. No. 9,751,934B2), and the light chain (SEQ ID NO.125 in U.S. Pat. No. 9,751,934B2) is used as a control. The polynucleotide sequence of ch-175D10 is connected with pCDNA3.1 vector. The transient transfection expression and purification of HEK293F cells are performed by the same method as in Embodiment 6.1.

6.3 Comparative Analysis of Aggregation Between Anti-C18.2-Fc Fusion Protein and the Positive Control Antibody ch-175D10

The purity of Anti-C18.2-Fc and the control antibody ch-175D10 is detected by SEC-HPLC-UV analysis. Detector: Agilent 1100 LC; detection wavelength: 214 nm; mobile phase: 150 mM pH7.0 PB +5% isopropanol; chromatographic column: Superdex 200 Increase 5/150 GL; running time: 15 min; column temperature: 25° C.

TABLE 5

| Sample name | SEQ ID NO | Purity (%) | Aggregation (%) |
| --- | --- | --- | --- |
| Anti-C18.2-6-Fc | 98 | 99% | <1% |
| Anti-C18.2-7-Fc | 99 | 99% | <1% |
| Anti-C18.2-15-Fc | 100 | 98% | <1% |
| Anti-C18.2-19-Fc | 101 | 99% | <1% |
| Anti-C18.2-20-Fc | 102 | 97% | <1% |
| Anti-C18.2-28-Fc | 103 | 98% | <1% |
| Anti-C18.2-32-Fc | 104 | 98% | <1% |
| Anti-C18.2-69-Fc | 105 | 98% | <1% |
| Anti-C18.2-hu6V2-Fc | 106 | 98% | <1% |
| Anti-C18.2-hu6V3-Fc | 107 | 98% | <1% |
| Anti-C18.2-hu19V1-Fc | 108 | 99% | <1% |
| Anti-C18.2-hu19V3-Fc | 109 | 99% | <1% |
| ch-175D10 | | 94% | >5% |

From the results in Table 5, the Anti-C18.2-Fc fusion protein of the present disclosure has significantly less aggregation than the control ch-175D10.

Embodiment 7: Characterisation of Anti-C18.2-Fc Fusion Protein Function

7.1 Characterisation of Affinity of Anti-C18.2-Fc Fusion Protein to CLD18A2

The Anti-C18.2-Fc fusion proteins are diluted in gradients with 1% BSA, and the HRP-Goat anti-Human IgG Fc (Novex) secondary antibody is diluted 1:20000. The cell ELISA method is the same as that described in Embodiment 3.2. The software GraphPad Prism v5.0 is used for data processing and mapping analysis. The binding curve and EC50 value of Anti-C18.2-Fc against CLD18A2 in cells are obtained to reflect the affinity of the antibody to CLD18A2.

The results are shown in FIG. 1. The affinities of Anti-C18.2-hu19V1-Fc and Anti-C18.2-hu19V3-Fc are similar to that of Anti-C18.2-19-Fc, which are better than that of the positive control ch-175D10. The EC50 values of Anti-C18.2-19-Fc, Anti-C18.2-hu19V1-Fc, Anti-C18.2-hu19V3-Fc and ch-175D10 are 0.71 nM, 0.82 nM, 0.41 nM and 2.59 nM, respectively. The results show that the humanization of Anti-C18.2 VHH does not lead to significant changes in affinity.

7.2 CDC Assay

Figure 2:
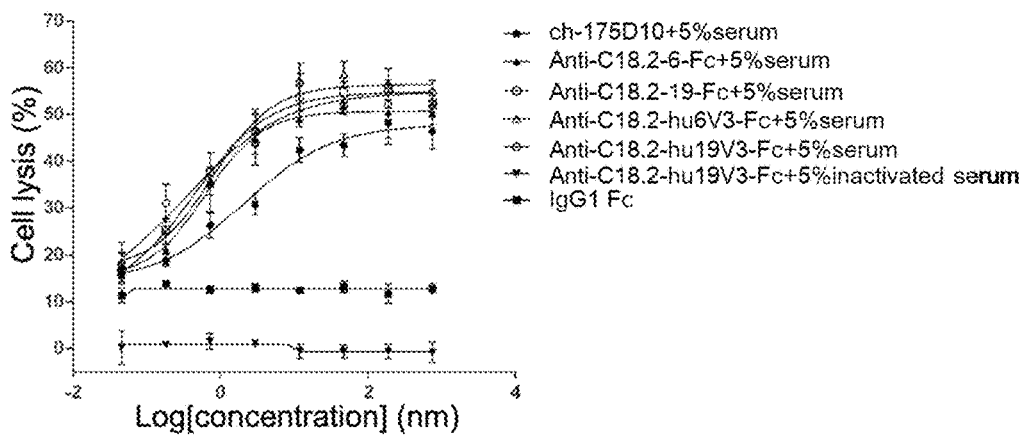
FIG. 2 shows the CDC activity of the Anti-C18.2-Fc fusion protein of the present disclosure.
Figure 3:
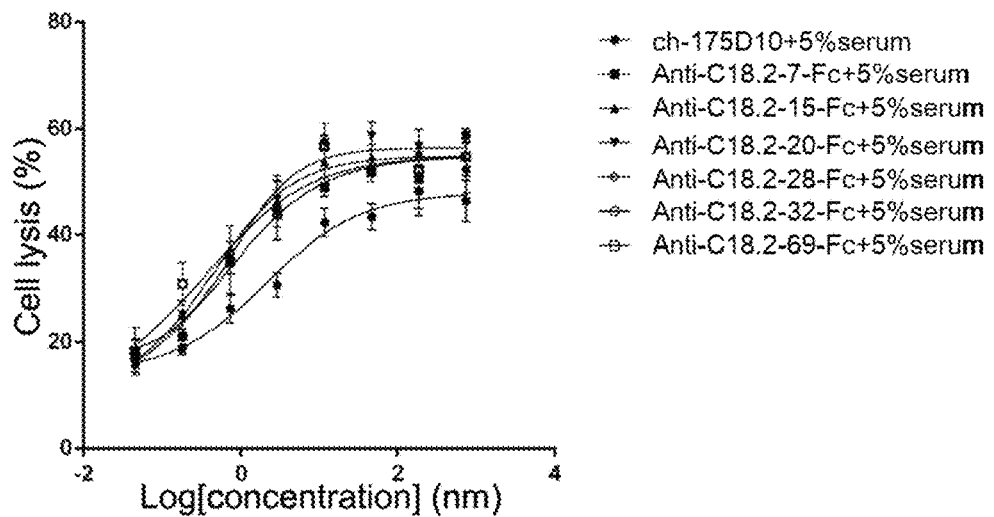
FIG. 3 shows the CDC activity of the Anti-C18.2-Fc fusion protein of the present disclosure.

Serum from healthy donors is used as the source of complement. The serum incubated at 65° C. for 30 min serves as an inactivated serum control. NUGC-4-CLD18A2 cell is plated in a 96-well plate at $5\times10^4$ per well. Anti-C18.2-Fc fusion protein sample, negative control (IgG1 Fc fragment without Fab region, amino acid sequence SEQ NO.91), and positive control antibody ch-175D10 are diluted in gradients with the medium, and then added into 96-well plates, so that the final concentration decreases from 750 nM to 0.05 nM in gradients. After incubating at 37° C. for 30 min, adding 5% healthy human-derived serum or inactivated serum control, respectively, and incubating at 37° C. for 4 h. LDH release is detected with the LDH detection kit (Dojindo Chemical Technology (Shanghai) Co., Ltd.) and carried out according to the manufacturer's instructions. The results are shown in FIGS. 2-3.

7.3 ADCC Assay

Figure 4:
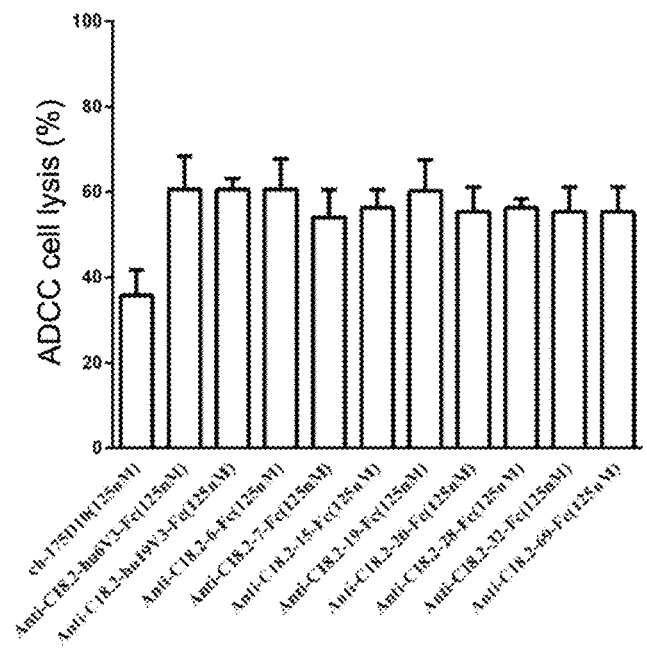
FIG. 4 shows the ADCC activity of the Anti-C18.2-Fc fusion protein of the present disclosure.

Peripheral blood mononuclear cells (PBMC) isolated from human blood from healthy donors are washed and re-suspended in 1640 medium supplemented with 5% fetal bovine serum (FBS). The to-be-tested Anti-C18.2-Fc fusion protein and positive control ch-175D10 are diluted with 5% FBS 1640 medium to 500 nM, and 50 μl was added to 96-well plates. NUGC-4-CLD18A2 is washed and re-suspended with 5% FBS 1640 medium, and configured to have a cell density of about $2\times10^5$/ml, adding 50 μl to the corresponding 96-well plates. The re-suspended PBMC cells was added at 100 μl/well and adjusted to $1\times10^5$ cells per well. As a result, the ratio of effector cells to target cells (E:T ratio) is 10:1. After incubating in a 37° C. incubator for 4 h, LDH release is detected with the LDH detection kit (Dojindo Chemical Technology (Shanghai) Co., Ltd.) and carried out according to the manufacturer's instructions. The result is shown in FIG. 4.

7.4 The Inhibitory Activity of the Fusion Protein on Tumor Growth in Model Mice is Compared with Those of the Positive Control and Negative Control In this experiment, tumor-bearing mice with xenograft tumor models established by gastric cancer tissue derived from patients (patient-derived xenograft, PDX) are used to determine the anti-tumor effect of the fusion protein. Mice bearing tumor volume of about 100 $mm^3$ are randomly divided into groups, with 4-6 mice in each experimental group. Fifteen days after tumor transplantation, the mice are treated with different proteins and different doses. Tumor volume and body weight changes of mice in each group are monitored during administration. The dosing frequency is 2 times/week, and the monitoring frequency is 2 times/week for continuous 5 weeks. The dosage and administration route are shown in Table 6. Tumor volume measurement: the largest long axis (L) and largest wide axis (W) of the tumor are measured with a vernier caliper, and the tumor volume is calculated according to the following formula: $V=L \times W^2/2$.

TABLE 6

| Sample | SEQ ID NO. | Dosage (mg/kg) | Administration route |
|---|---|---|---|
| Anti-C18.2-hu6V3-Fc | 107 | 10 | Tail vein injection |
| Anti-C18.2-hu19V3-Fc | 109 | 10 | Tail vein injection |
| IgG1 Fc | 91 | 10 | Tail vein injection |

Figure 5:
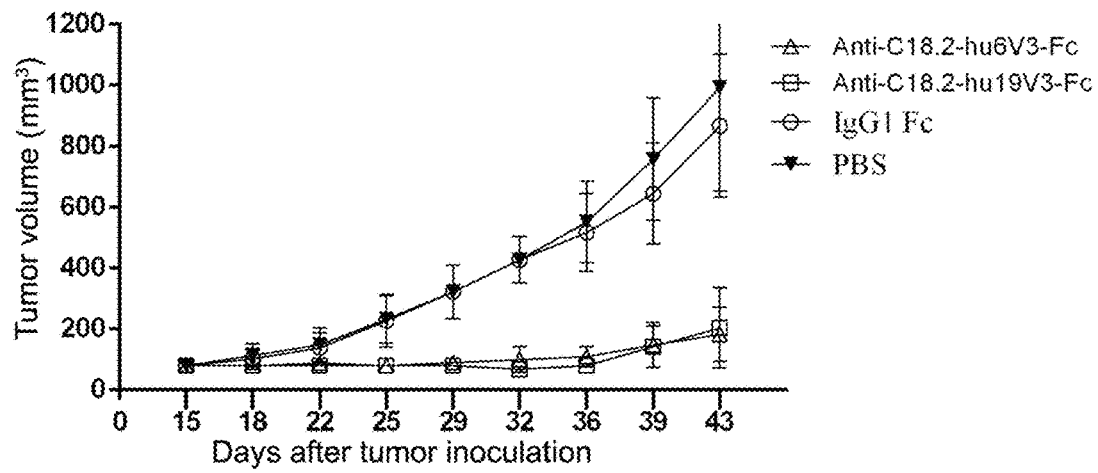
FIG. 5 shows the inhibitory effect of the Anti-C18.2-Fc fusion protein of the present disclosure on tumor growth in mice in vivo.

The results of the experiment are shown in FIG. 5. As time goes on, the tumor volume of mice inoculated with Anti-C18.2-hu6V3-Fc and Anti-C18.2-hu19V3-Fc is well controlled compared to that of the control groups without significant increase. The result indicates that Anti-C18.2-hu6V3-Fc and Anti-C18.2-hu19V3-Fc have obvious tumor inhibition effects.

Embodiment 8: Vector Construction, Expression and Purification of Anti-CLDN18×CD3 Fusion Protein 8.1 Sequence Design of Anti-CLDN18×CD3 Fusion Protein Anti-CLDN18×CD3 fusion protein is a bispecific VHH antibody targeting CLD18A2 and CD3, which is composed of Anti-CLD18A2 and Anti-CD3 VHH: the sequence of anti-CLD18A2 VHH is disclosed in the present disclosure, and the sequence of anti-CD3 VHH is reported in WO2016/180982. Anti-CLD18A2 and Anti-CD3 VHH are linked by a GS sequence (SEQ ID NO.132). To facilitate purification, a C-terminal His-tag is added to Anti-CLDN18×CD3 fusion protein and Anti-CD3 VHH.

8.2 Vector Construction, Expression, and Purification of Anti-CLDN18×CD3 Fusion Protein The sequences of Anti-CLDN18×CD3 fusion protein and Anti-CD3 VHH are optimized and synthesized by General Biosystems (Anhui) Corporation Limited. The XhoI and EcoRI digested products are connected with the expression vector pPIC9 using T4 ligase (Takara), transformed into the competent *E. coli* TOP10F, spread on ampicillin-resistant plates, and cultured overnight in an incubator at 37° C. Clones on the ampicillin-resistant plates are picked, respectively. The plasmids are extracted and sequenced to confirm the correct insertion of the sequence in the pPIC9 vector. The expression plasmid confirmed by sequencing is transformed into *Pichia pastoris* GS115. Recombinant clones are picked from the MD plate, cultured, and induced by methanol for expression. The culture induced overnight is centrifuged at 12000 g for 10 min at 4° C., the supernatant is extracted and purified by Ni column (Bestchrom Biotechnology Co., Ltd.), and the final protein purity is above 90%.

Embodiment 9: Characterisation of the Function of Anti-CLDN18×CD3 Fusion Protein 9.1 Cell Binding Specificity of Anti-CLDN18×CD3 Fusion Protein Jurkat (purchased from the Cell Bank of Committee on Type Culture Collection of Chinese Academy of Sciences) serves as the CD3 positive cell, and the CHO-S-CLD18A2 constructed in Embodiment 1 serves as the CLD18A2 positive cell, to determine the cell-binding activity of the Anti-CLDN18×CD3 fusion protein constructed and expressed in the present disclosure.

Figure 6:
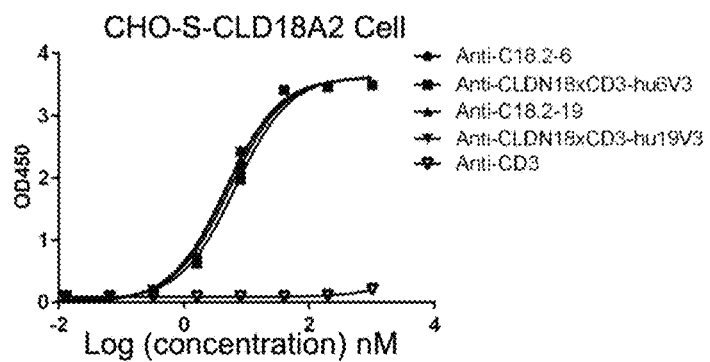
FIG. 6 shows the binding curve of the Anti-CLDN18×CD3 fusion protein of the present disclosure against CHO-S-CLD18A2.
Figure 7:
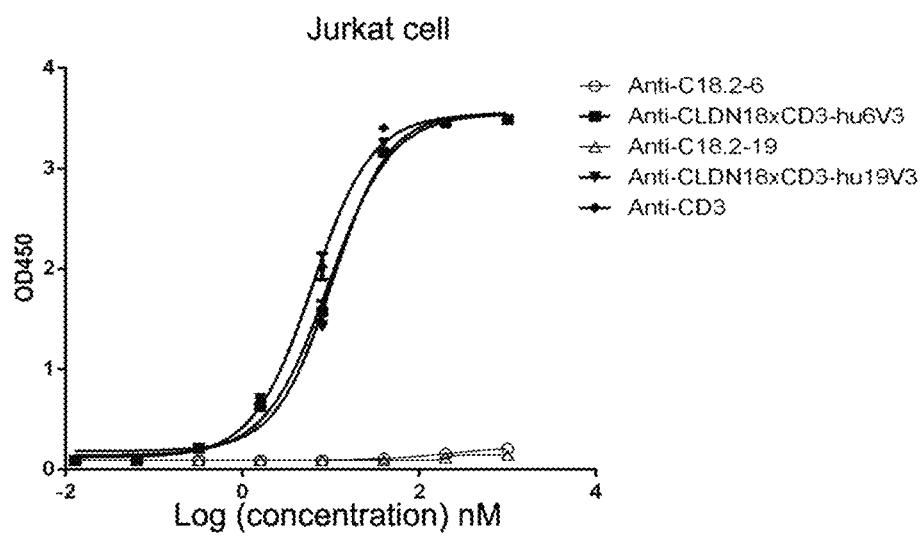
FIG. 7 shows the binding curve of the Anti-CLDN18×CD3 fusion protein of the present disclosure against Jurkat cells.

CHO-S-CLD18A2 and Jurkat cells are plated in 96-well plates at $5 \times 10^5$/ml per well, and blocked with 3% BSA for 1 hat room temperature. The purified Anti-CLDN18×CD3 fusion protein, the Anti-C18.2-6 and Anti-C18.2-19 VHH prepared in Embodiment 4, and the anti-CD3 VHH are diluted in gradients with 1% BSA, and then added into the pre-blocked cells respectively, and then incubated at room temperature for 1 h. The following experimental process is the same as in Embodiment 4.3. GraphPad Prism v5.0 is used for data processing and mapping analysis to evaluate the affinity of Anti-CLDN18×CD3 fusion protein against CHO-S-CLD18A2 and Jurkat cells. The results shown in FIGS. 6-7 indicate that the Anti-CLDN18×CD3 fusion protein has good binding activity with CLD18A2 positive cells and CD3 positive cells. CLD18A2 positive cells binding: the EC50 of Anti-CLDN18×CD3-hu6V3 (SEQ ID NO.133) is 6.50 nM, and the EC50 of Anti-CLDN18×CD3-hu19V3 (SEQ ID NO.134) is 4.60 nM; CD3-positive cells Jurkat binding: the EC50 of Anti-CLDN18×CD3-hu6V3 is 9.39 nM, and the EC50 of Anti-CLDN18×CD3-hu19V3 is 10.36 nM.

9.2 In Vitro Cell Killing Evaluation of Anti-CLDN18×CD3 Fusion Protein

In order to evaluate the cell-killing effect of Anti-CLDN18×CD3 fusion protein, the present disclosure uses T cells (Miao Tong (Shanghai) Biological Technology Co., Ltd.) as effector cells for cytotoxicity test.

Anti-CLDN18×CD3 fusion protein is diluted in gradients, and 50 μl is added to each well. CLD18A2 and CLD18A1 stably transfected cells are washed and re-suspended with 5% FBS 1640 medium (Gibco), and prepared to a cell density of about $2 \times 10^5$/ml. 50 μl per well of the cells was added to the corresponding 96-well plates. Human T lymphocytes from healthy donors are re-suspended in 5% FBS 1640 medium at $1 \times 10^5$ cells per well, so that the E:T ratio is 10:1. After incubating in a 37° C. incubator for 4 h, LDH release is detected with the LDH detection kit (Dojindo Chemical Technology (Shanghai) Co., Ltd.) and carried out according to the manufacturer's instructions. The cell-killing effect of the Anti-CLDN18×CD3 fusion protein is evaluated.

Figure 8:
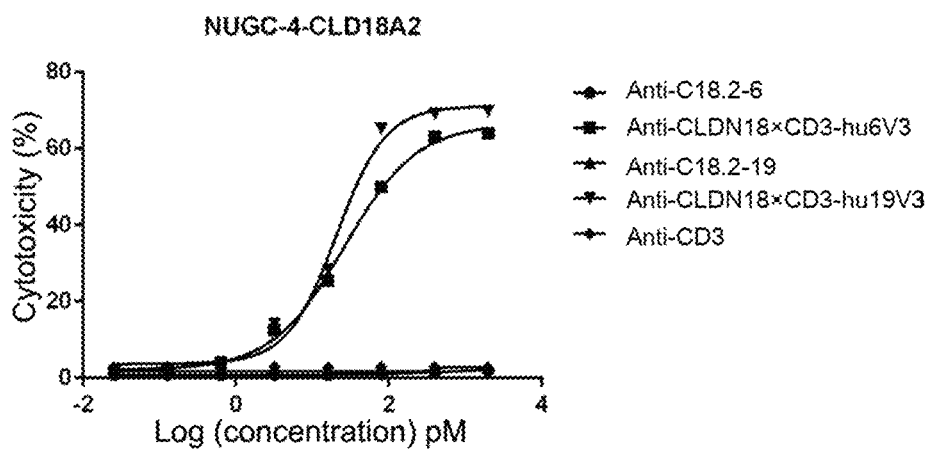
FIG. 8 shows the killing effect of the Anti-CLDN18×CD3 fusion protein of the present disclosure on NUGC-4-CLD18A2 in vitro.
Figure 9:
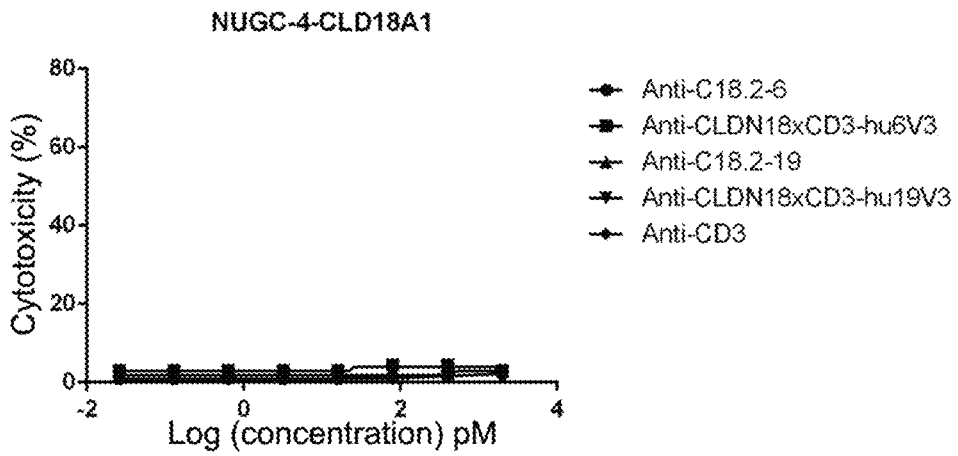
FIG. 9 shows the killing effect of the Anti-CLDN18×CD3 fusion protein of the present disclosure on NUGC-4-CLD18A1 in vitro.

In the in vitro cytotoxicity experiment, Anti-CLDN18×CD3-hu6V3 and Anti-CLDN18×CD3-hu19V3 have remarkable killing effects on NUGC-4-CLD18A2 which highly expresses CLD18A2 (FIG. 8), with EC50 of 26.15 pM and 20.73 pM, respectively. For NUGC-4-CLD18A1 cells, the Anti-CLDN18×CD3 fusion protein has no noticeable killing effect (FIG. 9). The results show that the Anti-CLDN18×CD3 fusion protein has a specific killing effect on NUGC-4-CLD18A2 cells in vitro with the participation of T lymphocytes, and is basically non-toxic to cells that do not express CLD18A2.

9.3 Tumor Inhibiting Activity of Anti-CLDN18×CD3 Fusion Protein

In the present disclosure, tumor-bearing NSG mice with xenograft tumor models established by gastric cancer tissue derived from patients (patient-derived xenograft, PDX) are used to evaluate the tumor-inhibiting effect of the Anti- CLDN18×CD3 fusion protein. When the tumor grows to about 100 mm³, the tumor-bearing mice are randomly divided into groups, with 5 mice per group. The mice are intraperitoneally injected with 2×10⁷ healthy human PBMC cells. One day later, the tumor-bearing mice are intraperitoneally injected with 5 μg (25 μg/ml in 200 μl PBS) Anti-CLDN18×CD3 fusion protein, once a day for 4 weeks. The tumor volume is recorded twice a week.

Figure 10:
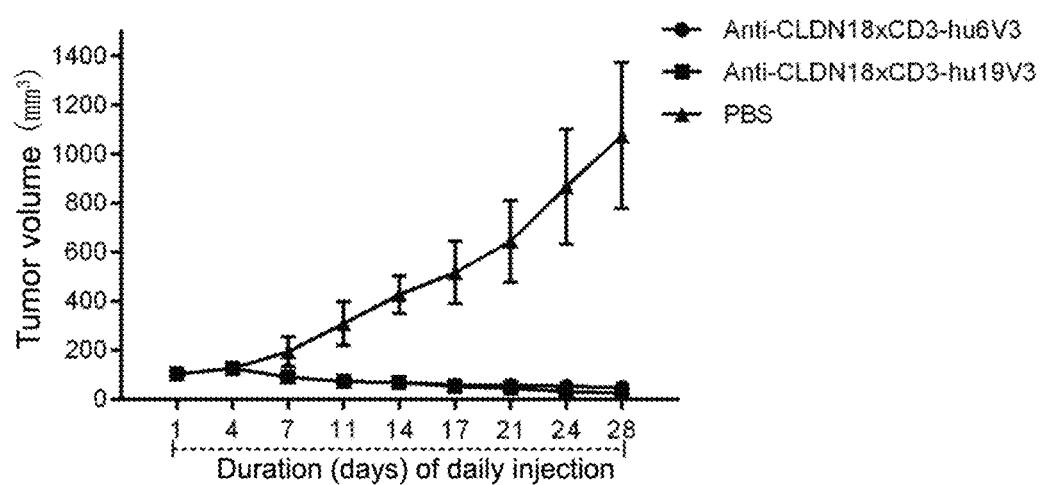
FIG. 10 shows the inhibitory effect of the Anti-CLDN18×CD3 fusion protein of the present disclosure on tumor growth in mice in vivo.

As can be seen from the experimental results in FIG. 10, Anti-CLDN18×CD3-hu6V3 and Anti-CLDN18×CD3-hu19V3 have a noticeable inhibitory effect on the growth of transplanted tumors. As time goes on, the tumor volume of the experimental group gradually decreases.

Embodiment 10: Use of VHH Specifically Targeting CLD18A2 in Chimeric Antigen Receptors The VHH specifically targeting CLD18A2 in the present disclosure is used for the construction of chimeric antigen receptors. Table 7 lists the constructed chimeric antigen receptors and the structures thereof (antigen recognition domain—hinge region—transmembrane region—intracellular signal domain; co-expressed eGFP structure is not listed).

TABLE 7

| Chimeric antigen receptor | Structure | SEQ ID NO |
|---|---|---|
| 28Z | CD8 hinge-CD28a-CD28b-CD3ζ | 135 |
| 28-137Z | CD8 hinge-CD28a-CD28b-CD137-CD3ζ | 136 |
| aC18.2-hu6V3-28Z | VHH(Anti-CLD18A2-hu6V3)-CD8 hinge-CD28a-CD28b-CD3ζ | 137 |
| aC18.2-hu6V3-28-137Z | VHH(Anti-CLD18A2-hu6V3)-CD8 hinge-CD28a-CD28b-CD137-CD3ζ | 138 |
| aC18.2-hu19V3-28Z | VHH(Anti-CLD18A2-hu19V3)-CD8 hinge-CD28a-CD28b-CD3ζ | 139 |
| aC18.2-hu19V3-28-137Z | VHH(Anti-CLD18A2-hu19V3)-CD8 hinge-CD28a-CD28b-CD137-CD3ζ | 140 |

10.1 Construction of Lentiviral Plasmid for VHH Expression

As an example of construction, the present disclosure uses a third-generation self-inactivating lentiviral vector system, which consists of three plasmids, namely, an enveloped plasmid pMD2.G (purchased from AddGene) encoding VSV-G protein, a packaging plasmid psPAX2 (purchased from AddGene) encoding protein Gag/Pol and protein Rev, and a recombinant expression vector encoding the target gene CAR and constructed based on an empty vector pWPT-eGFP (purchased from AddGene). Based on pWPT-eGFP, the present disclosure constructs a universal lentiviral vector for VHH expression to facilitate the insertions of different VHH sequences to construct a complete CAR structure. In addition, the co-expression of target gene CAR and eGFP is realized by T2A in the recombinant expression vector encoding the target gene CAR. T2A is a 2A peptide derived from the Thosea asigna virus. T2A has a "self-splicing" function and thus can realize the co-expression of upstream and downstream genes. The expression of CAR can be detected indirectly by detecting eGFP.

A sequence (SEQ ID NO.141) containing a CD8 signal peptide and a CD8 hinge-CD28a-CD28b-CD3-T2A-egfp is synthesized, in which a multiple cloning site is inserted between the CD8 signal peptide and the CD8 hinge for insertion of VHH or other specific recognition sequences. The synthesized sequence is ligated with the vector pWPT-GFP (AddGene, also digested) by T4 ligase (Takara) through the MluI and salI restriction sites at both ends. The ligation product is transformed into Top10F', and coated on ampicillin-resistant plates. The clones are picked, cultured, and sequenced. The CAR T universal vector pWPT-x-CAR-28Z is constructed. Similarly, a sequence (SEQ ID NO.142) containing a CD8 signal peptide and a CD8 hinge-CD28a-CD28b-CD137-CD3-T2A-egfp is synthesized, in which a multiple cloning site is inserted between the CD8 signal peptide and the CD8 hinge for insertion of VHH or other specific recognition sequences. The synthesized sequence is inserted into the vector pWPT-GFP (also digested) through the MluI and SalI restriction sites at both ends, to construct the CART universal vector pWPT-x-CAR-28-137Z.

10.2 Construction of Anti-CLD18A2 CAR Lentivirus Plasmid

The expression plasmid Anti-C18.2-hu19V3-Fc serves as the template. The primer pair includes a forward primer (SEQ ID NO.143) and a reverse primer (SEQ ID NO.144). PCR amplification is performed with the high-fidelity DNA polymerase GVP8 (General Biosystems (Anhui) Corporation Limited). The PCR product is electrophoresed and recovered by excision from the gel. The CART universal vector pWPT-x-CAR-28Z is double digested with endonucleases NdeI (Takara) and PstI (Takara), and recovered by electrophoresis. The recovered PCR product is connected with the vector using a recombination kit (Novoprotein Scientific Inc). The ligation product is transformed into Top1OF', and spread on ampicillin-resistant plates. The clones are picked, cultured, and sequenced. The Anti-CLD18A2 CAR lentivirus plasmid pWPT-aC18.2-hu19V3-28Z is constructed. Similarly, Anti-CLD18A2 CAR lentivirus plasmid pWPT-aC18.2-hu19V3-28-137Z is constructed by the connection of the recovered PCR product and the vector pWPT-x-CAR-28-137Z double digested with NdeI (Takara) and PstI (Takara). Based on the above operations, pWPT-aC18.2-hu6V3-28Z and pWPT-aC18.2-hu6V3-28-137Z are constructed.

10.3 Transfection of the Plasmid into 293T Packaging Lentivirus

Lentivirus packaging follows conventional methods, which is described as follows: HEK-293T cells (ATCC) cells are planted in a 10 cm culture dish at a density of 5×10⁶ cells, and cultured in an incubator (37° C., 5% CO₂) overnight. The medium is DMEM (Gibco) containing 10% fetal bovine serum (Gibco). The culture medium is replaced with serum-free DMEM about 2 hours before transfection. During cell transfection, plasmids psPAX2 and pMD2.0G (providing viral membrane protein and structural protein) are also required in addition to lentiviral plasmids expressing CAR. 5 μg of the lentiviral plasmid with the target sequence CAR or the empty vector, 3.75 μg of psPAX2, and 1.25 μg of pMD2.0G are used. During transfection, the mixture of the above three plasmids is added to 500 μL MEM medium, and 25 μL Lipofectamine 2000 transfection reagent (Thermo Fisher) is added to 500 μL MEM medium in another mini-centrifuge tube. Then, the diluted transfection reagent is added to the top of the diluted plasmid and mixed well. After incubating at room temperature for 20 min, the plasmid and transfection reagent mixture are added to a 10 cm culture dish, after shaking and mixing well, and placed in an incubator at 37° C. After 6 hours, the medium is replaced with a DMEM medium containing 10% fetal bovine serum. After 3 days of cell transfection, the virus is harvested. The culture supernatant containing the virus is transferred into a centrifuge tube for centrifuging at 1500 rpm under 4° C. for 5 min. Cells are removed, and then the culture medium containing virus is filtered, dispensed, and frozen at −80° C. for storage. HEK-293T cells are inoculated in DMEM containing 10% fetal bovine serum at a cell density of $1\times10^5$/mL and incubated in a 96-well plate at 100 µL/well overnight (37° C., 5% $CO_2$). On the next day, discarding 50 µL/well of the culture supernatant, and adding 50 µL/well of the above-mentioned fresh culture medium (containing polybrene at a final concentration of 6 µg/mL), and incubating for 30 min (37° C., 5% $CO_2$). 10 µL/well of the virus stock solution was added and incubated at 37° C. with 5% $CO_2$. After 48 hours of infection, eGFP is detected by flow cytometry. The number of cells with a positive rate of 5-20% is appropriate, and the titer is calculated to be about $2\times10^6$ U/mL.

Embodiment 11: CAR-T Cells Specifically Targeting CLD18A2

11.1 Preparation of aC18.2-CAR-T

Human peripheral blood mononuclear cells (Miao Tong (Shanghai) Biological Technology Co., Ltd.) are obtained from healthy human peripheral blood by density gradient centrifugation, and sorted by CD3 MicroBeads (MiltenyiBiotec GmbH) according to the instructions. Quantum007 lymphocyte medium (purchased from PAA Laboratories GmbH) is added at a density of approximately $1\times10^6$/mL for culture, mixed with Dynabeads™ Human T-Activator CD3/CD28 (Thermofisher) at a cell-magnetic bead ratio of 1:1, and recombinant human IL-2 (Novoprotein Scientific Inc) is added with a final concentration of 100 U/mL to stimulate the culture for 24 h. Then, the T cells are infected with the above recombinant lentivirus (Embodiment 10.3) at MOI≈5. The infected cells are passaged at a density of $5\times10^5$/mL every other day, and recombinant human IL-2 with a final concentration of 100 U/mL is added into the lymphocyte medium. Flow cytometry is performed on the 8th day of culture. Since eGFP is co-expressed with CAR, the positive cells where eGFP is detectable are considered positive cells that express the chimeric antigen receptors. Uninfected T cells serve as a negative control. The positive rate of T cells infected with viruses expressing different chimeric antigen receptors is about 66.4%.

11.2 Killing Experiment of aC18.2-CAR-T

The killing effect of different aC18.2-CAR-T cells on NUGC-4-CLD18A2 cells and NUGC-4-CLD18A1 cells (CLD18A2-negative cell line) in vitro is observed. The E:T ratios are set to 3:1, 1:1, and 1:3, respectively. The number of target cells is 10000/well. Each group contains 5 repeated wells, and the average value of the 5 repeated wells is calculated. After 16 hours of co-culture, the LDH content in the supernatant is measured by the LDH detection kit (Dojindo Chemical Technology (Shanghai) Co., Ltd.), to evaluate the killing effect. Results in Table 8 show that when the E:T ratio is 3:1, the specific aC18.2-CAR-T cells are effective in killing CLD18A2-positive cells, but hardly effective in killing CLD18A2-negative cells. The above results show that aC18.2-CAR-T can specifically kill CLD18A2-positive cells, and the killing effect is positively correlated with the E:T ratio.

TABLE 8

| Cytotoxicity (average) % | NUGC-4-CLD18A2 | | | NUGC-4-CLD18A1 | | |
|---|---|---|---|---|---|---|
| E:T ratio | 1:3 | 1:1 | 3:1 | 1:3 | 1:1 | 3:1 |
| aC18.2-hu6V3-28Z | 16.1 | 29.4 | 43.2 | 4.2 | 5.3 | 8.1 |
| aC18.2-hu6V3-28-137Z | 25.6 | 53.3 | 70.5 | 4.6 | 7.8 | 9.4 |
| aC18.2-hu19V3-28Z | 17.2 | 30.5 | 42.6 | 3.2 | 5.5 | 7.7 |
| aC18.2-hu19V3-28-137Z | 27.9 | 58.1 | 79.3 | 5.6 | 8.3 | 10.1 |
| 28Z (MOCK) | 3.4 | 4.5 | 6.1 | 3.3 | 5.1 | 5.9 |
| 28-137Z (MOCK) | 3.8 | 4.7 | 6.8 | 3.9 | 4.3 | 5.5 |

11.3 In Vitro Cytokine Release

Figure 11:
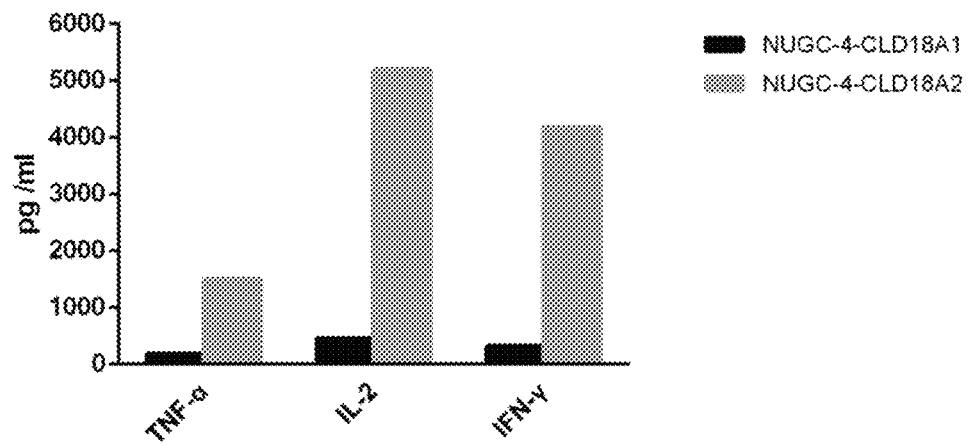
FIG. 11 shows the results of in vitro cytokine release after the NUGC-4-CLD18A2 and NUGC-4-CLD18A1 treated with aC18.2-CAR-T cells of the present disclosure.

The CLD18A2-positive cells NUGC-4-CLD18A2 and aC18.2-CAR-T cells are co-cultured at a ratio of 1:1. After incubation for 24 h, the culture supernatants are collected, and cytokines are detected by IL-2 (R&D Systems, Inc.), TNF-α (R&D Systems, Inc.), and IFN-γ (R&D Systems, Inc.) according to kit instructions. Results in FIG. 11 show that in NUGC-4-CLD18A2, the secretion of cytokines such as IL-2, TNF-α, IFN-γ during aC18.2-CAR-T co-incubation is significantly higher than that of negative cells NUGC-4-CLD18A1.

11.4 In Vivo Pharmacodynamic Study of aC18.2-CAR-T

Figure 12:
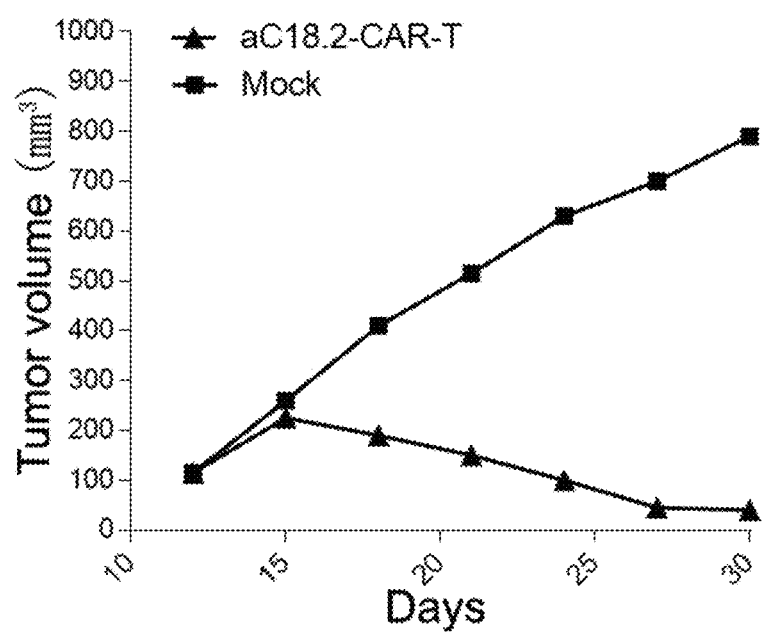
FIG. 12 shows the inhibitory effect of the aC18.2-CAR-T cells of the present disclosure on tumor growth in mice in vivo.

A subcutaneous transplanted tumor model is established based on NUGC-4-CLD18A2. NOD/SCID mice inoculated subcutaneously with $3\times10^6$ NUGC-4-CLD18A2. When the average tumor volume of mice reaches 100-150 mm³, 100 mg/kg of cyclophosphamide is injected intraperitoneally to eliminate the immune cells of NOD/SCID mice, so that the adoptively transferred transgenic T lymphocytes can better exert the anti-tumor function. On the next day, $1.0\times10^7$ of aC18.2-CAR-T cells aC18.2-hu19V3-28-137Z are infused via the tail vein. At the same time, the Mock group expressing 28-137Z serves as a control to observe and measure the growth of the subcutaneously transplanted tumor. Results in FIG. 12 shows that aC18.2-CAR-T cells can significantly inhibit the growth of NUGC-4-CLD18A2 transplanted tumors.

In summary, the present disclosure effectively overcomes various shortcomings and has high industrial utilization value.

The above-mentioned embodiments are only used for exemplarily describing the principle and effects of the present disclosure and do not limit the present disclosure. Modifications or variations of the above-described embodiments may be made by those skilled in the art without departing from the spirit and scope of the present disclosure. Therefore, all equivalent modifications or changes made by those skilled in the art without departing from the spirit and technical concept disclosed by the present disclosure shall still be covered by the claims of the present disclosure.

The invention claimed is:

1. An anti-CLD18A2 VHH, comprising:
   a complementarity determining region CDR having CDR1, CDR2, and CDR3, wherein
   CDR1 has an amino acid sequence comprising one of SEQ ID NOs. 4-11,
   CDR2 has an amino acid sequence comprising one of SEQ ID NOs. 19-26, and
   CDR3 has an amino acid sequence comprising one of SEQ ID NOs. 33-39.

2. The anti-CLD18A2 VHH according to claim 1, wherein
   (1) CDR1 has an amino acid sequence comprising SEQ ID NO. 4, CDR2 has an amino acid sequence comprising SEQ ID NO. 19, and CDR3 has an amino acid sequence comprising SEQ ID NO. 33; or
   (2) CDR1 has an amino acid sequence comprising SEQ ID NO. 5, CDR2 has an amino acid sequence comprising SEQ ID NO. 20, and CDR3 has an amino acid sequence comprising SEQ ID NO. 34; or
   (3) CDR1 has an amino acid sequence comprising SEQ ID NO. 6, CDR2 has an amino acid sequence comprising SEQ ID NO. 21, and CDR3 has an amino acid sequence comprising SEQ ID NO. 35; or
   (4) CDR1 has an amino acid sequence comprising SEQ ID NO. 7, CDR2 has an amino acid sequence comprising SEQ ID NO. 22, and CDR3 has an amino acid sequence comprising SEQ ID NO. 36; or
   (5) CDR1 has an amino acid sequence comprising SEQ ID NO. 8, CDR2 has an amino acid sequence comprising SEQ ID NO. 23, and CDR3 has an amino acid sequence comprising SEQ ID NO. 37; or
   (6) CDR1 has an amino acid sequence comprising SEQ ID NO. 9, CDR2 has an amino acid sequence comprising SEQ ID NO. 24, and CDR3 has an amino acid sequence comprising SEQ ID NO. 38; or
   (7) CDR1 has an amino acid sequence comprising SEQ ID NO. 10, CDR2 has an amino acid sequence comprising SEQ ID NO. 25, and CDR3 has an amino acid sequence comprising SEQ ID NO. 36; or
   (8) CDR1 has an amino acid sequence comprising SEQ ID NO. 11, CDR2 has an amino acid sequence comprising SEQ ID NO. 26, and CDR3 has an amino acid sequence comprising SEQ ID NO. 39.

3. The anti-CLD18A2 VHH according to claim 1, further comprising:
   a frame region FR having FR1, FR2, FR3, and FR4, wherein
   (1) FR1 has an amino acid sequence comprising SEQ ID NO. 1, FR2 has an amino acid sequence comprising SEQ ID NO. 12, FR3 has an amino acid sequence comprising SEQ ID NO. 27, and FR4 has an amino acid sequence comprising SEQ ID NO. 40; or
(2) FR1 has an amino acid sequence comprising SEQ ID NO. 2, FR2 has an amino acid sequence comprising SEQ ID NO. 13, FR3 has an amino acid sequence comprising SEQ ID NO. 28, and FR4 has an amino acid sequence comprising SEQ ID NO. 41; or
(3) FR1 has an amino acid sequence comprising SEQ ID NO. 3, FR2 has an amino acid sequence comprising SEQ ID NO. 14, FR3 has an amino acid sequence comprising SEQ ID NO. 29, and FR4 has an amino acid sequence comprising SEQ ID NO. 41; or
(4) FR1 has an amino acid sequence comprising SEQ ID NO. 1, FR2 has an amino acid sequence comprising SEQ ID NO. 15, FR3 has an amino acid sequence comprising SEQ ID NO. 30, and FR4 has an amino acid sequence comprising SEQ ID NO. 41; or
(5) FR1 has an amino acid sequence comprising SEQ ID NO. 2, FR2 has an amino acid sequence comprising SEQ ID NO. 16, FR3 has an amino acid sequence comprising SEQ ID NO. 31, and FR4 has an amino acid sequence comprising SEQ ID NO. 41; or
(6) FR1 has an amino acid sequence comprising SEQ ID NO. 2, FR2 has an amino acid sequence comprising SEQ ID NO. 13, FR3 has an amino acid sequence comprising SEQ ID NO. 31, and FR4 has an amino acid sequence comprising SEQ ID NO. 41; or
(7) FR1 has an amino acid sequence comprising SEQ ID NO. 1, FR2 has an amino acid sequence comprising SEQ ID NO. 17, FR3 has an amino acid sequence comprising SEQ ID NO. 30, and FR4 has an amino acid sequence comprising SEQ ID NO. 41; or
(8) FR1 has an amino acid sequence comprising SEQ ID NO. 2, FR2 has an amino acid sequence comprising SEQ ID NO. 18, FR3 has an amino acid sequence comprising SEQ ID NO. 32, and FR4 has an amino acid sequence comprising SEQ ID NO. 41.

4. The anti-CLD18A2 VHH according to claim 1, wherein an amino acid sequence of the anti-CLD18A2 VHH comprises:
a) an amino acid sequence comprising one of SEQ ID NOs. 42-49; or
b) an amino acid sequence with at least 80% sequence identity with one of SEQ ID NOs. 42-49 and has a function of the amino acid sequence defined in a).

5. The anti-CLD18A2 VHH according to claim 1, wherein the anti-CLD18A2 VHH is a humanized antibody, and an amino acid sequence of an anti-CLD18A2 humanized antibody comprises one of SEQ ID NOs. 67-90.

6. A fusion protein of an anti-CLD18A2 VHH, comprising
a first domain of the anti-CLD18A2 VHH according to claim 1, and
a second domain for prolonging the half-life in vivo and/or having a binding effect on effector cells.

7. The fusion protein according to claim 6, wherein
the second domain comprises one or more of serum albumin fragment, polyethylene glycol fragment, and human serum albumin binding VHH (HSA-binding VHH); and/or,
the second domain comprises an immunoglobulin Fc region, and the immunoglobulin Fc region is selected from a human immunoglobulin Fc region; and/or,
the second domain comprises a molecule that has an affinity for CD3 present on T cells and/or is capable of binding to CD3 present on T cells.

8. The fusion protein according to claim 7, wherein
the human immunoglobulin Fc region includes a mutation for altering an Fc-mediated effector function, and the effector function includes one or more of CDC activity, ADCC activity, and ADCP activity; and/or,
the immunoglobulin is selected from one or more of IgG, IgA1, IgA2, IgD, IgE, and IgM, and the IgG is selected from one or more of IgG1, IgG2, IgG3, and IgG4 subtypes; and/or,
an amino acid sequence of the immunoglobulin Fc region is selected from one of SEQ ID NOs. 91-95; and/or,
a connecting peptide is provided between the first domain and the second domain, wherein
the connecting peptide is selected from a flexible polypeptide chain composed of alanine and/or serine and/or glycine, and
a length of the connecting peptide is 3-40 amino acids.

9. An isolated polynucleotide, which encodes the anti-CLD18A2 VHH according to claim 1 or a fusion protein of the anti-CLD18A2 VHH, wherein
the fusion protein comprises a first domain of the anti-CLD18A2 VHH, and a second domain for prolonging the half-life in vivo and/or having a binding effect on effector cells.

10. An expression vector, which comprises the isolated polynucleotide according to claim 9.

11. An antibody expression system, which comprises an expression vector including the isolated polynucleotide according to claim 9 or incorporating the isolated polynucleotide according to claim 9 as an exogenous polynucleotide in a genome.

12. A method for preparing an anti-CLD18A2 VHH or a fusion protein of the anti-CLD18A2 VHH, comprising the following steps:
culturing the antibody expression system according to claim 11 under conditions suitable for expressing the antibody, thereby expressing the antibody, and purifying and isolating the antibody; wherein
the anti-CLD18A2 VHH comprises a complementarity determining region CDR having CDR1, CDR2, and CDR3, wherein
CDR1 has an amino acid sequence comprising one of SEQ ID NOs. 4-11,
CDR2 has an amino acid sequence comprising one of SEQ ID NOs. 19-26, and
CDR3 has an amino acid sequence comprising one of SEQ ID NOs. 33-39; wherein
the fusion protein comprises a first domain of the anti-CLD18A2 VHH, and a second domain for prolonging the half-life in vivo and/or having a binding effect on effector cells.

13. An immunoconjugate, wherein the immunoconjugate comprises the anti-CLD18A2 VHH according to claim 1 or a fusion protein of an anti-CLD18A2 VHH,
the immunoconjugate further comprises a coupling portion, and the coupling portion includes one or more of a detectable label, a cytotoxin, a radioisotope, and a biologically active protein; wherein
the fusion protein comprises a first domain of the anti-CLD18A2 VHH, and a second domain for prolonging the half-life in vivo and/or having a binding effect on effector cells.

14. A detection kit, which comprises an anti-CLD18A2 VHH, a fusion protein of an anti-CLD18A2 VHH, or an immunoconjugate, wherein the anti-CLD18A2 VHH comprises a complementarity determining region CDR having CDR1, CDR2, and CDR3, wherein
CDR1 has an amino acid sequence comprising one of SEQ ID NOs. 4-11,
CDR2 has an amino acid sequence comprising one of SEQ ID NOs. 19-26, and
CDR3 has an amino acid sequence comprising one of SEQ ID NOs. 33-39;
the fusion protein comprises a first domain of the anti-CLD18A2 VHH, and a second domain for prolonging the half-life in vivo and/or having a binding effect on effector cells; and
the immunoconjugate comprises the anti-CLD18A2 VHH or the fusion protein of an anti-CLD18A2 VHH,
the immunoconjugate further comprises a coupling portion, and
the coupling portion includes one or more of a detectable label, a cytotoxin, a radioisotope, and a biologically active protein.

15. A pharmaceutical composition, which comprises an anti-CLD18A2 VHH, a fusion protein of an anti-CLD18A2 VHH, or an immunoconjugate, wherein
the anti-CLD18A2 VHH comprises a complementarity determining region CDR having CDR1, CDR2, and CDR3, wherein
CDR1 has an amino acid sequence comprising one of SEQ ID NOs. 4-11,
CDR2 has an amino acid sequence comprising one of SEQ ID NOs. 19-26, and
CDR3 has an amino acid sequence comprising one of SEQ ID NOs. 33-39;
the fusion protein comprises a first domain of the anti-CLD18A2 VHH, and a second domain for prolonging the half-life in vivo and/or having a binding effect on effector cells; and
the immunoconjugate comprises the anti-CLD18A2 VHH or the fusion protein of the anti-CLD18A2 VHH,
the immunoconjugate further comprises a coupling portion, and
the coupling portion includes one or more of a detectable label, a cytotoxin, a radioisotope, and a biologically active protein.

16. The pharmaceutical composition according to claim 15, further comprising a pharmaceutically acceptable carrier.

17. An isolated polypeptide, which comprises an antigen recognition domain, a hinge region, a transmembrane region, and an intracellular signal domain, wherein
the antigen recognition domain includes the VHH according to claim 1.

18. A cell, which comprises a polypeptide according to claim 17 that is membrane-bound, wherein the cell is a T lymphocyte, a macrophage and/or a NK cell.

19. A method for diagnosing, treating, or preventing diseases associated with cells expressing CLD18A2, comprising:
administrating an effective amount of the anti-CLD18A2 VHH of claim 1, a fusion protein of the anti-CLD18A2 VHH, an immunoconjugate, or a pharmaceutical composition to a subject in need thereof, wherein
the fusion protein comprises a first domain of the anti-CLD18A2 VHH, and a second domain for prolonging the half-life in vivo and/or having a binding effect on effector cells; and
the immunoconjugate comprises the anti-CLD18A2 VHH or the fusion protein of the anti-CLD18A2 VHH,
the immunoconjugate further comprises a coupling portion, and
the coupling portion includes one or more of a detectable label, a cytotoxin, a radioisotope, and a biologically active protein,
the pharmaceutical composition comprises the anti-CLD18A2 VHH, the fusion protein of the anti-CLD18A2 VHH, or the immunoconjugate.

20. The method according to claim 19, wherein the diseases associated with cells expressing CLD18A2 is selected from a tumor, and the tumor is selected from the group consisting of gastric cancer, esophageal cancer, pancreatic cancer, lung cancer, ovarian cancer, colon cancer, liver cancer, head and neck cancer, and gallbladder cancer.

* * * * *

SEQUENCE LISTING

<160> NUMBER OF SEQ ID NOS: 144

<210> SEQ ID NO 1
<211> LENGTH: 25
<212> TYPE: PRT
<213> ORGANISM: Artificial Sequence
<220> FEATURE:
<223> OTHER INFORMATION: Amino acid sequence of FR1

<400> SEQUENCE: 1

Gln Leu Gln Leu Val Glu Ser Gly Gly Gly Leu Val Gln Pro Gly Gly
1               5                   10                  15
Ser Leu Arg Leu Ser Cys Ala Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Amino acid sequence of FR1

<400> SEQUENCE: 2

Gln Val Gln Leu Val Glu Ser Gly Gly Gly Leu Val Gln Pro Gly Gly
1               5                   10                  15
Ser Leu Arg Leu Ser Cys Ala Ala Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: Amino acid sequence of FR1

<400> SEQUENCE: 3

Gln Val Gln Leu Val Glu Ser Gly Gly Gly Leu Val Gln Pro Gly Gly
1               5                   10                  15
Ser Leu Arg Leu Ser Cys Thr Ala Ser
            20                  25

<210> SEQ ID NO 4
<211> LENGTH: 8
<212> TYPE: PRT
<213> ORGANISM: Artificial Sequence
<220> FEATURE:
<223> OTHER INFORMATION: Amino acid sequence of CDR1

<400> SEQUENCE: 4

Gly Gly Ile Phe Ser Ile Gly Val
1               5

<210> SEQ ID NO 5
<211> LENGTH: 8
<212> TYPE: PRT
<213> ORGANISM: Artificial Sequence
<220> FEATURE:
<223> OTHER INFORMATION: Amino acid sequence of CDR1

<400> SEQUENCE: 5

Gly Ser Ile Phe Leu Ile Asn Ala
1               5

<210> SEQ ID NO 6
<211> LENGTH: 8

```
<212> TYPE: PRT
<213> ORGANISM: Artificial Sequence
<220> FEATURE:
<223> OTHER INFORMATION: Amino acid sequence of CDR1

<400> SEQUENCE: 6

Gly Ser Ile Phe Arg Ile Asp Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Amino acid sequence of CDR1

<400> SEQUENCE: 7

Gly Val Asp Ile Ser Ser Asp Val
1               5

<210> SEQ ID NO 8
<211> LENGTH: 8
<212> TYPE: PRT
<213> ORGANISM: Artificial Sequence
<220> FEATURE:
<223> OTHER INFORMATION: Amino acid sequence of CDR1

<400> SEQUENCE: 8

Gly Ser Ile Phe Ser Ile Asn Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Amino acid sequence of CDR1

<400> SEQUENCE: 9

Gly Ser Ile Phe Met Ile Asn Val
1               5

<210> SEQ ID NO 10
<211> LENGTH: 7
<212> TYPE: PRT
<213> ORGANISM: Artificial Sequence
<220> FEATURE:
<223> OTHER INFORMATION: Amino acid sequence of CDR1

<400> SEQUENCE: 10

Gly Glu Ile Ser Ser Asp Ala
1               5

<210> SEQ ID NO 11
<211> LENGTH: 8
<212> TYPE: PRT
<213> ORGANISM: Artificial Sequence
<220> FEATURE:
<223> OTHER INFORMATION: Amino acid sequence of CDR1

<400> SEQUENCE: 11

Gly Ser Ile Phe Ser Ile Pro Val
1               5

<210> SEQ ID NO 12
<211> LENGTH: 17
<212> TYPE: PRT
```

<213> ORGANISM: Artificial Sequence
<220> FEATURE:
<223> OTHER INFORMATION: Amino acid sequence of FR2

<400> SEQUENCE: 12

Met Gly Trp Tyr Arg Gln Ala Pro Gly Lys Gln Arg Glu Leu Val Ala
1               5                   10                  15
Thr

<210> SEQ ID NO 13
<211> LENGTH: 17
<212> TYPE: PRT
<213> ORGANISM: Artificial Sequence
<220> FEATURE:
<223> OTHER INFORMATION: Amino acid sequence of FR2

<400> SEQUENCE: 13

Met Gly Trp Tyr Arg Gln Ala Pro Gly Lys Gln Arg Glu Leu Val Ala
1               5                   10                  15
Val

<210> SEQ ID NO 14
<211> LENGTH: 17
<212> TYPE: PRT
<213> ORGANISM: Artificial Sequence
<220> FEATURE:
<223> OTHER INFORMATION: Amino acid sequence of FR2

<400> SEQUENCE: 14

Met His Trp Tyr Arg Gln Ala Pro Gly Lys Gln Arg Glu Leu Val Ala
1               5                   10                  15
Ser

<210> SEQ ID NO 15
<211> LENGTH: 17
<212> TYPE: PRT
<213> ORGANISM: Artificial Sequence
<220> FEATURE:
<223> OTHER INFORMATION: Amino acid sequence of FR2

<400> SEQUENCE: 15

Met Ala Trp Tyr Arg Gln Ala Pro Gly Lys Gln Arg Glu Phe Val Ser
1               5                   10                  15
Gly

<210> SEQ ID NO 16
<211> LENGTH: 17
<212> TYPE: PRT
<213> ORGANISM: Artificial Sequence
<220> FEATURE:
<223> OTHER INFORMATION: Amino acid sequence of FR2

<400> SEQUENCE: 16

Met Gly Trp Tyr Arg Gln Ala Pro Gly Lys Gln Arg Glu Leu Val Ala
1               5                   10                  15
Ala

<210> SEQ ID NO 17
<211> LENGTH: 17
<212> TYPE: PRT
<213> ORGANISM: Artificial Sequence
<220> FEATURE:
<223> OTHER INFORMATION: Amino acid sequence of FR2

```
<400> SEQUENCE: 17

Met Ala Trp Tyr Arg Gln Ala Pro Gly Lys Gln Arg Glu Leu Val Ala
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: Amino acid sequence of FR2

<400> SEQUENCE: 18

Met Thr Trp Tyr Arg Gln Ala Leu Gly Lys Glu Arg Glu Phe Val Ala
1               5                   10                  15

Gly

<210> SEQ ID NO 19
<211> LENGTH: 7
<212> TYPE: PRT
<213> ORGANISM: Artificial Sequence
<220> FEATURE:
<223> OTHER INFORMATION: Amino acid sequence of CDR2

<400> SEQUENCE: 19

Ile Thr Ser Arg Gly Ser Thr
1               5

<210> SEQ ID NO 20
<211> LENGTH: 7
<212> TYPE: PRT
<213> ORGANISM: Artificial Sequence
<220> FEATURE:
<223> OTHER INFORMATION: Amino acid sequence of CDR2

<400> SEQUENCE: 20

Ile Thr Arg Gly Gly Ser Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Amino acid sequence of CDR2

<400> SEQUENCE: 21

Ile Thr Pro Ser Gly Ile Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Amino acid sequence of CDR2

<400> SEQUENCE: 22

Leu Thr Arg Gly Gly Ser Ile
1               5

<210> SEQ ID NO 23
<211> LENGTH: 8
<212> TYPE: PRT
<213> ORGANISM: Artificial Sequence
```

```
<220> FEATURE:
<223> OTHER INFORMATION: Amino acid sequence of CDR2

<400> SEQUENCE: 23

Ile Thr Phe Gly Gly Gly Ser Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Amino acid sequence of CDR2

<400> SEQUENCE: 24

Ile Thr Arg Gly Ala Ser Thr
1               5

<210> SEQ ID NO 25
<211> LENGTH: 7
<212> TYPE: PRT
<213> ORGANISM: Artificial Sequence
<220> FEATURE:
<223> OTHER INFORMATION: Amino acid sequence of CDR2

<400> SEQUENCE: 25

Met Thr Arg Gly Gly Ser Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Amino acid sequence of CDR2

<400> SEQUENCE: 26

Ile Ser Lys Gly Gly Thr Ser
1               5

<210> SEQ ID NO 27
<211> LENGTH: 38
<212> TYPE: PRT
<213> ORGANISM: Artificial Sequence
<220> FEATURE:
<223> OTHER INFORMATION: Amino acid sequence of FR3

<400> SEQUENCE: 27

Asn Tyr Ala Asp Ser Val Lys Gly Arg Phe Thr Ile Ser Gly Asp Asn
1               5                   10                  15

Ala Lys Asn Thr Val Tyr Leu Gln Met Asn Asn Leu Lys Pro Glu Asp
            20                  25                  30

Thr Ala Val Tyr Tyr Cys
        35

<210> SEQ ID NO 28
<211> LENGTH: 38
<212> TYPE: PRT
<213> ORGANISM: Artificial Sequence
<220> FEATURE:
<223> OTHER INFORMATION: Amino acid sequence of FR3

<400> SEQUENCE: 28

Asn Tyr Thr Asp Ser Val Lys Gly Arg Phe Thr Ile Ser Arg Asp Asn
1               5                   10                  15
```

```
Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 29
<211> LENGTH: 38
<212> TYPE: PRT
<213> ORGANISM: Artificial Sequence
<220> FEATURE:
<223> OTHER INFORMATION: Amino acid sequence of FR3

<400> SEQUENCE: 29

His Tyr Ala Asp Ser Val Lys Gly Arg Phe Thr Ile Ser Arg Asp Ile
1               5                   10                  15

Ala Lys Lys Met Gln Tyr Leu Gln Met Asn Ser Leu Lys Pro Glu Asp
            20                  25                  30

Thr Ala Val Tyr Tyr Cys
        35

<210> SEQ ID NO 30
<211> LENGTH: 38
<212> TYPE: PRT
<213> ORGANISM: Artificial Sequence
<220> FEATURE:
<223> OTHER INFORMATION: Amino acid sequence of FR3

<400> SEQUENCE: 30

Asn Tyr Ala Asp Ser Val Lys Gly Arg Phe Thr Ile Ser Arg Asp Phe
1               5                   10                  15

Ala Lys Asn Thr Val Asp Leu Gln Met Asn Ser Leu Lys Pro Glu Asp
            20                  25                  30

Thr Ala Val Tyr Tyr Cys
        35

<210> SEQ ID NO 31
<211> LENGTH: 38
<212> TYPE: PRT
<213> ORGANISM: Artificial Sequence
<220> FEATURE:
<223> OTHER INFORMATION: Amino acid sequence of FR3

<400> SEQUENCE: 31

Asn Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys
        35

<210> SEQ ID NO 32
<211> LENGTH: 38
<212> TYPE: PRT
<213> ORGANISM: Artificial Sequence
<220> FEATURE:
<223> OTHER INFORMATION: Amino acid sequence of FR3

<400> SEQUENCE: 32

Asn Tyr Ala Asp Ser Val Lys Gly Arg Phe Thr Val Ser Arg Asp Asn
1               5                   10                  15

Ala Lys Asn Thr Val Tyr Leu Gln Met Asn Ser Leu Lys Ser Glu Asp
            20                  25                  30
```

Thr Ala Val Tyr Tyr Cys
        35

<210> SEQ ID NO 33
<211> LENGTH: 15
<212> TYPE: PRT
<213> ORGANISM: Artificial Sequence
<220> FEATURE:
<223> OTHER INFORMATION: Amino acid sequence of CDR3

<400> SEQUENCE: 33

Tyr Ala Asp Leu Ile Arg Pro Gly Asp Phe Tyr Gly Met Asp Tyr
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Amino acid sequence of CDR3

<400> SEQUENCE: 34

Asn Ala Asp Leu Asn Leu Arg Ser Asp Pro Phe Lys Trp Tyr Thr Phe
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Amino acid sequence of CDR3

<400> SEQUENCE: 35

Asn Ala His Leu Val Lys Val Gly Gly Val Trp Ser Asp Glu Tyr
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: Amino acid sequence of CDR3

<400> SEQUENCE: 36

Asn Ala Glu Ile Tyr Thr Gly Thr Phe Tyr Pro Arg Ser Tyr
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Amino acid sequence of CDR3

<400> SEQUENCE: 37

Asn Ala Asp Leu Leu Val Gly Gly Phe Pro Arg Arg Asn Val Tyr
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Amino acid sequence of CDR3

```
<400> SEQUENCE: 38

Asn Ala Asp Leu Asn Leu Ala Ser Asp Pro Phe Lys Trp Tyr Thr Tyr
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Amino acid sequence of CDR3

<400> SEQUENCE: 39

Asn Ala Gln Ala Ser Ser Phe Gly Trp Met Pro Leu Ser Asp Tyr
1               5                   10                  15

<210> SEQ ID NO 40
<211> LENGTH: 11
<212> TYPE: PRT
<213> ORGANISM: Artificial Sequence
<220> FEATURE:
<223> OTHER INFORMATION: Amino acid sequence of FR4

<400> SEQUENCE: 40

Trp Gly Lys Gly Thr Leu Val Thr Val Ser Ser
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Amino acid sequence of FR4

<400> SEQUENCE: 41

Trp Gly Gln Gly Thr Gln Val Thr Val Ser Ser
1               5                   10

<210> SEQ ID NO 42
<211> LENGTH: 121
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 42

Gln Leu Gln Leu Val Glu Ser Gly Gly Leu Val Gln Pro Gly Gly
1               5                   10                  15

Ser Leu Arg Leu Ser Cys Ala Ala Ser Gly Gly Ile Phe Ser Ile Gly
                20                  25                  30

Val Met Gly Trp Tyr Arg Gln Ala Pro Gly Lys Gln Arg Glu Leu Val
            35                  40                  45

Ala Thr Ile Thr Ser Arg Gly Ser Thr Asn Tyr Ala Asp Ser Val Lys
        50                  55                  60

Gly Arg Phe Thr Ile Ser Gly Asp Asn Ala Lys Asn Thr Val Tyr Leu
65                  70                  75                  80

Gln Met Asn Asn Leu Lys Pro Glu Asp Thr Ala Val Tyr Tyr Cys Tyr
                85                  90                  95

Ala Asp Leu Ile Arg Pro Gly Asp Phe Tyr Gly Met Asp Tyr Trp Gly
            100                 105                 110

Lys Gly Thr Leu Val Thr Val Ser Ser
        115                 120
```

<210> SEQ ID NO 43
<211> LENGTH: 122
<212> TYPE: PRT
<213> ORGANISM: Artificial Sequence
<220> FEATURE:
<223> OTHER INFORMATION: Amino acid sequence of the anti-CLD18A2 nanobody

<400> SEQUENCE: 43

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Leu Ile Asn
            20                  25                  30

Ala Met Gly Trp Tyr Arg Gln Ala Pro Gly Lys Gln Arg Glu Leu Val
        35                  40                  45

Ala Val Ile Thr Arg Gly Gly Ser Ala Asn Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Asn Leu Arg Ser Asp Pro Phe Lys Trp Tyr Thr Phe Trp
            100                 105                 110

Gly Gln Gly Thr Gln Val Thr Val Ser Ser
        115                 120
```

<210> SEQ ID NO 44
<211> LENGTH: 121
<212> TYPE: PRT
<213> ORGANISM: Artificial Sequence
<220> FEATURE:
<223> OTHER INFORMATION: Amino acid sequence of the anti-CLD18A2 nanobody

<400> SEQUENCE: 44

```
Gln Val Gln Leu Val Glu Ser Gly Gly Gly Leu Val Gln Pro Gly Gly
1               5                   10                  15

Ser Leu Arg Leu Ser Cys Thr Ala Ser Gly Ser Ile Phe Arg Ile Asp
            20                  25                  30

Gly Met His Trp Tyr Arg Gln Ala Pro Gly Lys Gln Arg Glu Leu Val
        35                  40                  45

Ala Ser Ile Thr Pro Ser Gly Ile Thr His Tyr Ala Asp Ser Val Lys
    50                  55                  60

Gly Arg Phe Thr Ile Ser Arg Asp Ile Ala Lys Lys Met Gln Tyr Leu
65                  70                  75                  80

Gln Met Asn Ser Leu Lys Pro Glu Asp Thr Ala Val Tyr Tyr Cys Asn
                85                  90                  95

Ala His Leu Val Lys Val Gly Gly Val Trp Ser Asp Glu Tyr Trp Gly
            100                 105                 110

Gln Gly Thr Gln Val Thr Val Ser Ser
        115                 120
```

<210> SEQ ID NO 45
<211> LENGTH: 120
<212> TYPE: PRT
<213> ORGANISM: Artificial Sequence
<220> FEATURE:
<223> OTHER INFORMATION: Amino acid sequence of the anti-CLD18A2 nanobody

<400> SEQUENCE: 45

Gln Leu Gln Leu Val Glu Ser Gly Gly Gly Leu Val Gln Pro Gly Gly
1               5                   10                  15

Ser Leu Arg Leu Ser Cys Ala Ala Ser Gly Val Asp Ile Ser Ser Asp
            20                  25                  30

Val Met Ala Trp Tyr Arg Gln Ala Pro Gly Lys Gln Arg Glu Phe Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Phe Ala Lys Asn Thr Val Asp Leu
65                  70                  75                  80

Gln Met Asn Ser Leu Lys Pro Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Gln Val Thr Val Ser Ser
        115                 120

<210> SEQ ID NO 46
<211> LENGTH: 122
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 46

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Phe Gly Gly Gly Ser Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Asp Leu Leu Val Gly Gly Phe Pro Arg Arg Asn Val Tyr Trp
            100                 105                 110

Gly Gln Gly Thr Gln Val Thr Val Ser Ser
        115                 120

<210> SEQ ID NO 47
<211> LENGTH: 122
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 47

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Met Ile Asn
            20                  25                  30

Val Met Gly Trp Tyr Arg Gln Ala Pro Gly Lys Gln Arg Glu Leu Val
        35                  40                  45

Ala Val Ile Thr Arg Gly Ala Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Asp Leu Leu Ala Ser Asp Pro Phe Lys Trp Tyr Thr Tyr Trp
                100                 105                 110

Gly Gln Gly Thr Gln Val Thr Val Ser Ser
        115                 120

<210> SEQ ID NO 48
<211> LENGTH: 119
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 48

Gln Leu Gln Leu Val Glu Ser Gly Gly Gly Leu Val Gln Pro Gly Gly
 1               5                  10                  15

Ser Leu Arg Leu Ser Cys Ala Ala Ser Gly Glu Ile Ser Ser Asp Ala
            20                  25                  30

Met Ala Trp Tyr Arg Gln Ala Pro Gly Lys Gln Arg Glu Leu Val Ala
        35                  40                  45

Gly Met Thr Arg Gly Gly Ser Thr Asn Tyr Ala Asp Ser Val Lys Gly
 50                  55                  60

Arg Phe Thr Ile Ser Arg Asp Phe Ala Lys Asn Thr Val Asp Leu Gln
 65                  70                  75                  80

Met Asn Ser Leu Lys Pro Glu Asp Thr Ala Val Tyr Tyr Cys Asn Ala
                 85                  90                  95

Glu Ile Tyr Thr Gly Thr Phe Tyr Pro Arg Ser Tyr Trp Gly Gln Gly
                100                 105                 110

Thr Gln Val Thr Val Ser Ser
        115

<210> SEQ ID NO 49
<211> LENGTH: 121
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 49

Gln Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ile Pro
            20                  25                  30

Val Met Thr Trp Tyr Arg Gln Ala Leu Gly Lys Glu Arg Glu Phe Val
        35                  40                  45

Ala Gly Ile Ser Lys Gly Gly Thr Ser Asn Tyr Ala Asp Ser Val Lys
 50                  55                  60

Gly Arg Phe Thr Val Ser Arg Asp Asn Ala Lys Asn Thr Val Tyr Leu
 65                  70                  75                  80

Gln Met Asn Ser Leu Lys Ser Glu Asp Thr Ala Val Tyr Tyr Cys Asn
            85                  90                  95

Ala Gln Ala Ser Ser Phe Gly Trp Met Pro Leu Ser Tyr Trp Gly
        100                 105                 110

Gln Gly Thr Gln Val Thr Val Ser Ser
        115                 120

<210> SEQ ID NO 50
<211> LENGTH: 17
<212> TYPE: PRT
<213> ORGANISM: Artificial Sequence
<220> FEATURE:
<223> OTHER INFORMATION: Amino acid sequence

<400> SEQUENCE: 50

Met Gly Trp Val Arg Gln Ala Pro Gly Lys Gly Leu Glu Trp Val Ala
1               5                   10                  15

Thr

<210> SEQ ID NO 51
<211> LENGTH: 17
<212> TYPE: PRT
<213> ORGANISM: Artificial Sequence
<220> FEATURE:
<223> OTHER INFORMATION: Amino acid sequence

<400> SEQUENCE: 51

Met Gly Trp Tyr Arg Gln Ala Pro Gly Lys Gly Leu Glu Leu Val Ala
1               5                   10                  15

Thr

<210> SEQ ID NO 52
<211> LENGTH: 38
<212> TYPE: PRT
<213> ORGANISM: Artificial Sequence
<220> FEATURE:
<223> OTHER INFORMATION: Amino acid sequence

<400> SEQUENCE: 52

Asn Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 53
<211> LENGTH: 38
<212> TYPE: PRT
<213> ORGANISM: Artificial Sequence
<220> FEATURE:
<223> OTHER INFORMATION: Amino acid sequence

<400> SEQUENCE: 53

His Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 54

```
<211> LENGTH: 11
<212> TYPE: PRT
<213> ORGANISM: Artificial Sequence
<220> FEATURE:
<223> OTHER INFORMATION: Amino acid sequence

<400> SEQUENCE: 54

Trp Gly Gln Gly Thr Leu Val Thr Val Ser Ser
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Amino acid sequence

<400> SEQUENCE: 55

Met Gly Trp Val Arg Gln Ala Pro Gly Lys Gly Leu Glu Trp Val Ala
1               5                   10                  15

Val

<210> SEQ ID NO 56
<211> LENGTH: 17
<212> TYPE: PRT
<213> ORGANISM: Artificial Sequence
<220> FEATURE:
<223> OTHER INFORMATION: Amino acid sequence

<400> SEQUENCE: 56

Met His Trp Val Arg Gln Ala Pro Gly Lys Gly Leu Glu Trp Val Ala
1               5                   10                  15

Ser

<210> SEQ ID NO 57
<211> LENGTH: 17
<212> TYPE: PRT
<213> ORGANISM: Artificial Sequence
<220> FEATURE:
<223> OTHER INFORMATION: Amino acid sequence

<400> SEQUENCE: 57

Met Ala Trp Val Arg Gln Ala Pro Gly Lys Gly Leu Glu Trp Val Ser
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: Amino acid sequence

<400> SEQUENCE: 58

Met Gly Trp Val Arg Gln Ala Pro Gly Lys Gly Leu Glu Trp Val Ala
1               5                   10                  15

Ala

<210> SEQ ID NO 59
<211> LENGTH: 17
<212> TYPE: PRT
<213> ORGANISM: Artificial Sequence
<220> FEATURE:
<223> OTHER INFORMATION: Amino acid sequence
```

<400> SEQUENCE: 59

Met Ala Trp Val Arg Gln Ala Pro Gly Lys Gly Leu Glu Trp Val Ala
1               5                   10                  15

Gly

<210> SEQ ID NO 60
<211> LENGTH: 17
<212> TYPE: PRT
<213> ORGANISM: Artificial Sequence
<220> FEATURE:
<223> OTHER INFORMATION: Amino acid sequence

<400> SEQUENCE: 60

Met Thr Trp Val Arg Gln Ala Pro Gly Lys Gly Leu Glu Trp Val Ala
1               5                   10                  15

Gly

<210> SEQ ID NO 61
<211> LENGTH: 17
<212> TYPE: PRT
<213> ORGANISM: Artificial Sequence
<220> FEATURE:
<223> OTHER INFORMATION: Amino acid sequence

<400> SEQUENCE: 61

Met Gly Trp Tyr Arg Gln Ala Pro Gly Lys Gly Leu Glu Leu Val Ala
1               5                   10                  15

Val

<210> SEQ ID NO 62
<211> LENGTH: 17
<212> TYPE: PRT
<213> ORGANISM: Artificial Sequence
<220> FEATURE:
<223> OTHER INFORMATION: Amino acid sequence

<400> SEQUENCE: 62

Met His Trp Tyr Arg Gln Ala Pro Gly Lys Gly Leu Glu Leu Val Ala
1               5                   10                  15

Ser

<210> SEQ ID NO 63
<211> LENGTH: 17
<212> TYPE: PRT
<213> ORGANISM: Artificial Sequence
<220> FEATURE:
<223> OTHER INFORMATION: Amino acid sequence

<400> SEQUENCE: 63

Met Ala Trp Tyr Arg Gln Ala Pro Gly Lys Gly Leu Glu Phe Val Ser
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: Amino acid sequence -continued

```
<400> SEQUENCE: 64

Met Gly Trp Tyr Arg Gln Ala Pro Gly Lys Gly Leu Glu Leu Val Ala
1               5                   10                  15

Ala

<210> SEQ ID NO 65
<211> LENGTH: 17
<212> TYPE: PRT
<213> ORGANISM: Artificial Sequence
<220> FEATURE:
<223> OTHER INFORMATION: Amino acid sequence

<400> SEQUENCE: 65

Met Ala Trp Tyr Arg Gln Ala Pro Gly Lys Gly Leu Glu Leu Val Ala
1               5                   10                  15

Gly

<210> SEQ ID NO 66
<211> LENGTH: 17
<212> TYPE: PRT
<213> ORGANISM: Artificial Sequence
<220> FEATURE:
<223> OTHER INFORMATION: Amino acid sequence

<400> SEQUENCE: 66

Met Thr Trp Tyr Arg Gln Ala Pro Gly Lys Gly Leu Glu Phe Val Ala
1               5                   10                  15

Gly

<210> SEQ ID NO 67
<211> LENGTH: 121
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 67

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Phe Ser Ile Gly
            20                  25                  30

Val Met Gly Trp Tyr Arg Gln Ala Pro Gly Lys Gln Arg Glu Leu Val
        35                  40                  45

Ala Thr Ile Thr Ser Arg Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Asp Leu Ile Arg Pro Gly Asp Phe Tyr Gly Met Asp Tyr Trp Gly
            100                 105                 110

Gln Gly Thr Leu Val Thr Val Ser Ser
        115                 120

<210> SEQ ID NO 68
<211> LENGTH: 122
<212> TYPE: PRT
<213> ORGANISM: Artificial Sequence
<220> FEATURE:
```

<223> OTHER INFORMATION: Amino acid sequence of the anti-CLD18A2
      nanobody

<400> SEQUENCE: 68

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Leu Ile Asn
            20                  25                  30

Ala Met Gly Trp Tyr Arg Gln Ala Pro Gly Lys Gln Arg Glu Leu Val
        35                  40                  45

Ala Val Ile Thr Arg Gly Gly Ser Ala Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Asp Leu Asn Leu Arg Ser Asp Pro Phe Lys Trp Tyr Thr Phe Trp
            100                 105                 110

Gly Gln Gly Thr Leu Val Thr Val Ser Ser
        115                 120

<210> SEQ ID NO 69
<211> LENGTH: 121
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Asp
            20                  25                  30

Gly Met His Trp Tyr Arg Gln Ala Pro Gly Lys Gln Arg Glu Leu Val
        35                  40                  45

Ala Ser Ile Thr Pro Ser Gly Ile Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala His Leu Val Lys Val Gly Gly Val Trp Ser Asp Glu Tyr Trp Gly
            100                 105                 110

Gln Gly Thr Leu Val Thr Val Ser Ser
        115                 120

<210> SEQ ID NO 70
<211> LENGTH: 120
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 70

Gln Val Gln Leu Val Glu Ser Gly Gly Gly Leu Val Gln Pro Gly Gly
1               5                   10                  15

```
Ser Leu Arg Leu Ser Cys Ala Ala Ser Gly Val Asp Ile Ser Ser Asp
            20                  25                  30

Val Met Ala Trp Tyr Arg Gln Ala Pro Gly Lys Gln Arg Glu Phe Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Leu Val Thr Val Ser Ser
        115                 120

<210> SEQ ID NO 71
<211> LENGTH: 122
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 71

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Phe Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Asn Ala Asp Leu Leu Val Gly Gly Phe Pro Arg Arg Asn Val Tyr Trp
            100                 105                 110

Gly Gln Gly Thr Leu Val Thr Val Ser Ser
        115                 120

<210> SEQ ID NO 72
<211> LENGTH: 122
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 72

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Met Ile Asn
            20                  25                  30

Val Met Gly Trp Tyr Arg Gln Ala Pro Gly Lys Gln Arg Glu Leu Val
        35                  40                  45

Ala Val Ile Thr Arg Gly Ala Ser Thr Asn Tyr Ala Asp Ser Val Lys
    50                  55                  60
```

```
Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Asp Leu Asn Leu Ala Ser Asp Pro Phe Lys Trp Tyr Thr Tyr Trp
            100                 105                 110

Gly Gln Gly Thr Leu Val Thr Val Ser Ser
        115                 120
```

<210> SEQ ID NO 73
<211> LENGTH: 119
<212> TYPE: PRT
<213> ORGANISM: Artificial Sequence
<220> FEATURE:
<223> OTHER INFORMATION: Amino acid sequence of the anti-CLD18A2 nanobody

<400> SEQUENCE: 73

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Glu Ile Ser Ser Asp Ala
            20                  25                  30

Met Ala Trp Tyr Arg Gln Ala Pro Gly Lys Gln Arg Glu Leu Val Ala
        35                  40                  45

Gly Met Thr Arg Gly Gly Ser Thr Asn Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Glu Ile Tyr Thr Gly Thr Phe Tyr Pro Arg Ser Tyr Trp Gly Gln Gly
            100                 105                 110

Thr Leu Val Thr Val Ser Ser
        115
```

<210> SEQ ID NO 74
<211> LENGTH: 121
<212> TYPE: PRT
<213> ORGANISM: Artificial Sequence
<220> FEATURE:
<223> OTHER INFORMATION: Amino acid sequence of the anti-CLD18A2 nanobody

<400> SEQUENCE: 74

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Pro
            20                  25                  30

Val Met Thr Trp Tyr Arg Gln Ala Leu Gly Lys Glu Arg Glu Phe Val
        35                  40                  45

Ala Gly Ile Ser Lys Gly Gly Thr Ser Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Gln Ala Ser Ser Phe Gly Trp Met Pro Leu Ser Asp Tyr Trp Gly
            100                 105                 110
```

```
Gln Gly Thr Leu Val Thr Val Ser Ser
        115                 120
```

```
<210> SEQ ID NO 75
<211> LENGTH: 121
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 75
```

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Phe Ser Ile Gly
            20                  25                  30

Val Met Gly Trp Val Arg Gln Ala Pro Gly Lys Gly Leu Glu Trp Val
        35                  40                  45

Ala Thr Ile Thr Ser Arg Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Asp Leu Ile Arg Pro Gly Asp Phe Tyr Gly Met Asp Tyr Trp Gly
            100                 105                 110

Gln Gly Thr Leu Val Thr Val Ser Ser
        115                 120
```

```
<210> SEQ ID NO 76
<211> LENGTH: 122
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 76
```

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Leu Ile Asn
            20                  25                  30

Ala Met Gly Trp Val Arg Gln Ala Pro Gly Lys Gly Leu Glu Trp Val
        35                  40                  45

Ala Val Ile Thr Arg Gly Gly Ser Ala Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Asp Leu Asn Leu Arg Ser Asp Pro Phe Lys Trp Tyr Thr Phe Trp
            100                 105                 110

Gly Gln Gly Thr Leu Val Thr Val Ser Ser
        115                 120
```

```
<210> SEQ ID NO 77
<211> LENGTH: 121
<212> TYPE: PRT
<213> ORGANISM: Artificial Sequence
```

<220> FEATURE:
<223> OTHER INFORMATION: Amino acid sequence of the anti-CLD18A2 nanobody

<400> SEQUENCE: 77

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Asp
            20                  25                  30

Gly Met His Trp Val Arg Gln Ala Pro Gly Lys Gly Leu Glu Trp Val
        35                  40                  45

Ala Ser Ile Thr Pro Ser Gly Ile Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala His Leu Val Lys Val Gly Gly Val Trp Ser Asp Glu Tyr Trp Gly
            100                 105                 110

Gln Gly Thr Leu Val Thr Val Ser Ser
        115                 120

<210> SEQ ID NO 78
<211> LENGTH: 120
<212> TYPE: PRT
<213> ORGANISM: Artificial Sequence
<220> FEATURE:
<223> OTHER INFORMATION: Amino acid sequence of the anti-CLD18A2 nanobody

<400> SEQUENCE: 78

Gln Val Gln Leu Val Glu Ser Gly Gly Gly Leu Val Gln Pro Gly Gly
1               5                   10                  15

Ser Leu Arg Leu Ser Cys Ala Ala Ser Gly Val Asp Ile Ser Ser Asp
            20                  25                  30

Val Met Ala Trp Val Arg Gln Ala Pro Gly Lys Gly Leu Glu Trp Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Leu Val Thr Val Ser Ser
        115                 120

<210> SEQ ID NO 79
<211> LENGTH: 122
<212> TYPE: PRT
<213> ORGANISM: Artificial Sequence
<220> FEATURE:
<223> OTHER INFORMATION: Amino acid sequence of the anti-CLD18A2 nanobody

<400> SEQUENCE: 79

Gln Val Gln Leu Val Glu Ser Gly Gly Gly Leu Val Gln Pro Gly Gly
1               5                   10                  15

```
Ser Leu Arg Leu Ser Cys Ala Ala Ser Gly Ser Ile Phe Ser Ile Asn
            20                  25                  30

Ala Met Gly Trp Val Arg Gln Ala Pro Gly Lys Gly Leu Glu Trp Val
        35                  40                  45

Ala Ala Ile Thr Phe Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Asn Ala Asp Leu Leu Val Gly Gly Phe Pro Arg Arg Asn Val Tyr Trp
                100                 105                 110

Gly Gln Gly Thr Leu Val Thr Val Ser Ser
            115                 120
```

<210> SEQ ID NO 80
<211> LENGTH: 122
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 80

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Met Ile Asn
            20                  25                  30

Val Met Gly Trp Val Arg Gln Ala Pro Gly Lys Gly Leu Glu Trp Val
        35                  40                  45

Ala Val Ile Thr Arg Gly Ala Ser Thr Asn Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Asn
                85                  90                  95

Ala Asp Leu Asn Leu Ala Ser Asp Pro Phe Lys Trp Tyr Thr Tyr Trp
                100                 105                 110

Gly Gln Gly Thr Leu Val Thr Val Ser Ser
            115                 120
```

<210> SEQ ID NO 81
<211> LENGTH: 119
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 81

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Glu Ile Ser Ser Asp Ala
            20                  25                  30

Met Ala Trp Val Arg Gln Ala Pro Gly Lys Gly Leu Glu Trp Val Ala
        35                  40                  45

Gly Met Thr Arg Gly Gly Ser Thr Asn Tyr Ala Asp Ser Val Lys Gly
    50                  55                  60
```

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
            85                  90                  95

Glu Ile Tyr Thr Gly Thr Phe Tyr Pro Arg Ser Tyr Trp Gly Gln Gly
            100                 105                 110

Thr Leu Val Thr Val Ser Ser
            115

<210> SEQ ID NO 82
<211> LENGTH: 121
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 82

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Pro
            20                  25                  30

Val Met Thr Trp Val Arg Gln Ala Pro Gly Lys Gly Leu Glu Trp Val
            35                  40                  45

Ala Gly Ile Ser Lys Gly Gly Thr Ser Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
            85                  90                  95

Ala Gln Ala Ser Ser Phe Gly Trp Met Pro Leu Ser Asp Tyr Trp Gly
            100                 105                 110

Gln Gly Thr Leu Val Thr Val Ser Ser
            115                 120

<210> SEQ ID NO 83
<211> LENGTH: 121
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 83

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Phe Ser Ile Gly
            20                  25                  30

Val Met Gly Trp Tyr Arg Gln Ala Pro Gly Lys Gly Leu Glu Leu Val
            35                  40                  45

Ala Thr Ile Thr Ser Arg Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
            85                  90                  95

Ala Asp Leu Ile Arg Pro Gly Asp Phe Tyr Gly Met Asp Tyr Trp Gly
            100                 105                 110

```
Gln Gly Thr Leu Val Thr Val Ser Ser
        115                 120

<210> SEQ ID NO 84
<211> LENGTH: 122
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 84

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Leu Ile Asn
            20                  25                  30

Ala Met Gly Trp Tyr Arg Gln Ala Pro Gly Lys Gly Leu Glu Leu Val
        35                  40                  45

Ala Val Ile Thr Arg Gly Gly Ser Ala Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Asp Leu Asn Leu Arg Ser Asp Pro Phe Lys Trp Tyr Thr Phe Trp
            100                 105                 110

Gly Gln Gly Thr Leu Val Thr Val Ser Ser
        115                 120

<210> SEQ ID NO 85
<211> LENGTH: 121
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Asp
            20                  25                  30

Gly Met His Trp Tyr Arg Gln Ala Pro Gly Lys Gly Leu Glu Leu Val
        35                  40                  45

Ala Ser Ile Thr Pro Ser Gly Ile Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala His Leu Val Lys Val Gly Gly Val Trp Ser Asp Glu Tyr Trp Gly
            100                 105                 110

Gln Gly Thr Leu Val Thr Val Ser Ser
        115                 120

<210> SEQ ID NO 86
<211> LENGTH: 120
<212> TYPE: PRT
<213> ORGANISM: Artificial Sequence
<220> FEATURE:
```

<223> OTHER INFORMATION: Amino acid sequence of the anti-CLD18A2
      nanobody

<400> SEQUENCE: 86

Gln Val Gln Leu Val Glu Ser Gly Gly Gly Leu Val Gln Pro Gly Gly
1               5                   10                  15

Ser Leu Arg Leu Ser Cys Ala Ala Ser Gly Val Asp Ile Ser Ser Asp
            20                  25                  30

Val Met Ala Trp Tyr Arg Gln Ala Pro Gly Lys Gly Leu Glu Phe Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Leu Val Thr Val Ser Ser
        115                 120

<210> SEQ ID NO 87
<211> LENGTH: 122
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 87

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gly Leu Glu Leu Val
        35                  40                  45

Ala Ala Ile Thr Phe Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Asn Ala Asp Leu Leu Val Gly Gly Phe Pro Arg Arg Asn Val Tyr Trp
            100                 105                 110

Gly Gln Gly Thr Leu Val Thr Val Ser Ser
        115                 120

<210> SEQ ID NO 88
<211> LENGTH: 122
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 88

Gln Val Gln Leu Val Glu Ser Gly Gly Gly Leu Val Gln Pro Gly Gly
1               5                   10                  15

```
Ser Leu Arg Leu Ser Cys Ala Ala Ser Gly Ser Ile Phe Met Ile Asn
            20                  25                  30

Val Met Gly Trp Tyr Arg Gln Ala Pro Gly Lys Gly Leu Glu Leu Val
        35                  40                  45

Ala Val Ile Thr Arg Gly Ala Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Asp Leu Asn Leu Ala Ser Asp Pro Phe Lys Trp Tyr Thr Tyr Trp
            100                 105                 110

Gly Gln Gly Thr Leu Val Thr Val Ser Ser
        115                 120

<210> SEQ ID NO 89
<211> LENGTH: 119
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 89

Gln Val Gln Leu Val Glu Ser Gly Gly Gly Leu Val Gln Pro Gly Gly
1               5                   10                  15

Ser Leu Arg Leu Ser Cys Ala Ala Ser Gly Glu Ile Ser Asp Ala
            20                  25                  30

Met Ala Trp Tyr Arg Gln Ala Pro Gly Lys Gly Leu Glu Leu Val Ala
        35                  40                  45

Gly Met Thr Arg Gly Gly Ser Thr Asn Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Glu Ile Tyr Thr Gly Thr Phe Tyr Pro Arg Ser Tyr Trp Gly Gln Gly
            100                 105                 110

Thr Leu Val Thr Val Ser Ser
        115

<210> SEQ ID NO 90
<211> LENGTH: 121
<212> TYPE: PRT
<213> ORGANISM: Artificial Sequence
<220> FEATURE:
<223> OTHER INFORMATION: Amino acid sequence of the anti-CLD18A2
      nanobody

<400> SEQUENCE: 90

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Pro
            20                  25                  30

Val Met Thr Trp Tyr Arg Gln Ala Pro Gly Lys Gly Leu Glu Phe Val
        35                  40                  45

Ala Gly Ile Ser Lys Gly Gly Thr Ser Asn Tyr Ala Asp Ser Val Lys
    50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
            85                  90                  95

Ala Gln Ala Ser Ser Phe Gly Trp Met Pro Leu Ser Asp Tyr Trp Gly
        100                 105                 110

Gln Gly Thr Leu Val Thr Val Ser Ser
        115                 120

<210> SEQ ID NO 91
<211> LENGTH: 231
<212> TYPE: PRT
<213> ORGANISM: Artificial Sequence
<220> FEATURE:
<223> OTHER INFORMATION: Amino acid sequence of the immunoglobulin Fc
      region

<400> SEQUENCE: 91

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
        100                 105                 110

Leu Pro Ala Pro Ile Glu Lys Thr Ile Ser Lys Ala Lys Gly Gln Pro
    115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 92
<211> LENGTH: 231
<212> TYPE: PRT
<213> ORGANISM: Artificial Sequence
<220> FEATURE:
<223> OTHER INFORMATION: Amino acid sequence of the immunoglobulin Fc
      region

<400> SEQUENCE: 92

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 93
<211> LENGTH: 226
<212> TYPE: PRT
<213> ORGANISM: Artificial Sequence
<220> FEATURE:
<223> OTHER INFORMATION: Amino acid sequence of the immunoglobulin Fc
      region

<400> SEQUENCE: 93

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

```
Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 94
<211> LENGTH: 231
<212> TYPE: PRT
<213> ORGANISM: Artificial Sequence
<220> FEATURE:
<223> OTHER INFORMATION: Amino acid sequence of the immunoglobulin Fc
      region

<400> SEQUENCE: 94

Glu Pro Lys Ser Cys Asp Lys Thr His Thr Cys Pro Pro Cys Pro Ala
1               5                   10                  15

Pro Glu Leu Leu Gly Gly Pro Asp Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Glu Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 95
<211> LENGTH: 231
<212> TYPE: PRT
<213> ORGANISM: Artificial Sequence
<220> FEATURE:
<223> OTHER INFORMATION: Amino acid sequence of the immunoglobulin Fc
      region

<400> SEQUENCE: 95

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Trp Ala
            100                 105                 110

Leu Pro Ala Pro Ile Ser Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 96
<211> LENGTH: 261
<212> TYPE: PRT
<213> ORGANISM: Artificial Sequence
<220> FEATURE:
<223> OTHER INFORMATION: Amino acid sequence of CLD18A1

<400> SEQUENCE: 96

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30
```

```
Gln Asp Leu Tyr Asp Asn Pro Val Thr Ser Val Phe Gln Tyr Glu Gly
             35                  40                  45

Leu Trp Arg Ser Cys Val Arg Gln Ser Ser Gly Phe Thr Glu Cys Arg
 50                  55                  60

Pro Tyr Phe Thr Ile Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                 85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
             115                 120                 125

Gly Leu Cys Ala Ile Ala Gly Val Ser Val Phe Ala Asn Met Leu Val
         130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
             180                 185                 190

Cys Ile Ala Cys Arg Gly Leu Ala Pro Glu Glu Thr Asn Tyr Lys Ala
         195                 200                 205

Val Ser Tyr His Ala Ser Gly His Ser Val Ala Tyr Lys Pro Gly Gly
         210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 97
<211> LENGTH: 261
<212> TYPE: PRT
<213> ORGANISM: Artificial Sequence
<220> FEATURE:
<223> OTHER INFORMATION: Amino acid sequence of CLD18A2

<400> SEQUENCE: 97

Met Ala Val Thr Ala Cys Gln Gly Leu Gly Phe Val Val Ser Leu Ile
 1               5                  10                  15

Gly Ile Ala Gly Ile Ile Ala Ala Thr Cys Met Asp Gln Trp Ser Thr
                 20                  25                  30

Gln Asp Leu Tyr Asn Asn Pro Val Thr Ala Val Phe Asn Tyr Gln Gly
             35                  40                  45

Leu Trp Arg Ser Cys Val Arg Glu Ser Ser Gly Phe Thr Glu Cys Arg
 50                  55                  60

Gly Tyr Phe Thr Leu Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                 85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
             115                 120                 125
```

-continued

Gly Leu Cys Ala Ile Ala Gly Val Ser Val Phe Ala Asn Met Leu Val
            130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Gly Thr Asn Tyr Lys Ala
            195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 98
<211> LENGTH: 352
<212> TYPE: PRT
<213> ORGANISM: Artificial Sequence
<220> FEATURE:
<223> OTHER INFORMATION: Amino acid sequence of Anti-C18.2-6-Fc

<400> SEQUENCE: 98

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Phe Ser Ile Gly
            20                  25                  30

Val Met Gly Trp Tyr Arg Gln Ala Pro Gly Lys Gln Arg Glu Leu Val
        35                  40                  45

Ala Thr Ile Thr Ser Arg Gly Ser Thr Asn Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Asn Leu Lys Pro Glu Asp Thr Ala Val Tyr Tyr Cys Tyr
                85                  90                  95

Ala Asp Leu Ile Arg Pro Gly Asp Phe Tyr Gly Met Asp Tyr Trp Gly
            100                 105                 110

Gln Gly Thr Leu Val Thr Val Ser Ser Glu Pro Lys Ser Cys Asp Lys
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

```
Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
            245                 250                 255

Leu Pro Pro Ser Arg Asp Glu Leu Thr Lys Asn Gln Val Ser Leu Thr
        260                 265                 270

Cys Leu Val Lys Gly Phe Tyr Pro Ser Asp Ile Ala Val Glu Trp Glu
    275                 280                 285

Ser Asn Gly Gln Pro Glu Asn Asn Tyr Lys Thr Thr Pro Pro Val Leu
290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
                340                 345                 350
```

<210> SEQ ID NO 99
<211> LENGTH: 353
<212> TYPE: PRT
<213> ORGANISM: Artificial Sequence
<220> FEATURE:
<223> OTHER INFORMATION: Amino acid sequence of Anti-C18.2-7-Fc

<400> SEQUENCE: 99

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Leu Ile Asn
            20                  25                  30

Ala Met Gly Trp Tyr Arg Gln Ala Pro Gly Lys Gln Arg Glu Leu Val
        35                  40                  45

Ala Val Ile Thr Arg Gly Gly Ser Ala Asn Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Asn Leu Arg Ser Asp Pro Phe Lys Trp Tyr Thr Phe Trp
            100                 105                 110

Gly Gln Gly Thr Leu Val Thr Val Ser Ser Glu Pro Lys Ser Cys Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240
```

```
Lys Thr Ile Ser Lys Ala Lys Gly Gln Pro Arg Glu Pro Gln Val Tyr
            245                 250                 255

Thr Leu Pro Pro Ser Arg Asp Glu Leu Thr Lys Asn Gln Val Ser Leu
        260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
        290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
            325                 330                 335

Glu Ala Leu His Asn His Tyr Thr Gln Lys Ser Leu Ser Leu Ser Pro
            340                 345                 350

Gly

<210> SEQ ID NO 100
<211> LENGTH: 352
<212> TYPE: PRT
<213> ORGANISM: Artificial Sequence
<220> FEATURE:
<223> OTHER INFORMATION: Amino acid sequence of Anti-C18.2-15-Fc

<400> SEQUENCE: 100

Gln Val Gln Leu Val Glu Ser Gly Gly Gly Leu Val Gln Pro Gly Gly
1               5                   10                  15

Ser Leu Arg Leu Ser Cys Thr Ala Ser Gly Ser Ile Phe Arg Ile Asp
            20                  25                  30

Gly Met His Trp Tyr Arg Gln Ala Pro Gly Lys Gln Arg Glu Leu Val
        35                  40                  45

Ala Ser Ile Thr Pro Ser Gly Ile Thr His Tyr Ala Asp Ser Val Lys
    50                  55                  60

Gly Arg Phe Thr Ile Ser Arg Asp Ile Ala Lys Lys Met Gln Tyr Leu
65                  70                  75                  80

Gln Met Asn Ser Leu Lys Pro Glu Asp Thr Ala Val Tyr Tyr Cys Asn
                85                  90                  95

Ala His Leu Val Lys Val Gly Gly Val Trp Ser Asp Glu Tyr Trp Gly
            100                 105                 110

Gln Gly Thr Leu Val Thr Val Ser Ser Glu Pro Lys Ser Cys Asp Lys
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240
```

```
Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

<210> SEQ ID NO 101
<211> LENGTH: 351
<212> TYPE: PRT
<213> ORGANISM: Artificial Sequence
<220> FEATURE:
<223> OTHER INFORMATION: Amino acid sequence of Anti-C18.2-19-Fc

<400> SEQUENCE: 101

Gln Val Gln Leu Val Glu Ser Gly Gly Gly Leu Val Gln Pro Gly Gly
1               5                   10                  15

Ser Leu Arg Leu Ser Cys Ala Ala Ser Gly Val Asp Ile Ser Ser Asp
            20                  25                  30

Val Met Ala Trp Tyr Arg Gln Ala Pro Gly Lys Gln Arg Glu Phe Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Phe Ala Lys Asn Thr Val Asp Leu
65                  70                  75                  80

Gln Met Asn Ser Leu Lys Pro Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Leu Val Thr Val Ser Ser Glu Pro Lys Ser Cys Asp Lys Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255
```

```
Pro Pro Ser Arg Asp Glu Leu Thr Lys Asn Gln Val Ser Leu Thr Cys
        260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
            340                 345                 350

<210> SEQ ID NO 102
<211> LENGTH: 353
<212> TYPE: PRT
<213> ORGANISM: Artificial Sequence
<220> FEATURE:
<223> OTHER INFORMATION: amino acid sequence of Anti-C18.2-20-Fc

<400> SEQUENCE: 102

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Phe Gly Gly Ser Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Asp Leu Leu Val Gly Gly Phe Pro Arg Arg Asn Val Tyr Trp
            100                 105                 110

Gly Gln Gly Thr Leu Val Thr Val Ser Ser Glu Pro Lys Ser Cys Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270
```

```
Thr Cys Leu Val Lys Gly Phe Tyr Pro Ser Asp Ile Ala Val Glu Trp
            275                 280                 285

Glu Ser Asn Gly Gln Pro Glu Asn Asn Tyr Lys Thr Thr Pro Pro Val
        290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
            325                 330                 335

Glu Ala Leu His Asn His Tyr Thr Gln Lys Ser Leu Ser Leu Ser Pro
            340                 345                 350

Gly
```

<210> SEQ ID NO 103
<211> LENGTH: 353
<212> TYPE: PRT
<213> ORGANISM: Artificial Sequence
<220> FEATURE:
<223> OTHER INFORMATION: Amino acid sequence of Anti-C18.2-28-Fc

<400> SEQUENCE: 103

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Met Ile Asn
            20                  25                  30

Val Met Gly Trp Tyr Arg Gln Ala Pro Gly Lys Gln Arg Glu Leu Val
        35                  40                  45

Ala Val Ile Thr Arg Gly Ala Ser Thr Asn Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Ala Asp Leu Asn Leu Ala Ser Asp Pro Phe Lys Trp Tyr Thr Tyr Trp
            100                 105                 110

Gly Gln Gly Thr Leu Val Thr Val Ser Ser Glu Pro Lys Ser Cys Asp
        115                 120                 125

Lys Thr His Thr Cys Pro Pro Cys Pro Ala Pro Glu Leu Leu Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
            165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
            245                 250                 255

Thr Leu Pro Pro Ser Arg Asp Glu Leu Thr Lys Asn Gln Val Ser Leu
            260                 265                 270
```

```
Thr Cys Leu Val Lys Gly Phe Tyr Pro Ser Asp Ile Ala Val Glu Trp
            275                 280                 285

Glu Ser Asn Gly Gln Pro Glu Asn Asn Tyr Lys Thr Thr Pro Pro Val
        290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly

<210> SEQ ID NO 104
<211> LENGTH: 350
<212> TYPE: PRT
<213> ORGANISM: Artificial Sequence
<220> FEATURE:
<223> OTHER INFORMATION: Amino acid sequence of Anti-C18.2-32-Fc

<400> SEQUENCE: 104

Gln Val Gln Leu Val Glu Ser Gly Gly Gly Leu Val Gln Pro Gly Gly
1               5                   10                  15

Ser Leu Arg Leu Ser Cys Ala Ala Ser Gly Glu Ile Ser Ser Asp Ala
            20                  25                  30

Met Ala Trp Tyr Arg Gln Ala Pro Gly Lys Gln Arg Glu Leu Val Ala
        35                  40                  45

Gly Met Thr Arg Gly Gly Ser Thr Asn Tyr Ala Asp Ser Val Lys Gly
    50                  55                  60

Arg Phe Thr Ile Ser Arg Asp Phe Ala Lys Asn Thr Val Asp Leu Gln
65                  70                  75                  80

Met Asn Ser Leu Lys Pro Glu Asp Thr Ala Val Tyr Tyr Cys Asn Ala
            85                  90                  95

Glu Ile Tyr Thr Gly Thr Phe Tyr Pro Arg Ser Tyr Trp Gly Gln Gly
            100                 105                 110

Thr Leu Val Thr Val Ser Ser Glu Pro Lys Ser Cys Asp Lys Thr His
        115                 120                 125

Thr Cys Pro Pro Cys Pro Ala Pro Glu Leu Leu Gly Gly Pro Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Leu
            260                 265                 270
```

Val Lys Gly Phe Tyr Pro Ser Asp Ile Ala Val Glu Trp Glu Ser Asn
    275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly
                340                 345                 350

<210> SEQ ID NO 105
<211> LENGTH: 352
<212> TYPE: PRT
<213> ORGANISM: Artificial Sequence
<220> FEATURE:
<223> OTHER INFORMATION: Amino acid sequence of Anti-C18.2-69-Fc

<400> SEQUENCE: 105

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Pro
                20                  25                  30

Val Met Thr Trp Tyr Arg Gln Ala Leu Gly Lys Glu Arg Glu Phe Val
                35                  40                  45

Ala Gly Ile Ser Lys Gly Gly Thr Ser Asn Tyr Ala Asp Ser Val Lys
            50                  55                  60

Gly Arg Phe Thr Val Ser Arg Asp Asn Ala Lys Asn Thr Val Tyr Leu
65              70                  75                  80

Gln Met Asn Ser Leu Lys Ser Glu Asp Thr Ala Val Tyr Tyr Cys Asn
                85                  90                  95

Ala Gln Ala Ser Ser Phe Gly Trp Met Pro Leu Ser Asp Tyr Trp Gly
                100                 105                 110

Gln Gly Thr Leu Val Thr Val Ser Ser Glu Pro Lys Ser Cys Asp Lys
            115                 120                 125

Thr His Thr Cys Pro Pro Cys Pro Ala Pro Glu Leu Leu Gly Gly Pro
        130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
                180                 185                 190

Ala Lys Thr Lys Pro Arg Glu Glu Gln Tyr Asn Ser Thr Tyr Arg Val
            195                 200                 205

Val Ser Val Leu Thr Val Leu His Gln Asp Trp Leu Asn Gly Lys Glu
        210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Thr
                260                 265                 270

Cys Leu Val Lys Gly Phe Tyr Pro Ser Asp Ile Ala Val Glu Trp Glu
            275                 280                 285

```
Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

<210> SEQ ID NO 106
<211> LENGTH: 352
<212> TYPE: PRT
<213> ORGANISM: Artificial Sequence
<220> FEATURE:
<223> OTHER INFORMATION: Amino acid sequence of Anti-C18.2-hu6V2-Fc

<400> SEQUENCE: 106

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Phe Ser Ile Gly
            20                  25                  30

Val Met Gly Trp Val Arg Gln Ala Pro Gly Lys Gly Leu Glu Trp Val
        35                  40                  45

Ala Thr Ile Thr Ser Arg Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Asp Leu Ile Arg Pro Gly Asp Phe Tyr Gly Met Asp Tyr Trp Gly
            100                 105                 110

Gln Gly Thr Leu Val Thr Val Ser Ser Glu Pro Lys Ser Cys Asp Lys
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300
```

```
Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
            325                 330                 335

Ala Leu His Asn His Tyr Thr Gln Lys Ser Leu Ser Leu Ser Pro Gly
            340                 345                 350

<210> SEQ ID NO 107
<211> LENGTH: 352
<212> TYPE: PRT
<213> ORGANISM: Artificial Sequence
<220> FEATURE:
<223> OTHER INFORMATION: Amino acid sequence of Anti-C18.2-hu6V3-Fc

<400> SEQUENCE: 107

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Phe Ser Ile Gly
            20                  25                  30

Val Met Gly Trp Tyr Arg Gln Ala Pro Gly Lys Gly Leu Glu Leu Val
        35                  40                  45

Ala Thr Ile Thr Ser Arg Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Asp Leu Ile Arg Pro Gly Asp Phe Tyr Gly Met Asp Tyr Trp Gly
            100                 105                 110

Gln Gly Thr Leu Val Thr Val Ser Ser Glu Pro Lys Ser Cys Asp Lys
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320
```

Ser Arg Trp Gln Gln Gly Asn Val Phe Ser Cys Ser Val Met His Glu
            325                 330                 335

Ala Leu His Asn His Tyr Thr Gln Lys Ser Leu Ser Leu Ser Pro Gly
            340                 345                 350

<210> SEQ ID NO 108
<211> LENGTH: 351
<212> TYPE: PRT
<213> ORGANISM: Artificial Sequence
<220> FEATURE:
<223> OTHER INFORMATION: Amino acid sequence of Anti-C18.2-hu19V1-Fc

<400> SEQUENCE: 108

Gln Val Gln Leu Val Glu Ser Gly Gly Gly Leu Val Gln Pro Gly Gly
1               5                   10                  15

Ser Leu Arg Leu Ser Cys Ala Ala Ser Gly Val Asp Ile Ser Ser Asp
            20                  25                  30

Val Met Ala Trp Tyr Arg Gln Ala Pro Gly Lys Gln Arg Glu Phe Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Leu Val Thr Val Ser Ser Glu Pro Lys Ser Cys Asp Lys Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

```
Leu His Asn His Tyr Thr Gln Lys Ser Leu Ser Leu Ser Pro Gly
            340                 345                 350

<210> SEQ ID NO 109
<211> LENGTH: 351
<212> TYPE: PRT
<213> ORGANISM: Artificial Sequence
<220> FEATURE:
<223> OTHER INFORMATION: Amino acid sequence of Anti-C18.2-hu19V3-Fc

<400> SEQUENCE: 109

Gln Val Gln Leu Val Glu Ser Gly Gly Gly Leu Val Gln Pro Gly Gly
1               5                   10                  15

Ser Leu Arg Leu Ser Cys Ala Ala Ser Gly Val Asp Ile Ser Ser Asp
            20                  25                  30

Val Met Ala Trp Tyr Arg Gln Ala Pro Gly Lys Gly Leu Glu Phe Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Leu Val Thr Val Ser Ser Glu Pro Lys Ser Cys Asp Lys Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
            340                 345                 350
```

<210> SEQ ID NO 110
<211> LENGTH: 18
<212> TYPE: DNA
<213> ORGANISM: Artificial Sequence
<220> FEATURE:
<223> OTHER INFORMATION: Upstream primer of the first round of PCR

<400> SEQUENCE: 110
cttggtggtc ctggctgc                                                18

<210> SEQ ID NO 111
<211> LENGTH: 23
<212> TYPE: DNA
<213> ORGANISM: Artificial Sequence
<220> FEATURE:
<223> OTHER INFORMATION: Downstream primer of the first round of PCR

<400> SEQUENCE: 111
ggtacgtgct gttgaactgt tcc                                          23

<210> SEQ ID NO 112
<211> LENGTH: 47
<212> TYPE: DNA
<213> ORGANISM: Artificial Sequence
<220> FEATURE:
<223> OTHER INFORMATION: Upstream primer of the second round of PCR

<400> SEQUENCE: 112
catgccatga ctgtggccca ggcggcccag ktgcagctcg tggagtc                47

<210> SEQ ID NO 113
<211> LENGTH: 51
<212> TYPE: DNA
<213> ORGANISM: Artificial Sequence
<220> FEATURE:
<223> OTHER INFORMATION: Downstream primer of the second round of PCR

<400> SEQUENCE: 113
catgccatga ctcgcggccg gcctggccat gggggtcttc gctgtggtgc g           51

<210> SEQ ID NO 114
<211> LENGTH: 52
<212> TYPE: DNA
<213> ORGANISM: Artificial Sequence
<220> FEATURE:
<223> OTHER INFORMATION: Downstream primer of the second round of PCR

<400> SEQUENCE: 114
catgccatga ctcgcggccg gcctggccgt cttgtggttt tggtgtcttg gg          52

<210> SEQ ID NO 115
<211> LENGTH: 51
<212> TYPE: DNA
<213> ORGANISM: Artificial Sequence
<220> FEATURE:
<223> OTHER INFORMATION: Upstream primer

<400> SEQUENCE: 115
gtttaacttt aagaaggaga tatacatatg caggtgcagc tcgtggagtc t           51

<210> SEQ ID NO 116
<211> LENGTH: 58
<212> TYPE: DNA
<213> ORGANISM: Artificial Sequence
<220> FEATURE:

<223> OTHER INFORMATION: Downstream primer

<400> SEQUENCE: 116

```
ggccgcaagc ttgtcgacgg agctcgaatt cttactaatg gtgatggtga tggtgctg        58
```

<210> SEQ ID NO 117
<211> LENGTH: 53
<212> TYPE: DNA
<213> ORGANISM: Artificial Sequence
<220> FEATURE:
<223> OTHER INFORMATION: Upstream primer

<400> SEQUENCE: 117

```
gtgctgctgc tgtgggtgcc aggatccacc gggcaggtgc agctcgtgga gtc             53
```

<210> SEQ ID NO 118
<211> LENGTH: 45
<212> TYPE: DNA
<213> ORGANISM: Artificial Sequence
<220> FEATURE:
<223> OTHER INFORMATION: Downstream primer

<400> SEQUENCE: 118

```
gcaggacttg ggctcagaag acacggtgac cagggtcccc tggcc                      45
```

<210> SEQ ID NO 119
<211> LENGTH: 1056
<212> TYPE: DNA
<213> ORGANISM: Artificial Sequence
<220> FEATURE:
<223> OTHER INFORMATION: Nucleic acid sequence of the isolated
      polynucleotide

<400> SEQUENCE: 119

```
caggtgcagc tcgtggagtc tgggggaggc ttggtgcagc ctggggggtc tctgagactc        60
tcctgtgcag cctctggggg catcttcagt atcggtgtca tgggctggta ccgccaggct       120
ccagggaagc agcgcgaatt ggtcgcgact attactagtc gtggtagcac aaactatgca       180
gactccgtga agggccgatt caccatctcc ggagacaacg ccaagaacac ggtgtatcta       240
caaatgaaca acctgaaacc tgaggacacg gccgtctatt actgttatgc agatctcata       300
agacccggtg atttctacgg catggactac tggggccagg ggaccctggt caccgtgtct       360
tctgagccca gtcctgcga caaaactcac acatgcccac cgtgcccagc acctgaactc       420
ctgggtggac cgtcagtctt cctcttcccc ccaaaaccca aggacaccct catgatctcc       480
cggacccctg aggtcacatg cgtggtggtg gacgtgagcc acgaagaccc tgaggtcaag       540
ttcaactggt acgtggacgg cgtggaggtg cataatgcca agacaaagcc gcgggaggag       600
cagtacaata gcacgtaccg tgtggtcagc gtcctcaccg tcctgcacca ggactggctg       660
aatggcaagg agtacaagtg caaggtctcc aacaaagccc tcccagcccc catcgagaaa       720
accatctcca agccaaagg gcagccccga gaaccacagg tgtacaccct gcccccatcc       780
cgggatgagc tgaccaagaa ccaggtcagc ctgacctgcc tggtcaaagg cttctatccc       840
agcgacatcg ccgtggagtg ggagagcaat gggcagccgg agaacaacta caagaccacg       900
cctcccgtgc tggactccga cggctccttc ttcctctata gcaagctcac cgtggacaag       960
agcaggtggc agcaggggaa cgtcttctca tgctccgtga tgcatgaggc tctgcacaac      1020
cactacacgc agaagagcct ctccctgtct ccgggt                                1056
```

<210> SEQ ID NO 120

<211> LENGTH: 1059
<212> TYPE: DNA
<213> ORGANISM: Artificial Sequence
<220> FEATURE:
<223> OTHER INFORMATION: Nucleic acid sequence of the isolated polynucleotide

<400> SEQUENCE: 120

| | |
|---|---|
| caggtgcagc tcgtggagtc tgggggaggc ttggtgcagc ctgggggtc tctgagactc | 60 |
| tcctgtgcag cctctggaag catcttcctt atcaatgcca tgggctggta ccgccaggct | 120 |
| ccagggaagc agcgcgagtt ggtcgcagtt attactagag gtggtagcgc aaactataca | 180 |
| gactccgtga agggccgatt caccatctcc agagacaacg ccaagaatac ggtgtatctg | 240 |
| caaatgaaca gcctgaaacc tgaggacacg gccgtctatt actgtaatgc agatttgaac | 300 |
| ttaaggagcg accccttta atggtatacg ttttggggcc aggggaccct ggtcaccgtg | 360 |
| tcttctgagc ccaagtcctg cgacaaaact cacacatgcc caccgtgccc agcacctgaa | 420 |
| ctcctgggtg gaccgtcagt cttcctcttc cccccaaaac ccaaggacac cctcatgatc | 480 |
| tcccggaccc ctgaggtcac atgcgtggtg gtggacgtga gccacgaaga ccctgaggtc | 540 |
| aagttcaact ggtacgtgga cggcgtggag gtgcataatg ccaagacaaa gccgcgggag | 600 |
| gagcagtaca atagcacgta ccgtgtggtc agcgtcctca ccgtcctgca ccaggactgg | 660 |
| ctgaatggca aggagtacaa gtgcaaggtc tccaacaaag ccctcccagc ccccatcgag | 720 |
| aaaaccatct ccaaagccaa agggcagccc cgagaaccac aggtgtacac cctgcccca | 780 |
| tcccgggatg agctgaccaa gaaccaggtc agcctgacct gcctggtcaa aggcttctat | 840 |
| cccagcgaca tcgccgtgga gtgggagagc aatgggcagc cggagaacaa ctacaagacc | 900 |
| acgcctcccg tgctggactc cgacggctcc ttcttcctct atagcaagct caccgtggac | 960 |
| aagagcaggt ggcagcaggg gaacgtcttc tcatgctccg tgatgcatga ggctctgcac | 1020 |
| aaccactaca cgcagaagag cctctcctg tctccgggt | 1059 |

<210> SEQ ID NO 121
<211> LENGTH: 1056
<212> TYPE: DNA
<213> ORGANISM: Artificial Sequence
<220> FEATURE:
<223> OTHER INFORMATION: Nucleic acid sequence of the isolated polynucleotide

<400> SEQUENCE: 121

| | |
|---|---|
| caggtgcagc tcgtggagtc tgggggaggc ttggtgcagc ctgggggtc tctaagactc | 60 |
| tcctgtacag cctctggaag catcttcagg atcgatggca tgcattggta ccgccaggct | 120 |
| ccagggaagc agcgcgagtt ggtcgcaagt attactccta gtggtatcac ccactatgca | 180 |
| gactccgtga agggccgatt caccatctcc agagacatcg ccaagaaaat gcagtatctg | 240 |
| caaatgaaca gcctgaaacc tgaggacacg gccgtctatt actgtaatgc acacctcgtc | 300 |
| aaagttggcg gagtttggag tgatgagtac tggggccagg gaccctggt caccgtgtct | 360 |
| tctgagccca gtcctgcga caaaactcac acatgcccac cgtgcccagc acctgaactc | 420 |
| ctgggtggac cgtcagtctt cctcttcccc ccaaaaccca aggacaccct catgatctcc | 480 |
| cggacccctg aggtcacatg cgtggtggtg gacgtgagcc acgaagaccc tgaggtcaag | 540 |
| ttcaactggt acgtggacgg cgtggaggtg cataatgcca agacaaagcc gcgggaggag | 600 |
| cagtacaata gcacgtaccg tgtggtcagc gtcctcaccg tcctgcacca ggactggctg | 660 |
| aatggcaagg agtacaagtg caaggtctcc aacaaagccc tcccagcccc catcgagaaa | 720 |

```
accatctcca aagccaaagg gcagccccga gaaccacagg tgtacaccct gcccccatcc    780
cgggatgagc tgaccaagaa ccaggtcagc ctgacctgcc tggtcaaagg cttctatccc    840
agcgacatcg ccgtggagtg ggagagcaat gggcagccgg agaacaacta caagaccacg    900
cctcccgtgc tggactccga cggctccttc ttcctctata gcaagctcac cgtggacaag    960
agcaggtggc agcaggggaa cgtcttctca tgctccgtga tgcatgaggc tctgcacaac   1020
cactacacgc agaagagcct ctccctgtct ccgggt                             1056
```

<210> SEQ ID NO 122
<211> LENGTH: 1053
<212> TYPE: DNA
<213> ORGANISM: Artificial Sequence
<220> FEATURE:
<223> OTHER INFORMATION: Nucleic acid sequence of the isolated
      polynucleotide

<400> SEQUENCE: 122

```
caggtgcagc tcgtggagtc tgggggaggc ttggtgcagc ctggggggtc tctgagactc     60
tcctgtgcag cctctggagt cgacatcagt agcgatgtca tggcctggta ccgccaggct    120
ccagggaagc agcgcgagtt tgtctcaggc cttactagag tggtagcat aaactatgca    180 gactccgtga agggccgatt caccatctcc agagacttcg ccaagaacac ggtagatctg    240
caaatgaaca gcctgaaacc tgaggacacg gccgtctatt actgtaatgc agaaatctat    300
actggtactt tctacccgag gtcctactgg ggccagggga ccctggtcac cgtgtcttct    360
gagcccaagt cctgcgacaa aactcacaca tgcccaccgt gcccagcacc tgaactcctg    420
ggtggaccgt cagtcttcct cttccccca aaacccaagg acaccctcat gatctcccgg    480
acccctgagg tcacatgcgt ggtggtggac gtgagccacg aagaccctga ggtcaagttc    540
aactggtacg tggacggcgt ggaggtgcat aatgccaaga caaagccgcg ggaggagcag    600
tacaatagca cgtaccgtgt ggtcagcgtc ctcaccgtcc tgcaccagga ctggctgaat    660
ggcaaggagt acaagtgcaa ggtctccaac aaagccctcc cagcccccat cgagaaaacc    720
atctccaaag ccaaagggca gccccgagaa ccacaggtgt acaccctgcc cccatcccgg    780
gatgagctga ccaagaacca ggtcagcctg acctgcctgg tcaaaggctt ctatcccagc    840
gacatcgccg tggagtggga gagcaatggg cagccggaga caactacaa gaccacgcct    900 cccgtgctgg actccgacgg ctccttcttc ctctatagca agctcaccgt ggacaagagc    960
aggtggcagc aggggaacgt cttctcatgc tccgtgatgc atgaggctct gcacaaccac   1020
tacacgcaga agagcctctc cctgtctccg ggt                                1053
```

<210> SEQ ID NO 123
<211> LENGTH: 1059
<212> TYPE: DNA
<213> ORGANISM: Artificial Sequence
<220> FEATURE:
<223> OTHER INFORMATION: Nucleic acid sequence of the isolated
      polynucleotide

<400> SEQUENCE: 123

```
caggtgcagc tcgtggagtc tgggggagga ttggtgcagc ctggggggtc tctgagactc     60
tcctgtgcag cctctggaag catcttcagt atcaatgcca tgggctggta ccgccaggct    120
ccagggaagc agcgcgagtt ggtcgcagca attacttttg gtggtggtag cacaaactat    180
gcagactccg tgaagggccg attcaccatc tccagagaca acgccaagaa cacggtgtat    240
```

| | |
|---|---|
| ctgcaaatga acagcctgaa acctgaggac acggccgtct attactgtaa tgcagatctc | 300 |
| ctggtaggtg gatttccgag gcggaatgtc tactggggcc aggggaccct ggtcaccgtg | 360 |
| tcttctgagc ccaagtcctg cgacaaaact cacacatgcc caccgtgccc agcacctgaa | 420 |
| ctcctgggtg gaccgtcagt cttcctcttc cccccaaaac ccaaggacac cctcatgatc | 480 |
| tcccggaccc ctgaggtcac atgcgtggtg gtggacgtga gccacgaaga ccctgaggtc | 540 |
| aagttcaact ggtacgtgga cggcgtggag gtgcataatg ccaagacaaa gccgcgggag | 600 |
| gagcagtaca atagcacgta ccgtgtggtc agcgtcctca ccgtcctgca ccaggactgg | 660 |
| ctgaatggca aggagtacaa gtgcaaggtc tccaacaaag ccctcccagc ccccatcgag | 720 |
| aaaaccatct ccaaagccaa agggcagccc cgagaaccac aggtgtacac cctgccccca | 780 |
| tcccgggatg agctgaccaa gaaccaggtc agcctgacct gcctggtcaa aggcttctat | 840 |
| cccagcgaca tcgccgtgga gtgggagagc aatgggcagc cggagaacaa ctacaagacc | 900 |
| acgcctcccg tgctggactc cgacggctcc ttcttcctct atagcaagct caccgtggac | 960 |
| aagagcaggt ggcagcaggg gaacgtcttc tcatgctccg tgatgcatga ggctctgcac | 1020 |
| aaccactaca cgcagaagag cctctccctg tctccgggt | 1059 |

<210> SEQ ID NO 124
<211> LENGTH: 1059
<212> TYPE: DNA
<213> ORGANISM: Artificial Sequence
<220> FEATURE:
<223> OTHER INFORMATION: Nucleic acid sequence of the isolated polynucleotide

<400> SEQUENCE: 124

| | |
|---|---|
| caggtgcagc tcgtggagtc tgggggaggt ttggtgcagc ctgggggtc tctgagactc | 60 |
| tcctgtgcag cctctggaag catcttcatg atcaatgtca tgggctggta ccgccaggct | 120 |
| ccagggaagc agcgcgagtt ggtcgcagtt attactagag gtgctagcac aaactatgca | 180 |
| gactccgtga agggccgatt caccatctcc agagacaacg ccaagaatac ggtctatctg | 240 |
| caaatgaaca gcctgaaacc tgaggacacg gccgtctatt actgtaatgc agatttgaac | 300 |
| ttagcgagcg accccttaa atggtatacg tattggggcc aggggaccct ggtcaccgtg | 360 |
| tcttctgagc ccaagtcctg cgacaaaact cacacatgcc caccgtgccc agcacctgaa | 420 |
| ctcctgggtg gaccgtcagt cttcctcttc cccccaaaac ccaaggacac cctcatgatc | 480 |
| tcccggaccc ctgaggtcac atgcgtggtg gtggacgtga gccacgaaga ccctgaggtc | 540 |
| aagttcaact ggtacgtgga cggcgtggag gtgcataatg ccaagacaaa gccgcgggag | 600 |
| gagcagtaca atagcacgta ccgtgtggtc agcgtcctca ccgtcctgca ccaggactgg | 660 |
| ctgaatggca aggagtacaa gtgcaaggtc tccaacaaag ccctcccagc ccccatcgag | 720 |
| aaaaccatct ccaaagccaa agggcagccc cgagaaccac aggtgtacac cctgccccca | 780 |
| tcccgggatg agctgaccaa gaaccaggtc agcctgacct gcctggtcaa aggcttctat | 840 |
| cccagcgaca tcgccgtgga gtgggagagc aatgggcagc cggagaacaa ctacaagacc | 900 |
| acgcctcccg tgctggactc cgacggctcc ttcttcctct atagcaagct caccgtggac | 960 |
| aagagcaggt ggcagcaggg gaacgtcttc tcatgctccg tgatgcatga ggctctgcac | 1020 |
| aaccactaca cgcagaagag cctctccctg tctccgggt | 1059 |

<210> SEQ ID NO 125
<211> LENGTH: 1050
<212> TYPE: DNA

<213> ORGANISM: Artificial Sequence
<220> FEATURE:
<223> OTHER INFORMATION: Nucleic acid sequence of the isolated polynucleotide

<400> SEQUENCE: 125

```
caggtgcagc tcgtggagtc tggggggaggc ttggtgcagc ctggggggtc tctgagactc    60
tcctgtgcag cctctggaga aatcagtagc gatgccatgg cctggtaccg ccaggctcca   120
gggaaacagc gcgagttggt cgcaggtatg actagaggtg gtagcacaaa ctatgcagac   180
tccgtgaagg gccgattcac catctccaga gacttcgcca agaacacggt agatctgcaa   240
atgaacagct gaaacctga ggacacggcc gtctattact gtaatgcaga aatctatact   300
ggtactttct acccgaggtc ctactggggc caggggaccc tggtcaccgt gtcttctgag   360
cccaagtcct gcgacaaaac tcacacatgc ccaccgtgcc cagcacctga actcctgggt   420
ggaccgtcag tcttcctctt ccccccaaaa cccaaggaca ccctcatgat ctcccggacc   480
cctgaggtca catgcgtggt ggtggacgtg agccacgaag accctgaggt caagttcaac   540
tggtacgtgg acggcgtgga ggtgcataat gccaagacaa agccgcggga ggagcagtac   600
aatagcacgt accgtgtggt cagcgtcctc accgtcctgc accaggactg gctgaatggc   660
aaggagtaca agtgcaaggt ctccaacaaa gccctcccag cccccatcga gaaaaccatc   720
tccaaagcca agggcagcc ccgagaacca caggtgtaca ccctgccccc atcccgggat   780
gagctgacca agaaccaggt cagcctgacc tgcctggtca aaggcttcta tcccagcgac   840
atcgccgtgg agtgggagag caatgggcag ccggagaaca actacaagac cacgcctccc   900
gtgctggact ccgacggctc cttcttcctc tatagcaagc tcaccgtgga caagagcagg   960
tggcagcagg ggaacgtctt ctcatgctcc gtgatgcatg aggctctgca caaccactac  1020
acgcagaaga gcctctccct gtctccgggt                                   1050
```

<210> SEQ ID NO 126
<211> LENGTH: 1056
<212> TYPE: DNA
<213> ORGANISM: Artificial Sequence
<220> FEATURE:
<223> OTHER INFORMATION: Nucleic acid sequence of the isolated polynucleotide

<400> SEQUENCE: 126

```
caggtgcagc tcgtggagtc cggggggaggc ttggtgcagc ctggggggtc tctgagactc    60
tcctgtgcag cctctggaag catcttcagt atccctgtca tgacctggta ccgccaggct   120
ctagggaaag agcgcgagtt cgtcgcaggt attagtaagg gtggtacctc gaactatgca   180
gactccgtga agggccgatt caccgtctcc agagacaacg ccaagaacac ggtgtatctg   240
caaatgaaca gcctgaaatc agaggacacg gccgtctatt actgcaatgc acaagcttct   300
tcgttcggtt ggatgcccct ctctgactac tggggccagg ggaccctggt caccgtgtct   360
tctgagccca gtcctgcga caaaactcac acatgcccac cgtgcccagc acctgaactc   420
ctgggtggac cgtcagtctt cctcttcccc ccaaaaccca aggacaccct catgatctcc   480
cggacccctg aggtcacatg cgtggtggtg gacgtgagcc acgaagaccc tgaggtcaag   540
ttcaactggt acgtggacgg cgtggaggtg cataatgcca agacaaagcc gcgggaggag   600
cagtacaata gcacgtaccg tgtggtcagc gtcctcaccg tcctgccaa ggactggctg   660
aatggcaagg agtacaagtg caaggtctcc aacaaagccc tccagcccc catcgagaaa   720
accatctccaa agccaaagg gcagccccga gaaccacagg tgtacaccct gccccatcc   780
```

| | |
|---|---:|
| cgggatgagc tgaccaagaa ccaggtcagc ctgacctgcc tggtcaaagg cttctatccc | 840 |
| agcgacatcg ccgtggagtg ggagagcaat gggcagccgg agaacaacta caagaccacg | 900 |
| cctcccgtgc tggactccga cggctccttc ttcctctata gcaagctcac cgtggacaag | 960 |
| agcaggtggc agcaggggaa cgtcttctca tgctccgtga tgcatgaggc tctgcacaac | 1020 |
| cactacacgc agaagagcct ctccctgtct ccgggt | 1056 |

<210> SEQ ID NO 127
<211> LENGTH: 1056
<212> TYPE: DNA
<213> ORGANISM: Artificial Sequence
<220> FEATURE:
<223> OTHER INFORMATION: Nucleic acid sequence of the isolated polynucleotide

<400> SEQUENCE: 127

| | |
|---|---:|
| caggtgcagc tcgtggagtc tgggggaggc ttggtgcagc ctggggggtc tctgagactc | 60 |
| tcctgtgcag cctctggggg catcttcagt atcggtgtca tgggctgggt cgcgcaggct | 120 |
| ccagggaagg gcctggagtg ggtcgcgact attactagtc gtggtagcac aaactatgca | 180 |
| gactccgtga agggccgatt caccatctcc agagacaaca gcaagaacac gctgtatcta | 240 |
| caaatgaaca gcctgcgggc cgaggacacg gccgtctatt actgttatgc agatctcata | 300 |
| agacccggtg atttctacgg catggactac tggggccagg ggaccctggt caccgtgtct | 360 |
| tctgagccca gtcctgcga caaaactcac acatgcccac cgtgcccagc acctgaactc | 420 |
| ctgggtggac cgtcagtctt cctcttcccc ccaaaaccca aggacaccct catgatctcc | 480 |
| cggacccctg aggtcacatg cgtggtggtg gacgtgagcc acgaagaccc tgaggtcaag | 540 |
| ttcaactggt acgtggacgg cgtggaggtg cataatgcca agacaaagcc gcgggaggag | 600 |
| cagtacaata gcacgtaccg tgtggtcagc gtcctcaccg tcctgcacca ggactggctg | 660 |
| aatggcaagg agtacaagtg caaggtctcc aacaaagccc tcccagcccc catcgagaaa | 720 |
| accatctcca aagccaaagg gcagccccga gaaccacagg tgtacaccct gcccccatcc | 780 |
| cgggatgagc tgaccaagaa ccaggtcagc ctgacctgcc tggtcaaagg cttctatccc | 840 |
| agcgacatcg ccgtggagtg ggagagcaat gggcagccgg agaacaacta caagaccacg | 900 |
| cctcccgtgc tggactccga cggctccttc ttcctctata gcaagctcac cgtggacaag | 960 |
| agcaggtggc agcaggggaa cgtcttctca tgctccgtga tgcatgaggc tctgcacaac | 1020 |
| cactacacgc agaagagcct ctccctgtct ccgggt | 1056 |

<210> SEQ ID NO 128
<211> LENGTH: 1056
<212> TYPE: DNA
<213> ORGANISM: Artificial Sequence
<220> FEATURE:
<223> OTHER INFORMATION: Nucleic acid sequence of the isolated polynucleotide

<400> SEQUENCE: 128

| | |
|---|---:|
| caggtgcagc tcgtggagtc tgggggaggc ttggtgcagc ctggggggtc tctgagactc | 60 |
| tcctgtgcag cctctggggg catcttcagt atcggtgtca tgggctggta ccgccaggct | 120 |
| ccagggaagg gcctggagct ggtcgcgact attactagtc gtggtagcac aaactatgca | 180 |
| gactccgtga agggccgatt caccatctcc agagacaaca gcaagaacac gctgtatcta | 240 |
| caaatgaaca gcctgcgggc cgaggacacg gccgtctatt actgttatgc agatctcata | 300 |

```
agacccggtg atttctacgg catggactac tggggccagg ggaccctggt caccgtgtct     360
tctgagccca gtcctgcgca caaaactcac acatgcccac cgtgcccagc acctgaactc     420
ctgggtggac cgtcagtctt cctcttcccc ccaaaaccca aggacaccct catgatctcc     480
cggacccctg aggtcacatg cgtggtggtg gacgtgagcc acgaagaccc tgaggtcaag     540
ttcaactggt acgtggacgg cgtggaggtg cataatgcca agacaaagcc gcgggaggag     600
cagtacaata gcacgtaccg tgtggtcagc gtcctcaccg tcctgcacca ggactggctg     660
aatggcaagg agtacaagtg caaggtctcc aacaaagccc tcccagcccc catcgagaaa     720
accatctcca aagccaaagg gcagccccga gaaccacagg tgtacaccct gcccccatcc     780
cgggatgagc tgaccaagaa ccaggtcagc ctgacctgcc tggtcaaagg cttctatccc     840
agcgacatcg ccgtggagtg ggagagcaat gggcagccgg agaacaacta caagaccacg     900
cctcccgtgc tggactccga cggctccttc ttcctctata gcaagctcac cgtggacaag     960
agcaggtggc agcaggggaa cgtcttctca tgctccgtga tgcatgaggc tctgcacaac    1020
cactacacgc agaagagcct ctccctgtct ccgggt                              1056
```

<210> SEQ ID NO 129
<211> LENGTH: 1053
<212> TYPE: DNA
<213> ORGANISM: Artificial Sequence
<220> FEATURE:
<223> OTHER INFORMATION: Nucleic acid sequence of the isolated
      polynucleotide

<400> SEQUENCE: 129

```
caggtgcagc tcgtggagtc tgggggaggc ttggtgcagc ctggggggtc tctgagactc      60
tcctgtgcag cctctggagt cgacatcagt agcgatgtca tggcctggta ccgccaggct     120
ccagggaagc agcgggagtt cgtctcaggc cttactagag gtggtagcat aaactatgca     180
gactccgtga agggccgatt caccatctcc agagacaaca gcaagaacac gctgtacctg     240
caaatgaaca gcctgagagc cgaggacacg gccgtctatt actgtaatgc agaaatctat     300
actggtactt tctacccgag gtcctactgg ggccagggga ccctggtcac cgtgtcttct     360
gagcccaagt cctgcgacaa aactcacaca tgcccaccgt gcccagcacc tgaactcctg     420
ggtggaccgt cagtcttcct cttcccccca aaacccaagg acaccctcat gatctcccgg     480
acccctgagg tcacatgcgt ggtggtggac gtgagccacg aagaccctga ggtcaagttc     540
aactggtacg tggacggcgt ggaggtgcat aatgccaaga caaagccgcg ggaggagcag     600
tacaatagca cgtaccgtgt ggtcagcgtc ctcaccgtcc tgcaccagga ctggctgaat     660
ggcaaggagt acaagtgcaa ggtctccaac aaagccctcc cagcccccat cgagaaaacc     720
atctccaaag ccaagggca gccccgagaa ccacaggtgt acaccctgcc ccatcccgg     780 gatgagctga ccaagaacca ggtcagcctg acctgcctgg tcaaaggctt ctatcccagc     840
gacatcgccg tggagtggga gagcaatggg cagccggaga caactacaa gaccacgcct     900 cccgtgctgg actccgacgg ctccttcttc ctctatagca agctcaccgt ggacaagagc     960
aggtggcagc aggggaacgt cttctcatgc tccgtgatgc atgaggctct gcacaaccac    1020
tacacgcaga agagcctctc cctgtctccg ggt                                 1053
```

<210> SEQ ID NO 130
<211> LENGTH: 1053
<212> TYPE: DNA
<213> ORGANISM: Artificial Sequence
<220> FEATURE:

<223> OTHER INFORMATION: Nucleic acid sequence of the isolated polynucleotide

<400> SEQUENCE: 130

```
caggtgcagc tcgtggagtc tgggggaggc ttggtgcagc ctggggggtc tctgagactc      60
tcctgtgcag cctctggagt cgacatcagt agcgatgtca tggcctggta ccgccaggct     120
ccagggaagg gcctggagtt cgtctcaggc cttactagag gtggtagcat aaactatgca     180
gactccgtga agggccgatt caccatctcc agagacaaca gcaagaacac gctgtacctg     240
caaatgaaca gcctgagagc cgaggacacg gccgtctatt actgtaatgc agaaatctat     300
actggtactt tctacccgag gtcctactgg ggccagggga ccctggtcac cgtgtcttct     360
gagcccaagt cctgcgacaa aactcacaca tgcccaccgt gcccagcacc tgaactcctg     420
ggtggaccgt cagtcttcct cttcccccca aaacccaagg acaccctcat gatctcccgg     480
acccctgagg tcacatgcgt ggtggtggac gtgagccacg aagaccctga ggtcaagttc     540
aactggtacg tggacggcgt ggaggtgcat aatgccaaga caaagccgcg ggaggagcag     600
tacaatagca cgtaccgtgt ggtcagcgtc ctcaccgtcc tgcaccagga ctggctgaat     660
ggcaaggagt acaagtgcaa ggtctccaac aaagcccctc cagcccccat cgagaaaacc     720
atctccaaag ccaaagggca gccccgagaa ccacaggtgt acaccctgcc cccatcccgg     780
gatgagctga ccaagaacca ggtcagcctg acctgcctgg tcaaaggctt ctatcccagc     840
gacatcgccg tggagtggga gagcaatggg cagccggaga caactacaa gaccacgcct     900
cccgtgctgg actccgacgg ctccttcttc ctctatagca agctcaccgt ggacaagagc     960
aggtggcagc aggggaacgt cttctcatgc tccgtgatgc atgaggctct gcacaaccac    1020
tacacgcaga gagcctctc cctgtctccg ggt                                  1053
```

<210> SEQ ID NO 131
<211> LENGTH: 124
<212> TYPE: PRT
<213> ORGANISM: Artificial Sequence
<220> FEATURE:
<223> OTHER INFORMATION: Amino acid sequence of anti-CD3 nanobody

<400> SEQUENCE: 131

```
Glu Val Gln Leu Val Glu Ser Gly Gly Gly Pro Val Gln Ala Gly Gly
1               5                   10                  15
Ser Leu Arg Leu Ser Cys Ala Ala Ser Gly Arg Thr Tyr Arg Gly Tyr
            20                  25                  30
Ser Met Gly Trp Phe Arg Gln Ala Pro Gly Lys Glu Arg Glu Phe Val
        35                  40                  45
Ala Ala Ile Val Trp Ser Gly Gly Asn Thr Tyr Tyr Glu Asp Ser Val
    50                  55                  60
Lys Gly Arg Phe Thr Ile Ser Arg Asp Asn Ala Lys Asn Thr Met Tyr
65                  70                  75                  80
Leu Gln Met Thr Ser Leu Lys Pro Glu Asp Ser Ala Thr Tyr Tyr Cys
                85                  90                  95
Ala Ala Lys Ile Arg Pro Tyr Ile Phe Lys Ile Ala Gly Gln Tyr Asp
            100                 105                 110
Tyr Trp Gly Gln Gly Thr Gln Val Thr Val Ser Ser
        115                 120
```

<210> SEQ ID NO 132
<211> LENGTH: 35
<212> TYPE: PRT

<213> ORGANISM: Artificial Sequence
<220> FEATURE:
<223> OTHER INFORMATION: GS sequence

<400> SEQUENCE: 132

```
Gly Gly Gly Gly Ser Gly Gly Gly Ser Gly Gly Gly Ser Gly
1               5                  10                  15

Gly Gly Gly Ser Gly Gly Gly Ser Gly Gly Gly Ser Gly Gly
                20              25              30

Gly Gly Ser
        35
```

<210> SEQ ID NO 133
<211> LENGTH: 280
<212> TYPE: PRT
<213> ORGANISM: Artificial Sequence
<220> FEATURE:
<223> OTHER INFORMATION: Amino acid sequence of Anti-CLDN18xCD3-hu6V3

<400> SEQUENCE: 133

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Phe Ser Ile Gly
            20                  25                  30

Val Met Gly Trp Tyr Arg Gln Ala Pro Gly Lys Gly Leu Glu Leu Val
        35                  40                  45

Ala Thr Ile Thr Ser Arg Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Asp Leu Ile Arg Pro Gly Asp Phe Tyr Gly Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Ser Gly Gly Gly Ser Glu Val Gln Leu
145                 150                 155                 160

Val Glu Ser Gly Gly Gly Pro Val Gln Ala Gly Gly Ser Leu Arg Leu
                165                 170                 175

Ser Cys Ala Ala Ser Gly Arg Thr Tyr Arg Gly Tyr Ser Met Gly Trp
            180                 185                 190

Phe Arg Gln Ala Pro Gly Lys Glu Arg Glu Phe Val Ala Ala Ile Val
        195                 200                 205

Trp Ser Gly Gly Asn Thr Tyr Tyr Glu Asp Ser Val Lys Gly Arg Phe
    210                 215                 220

Thr Ile Ser Arg Asp Asn Ala Lys Asn Thr Met Tyr Leu Gln Met Thr
225                 230                 235                 240

Ser Leu Lys Pro Glu Asp Ser Ala Thr Tyr Tyr Cys Ala Ala Lys Ile
                245                 250                 255

Arg Pro Tyr Ile Phe Lys Ile Ala Gly Gln Tyr Asp Tyr Trp Gly Gln
            260                 265                 270

Gly Thr Gln Val Thr Val Ser Ser
        275                 280
```

```
<210> SEQ ID NO 134
<211> LENGTH: 279
<212> TYPE: PRT
<213> ORGANISM: Artificial Sequence
<220> FEATURE:
<223> OTHER INFORMATION: Amino acid sequence of Anti-CLDN18xCD3-hu19V3

<400> SEQUENCE: 134

Gln Val Gln Leu Val Glu Ser Gly Gly Gly Leu Val Gln Pro Gly Gly
1               5                   10                  15

Ser Leu Arg Leu Ser Cys Ala Ala Ser Gly Val Asp Ile Ser Ser Asp
            20                  25                  30

Val Met Ala Trp Tyr Arg Gln Ala Pro Gly Lys Gly Leu Glu Phe Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Pro Val Gln Ala Gly Gly Ser Leu Arg Leu Ser
                165                 170                 175

Cys Ala Ala Ser Gly Arg Thr Tyr Arg Gly Tyr Ser Met Gly Trp Phe
            180                 185                 190

Arg Gln Ala Pro Gly Lys Glu Arg Glu Phe Val Ala Ala Ile Val Trp
        195                 200                 205

Ser Gly Gly Asn Thr Tyr Tyr Glu Asp Ser Val Lys Gly Arg Phe Thr
    210                 215                 220

Ile Ser Arg Asp Asn Ala Lys Asn Thr Met Tyr Leu Gln Met Thr Ser
225                 230                 235                 240

Leu Lys Pro Glu Asp Ser Ala Thr Tyr Tyr Cys Ala Ala Lys Ile Arg
                245                 250                 255

Pro Tyr Ile Phe Lys Ile Ala Gly Gln Tyr Asp Tyr Trp Gly Gln Gly
            260                 265                 270

Thr Gln Val Thr Val Ser Ser
        275

<210> SEQ ID NO 135
<211> LENGTH: 226
<212> TYPE: PRT
<213> ORGANISM: Artificial Sequence
<220> FEATURE:
<223> OTHER INFORMATION: Amino acid sequence of CD8 hinge-CD28a-CD28b-
      CD3?

<400> SEQUENCE: 135

Thr Thr Thr Pro Ala Pro Arg Pro Pro Thr Pro Ala Pro Thr Ile Ala
1               5                   10                  15
```

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Phe Trp Val
            35                  40                  45

Leu Val Val Val Gly Gly Val Leu Ala Cys Tyr Ser Leu Leu Val Thr
50                  55                  60

Val Ala Phe Ile Ile Phe Trp Val Arg Ser Lys Arg Ser Arg Leu Leu
65                  70                  75                  80

His Ser Asp Tyr Met Asn Met Thr Pro Arg Arg Pro Gly Pro Thr Arg
                85                  90                  95

Lys His Tyr Gln Pro Tyr Ala Pro Pro Arg Asp Phe Ala Ala Tyr Arg
            100                 105                 110

Ser Arg Val Lys Phe Ser Arg Ser Ala Asp Ala Pro Ala Tyr Gln Gln
            115                 120                 125

Gly Gln Asn Gln Leu Tyr Asn Glu Leu Asn Leu Gly Arg Arg Glu Glu
130                 135                 140

Tyr Asp Val Leu Asp Lys Arg Arg Gly Arg Asp Pro Glu Met Gly Gly
145                 150                 155                 160

Lys Pro Gln Arg Arg Lys Asn Pro Gln Glu Gly Leu Tyr Asn Glu Leu
            165                 170                 175

Gln Lys Asp Lys Met Ala Glu Ala Tyr Ser Glu Ile Gly Met Lys Gly
            180                 185                 190

Glu Arg Arg Arg Gly Lys Gly His Asp Gly Leu Tyr Gln Gly Leu Ser
            195                 200                 205

Thr Ala Thr Lys Asp Thr Tyr Asp Ala Leu His Met Gln Ala Leu Pro
            210                 215                 220

Pro Arg
225

<210> SEQ ID NO 136
<211> LENGTH: 268
<212> TYPE: PRT
<213> ORGANISM: Artificial Sequence
<220> FEATURE:
<223> OTHER INFORMATION: Amino acid sequence of CD8 hinge-CD28a-CD28b-
      CD137- CD3?

<400> SEQUENCE: 136

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Phe Trp Val
            35                  40                  45

Leu Val Val Val Gly Gly Val Leu Ala Cys Tyr Ser Leu Leu Val Thr
50                  55                  60

Val Ala Phe Ile Ile Phe Trp Val Arg Ser Lys Arg Ser Arg Leu Leu
65                  70                  75                  80

His Ser Asp Tyr Met Asn Met Thr Pro Arg Arg Pro Gly Pro Thr Arg
                85                  90                  95

Lys His Tyr Gln Pro Tyr Ala Pro Pro Arg Asp Phe Ala Ala Tyr Arg
            100                 105                 110

Ser Lys Arg Gly Arg Lys Lys Leu Leu Tyr Ile Phe Lys Gln Pro Phe
            115                 120                 125

```
Met Arg Pro Val Gln Thr Thr Gln Glu Glu Asp Gly Cys Ser Cys Arg
    130                 135                 140

Phe Pro Glu Glu Glu Glu Gly Gly Cys Glu Leu Arg Val Lys Phe Ser
145                 150                 155                 160

Arg Ser Ala Asp Ala Pro Ala Tyr Gln Gln Gly Gln Asn Gln Leu Tyr
                165                 170                 175

Asn Glu Leu Asn Leu Gly Arg Arg Glu Glu Tyr Asp Val Leu Asp Lys
            180                 185                 190

Arg Arg Gly Arg Asp Pro Glu Met Gly Gly Lys Pro Gln Arg Arg Lys
        195                 200                 205

Asn Pro Gln Glu Gly Leu Tyr Asn Glu Leu Gln Lys Asp Lys Met Ala
    210                 215                 220

Glu Ala Tyr Ser Glu Ile Gly Met Lys Gly Glu Arg Arg Arg Gly Lys
225                 230                 235                 240

Gly His Asp Gly Leu Tyr Gln Gly Leu Ser Thr Ala Thr Lys Asp Thr
                245                 250                 255

Tyr Asp Ala Leu His Met Gln Ala Leu Pro Pro Arg
            260                 265

<210> SEQ ID NO 137
<211> LENGTH: 347
<212> TYPE: PRT
<213> ORGANISM: Artificial Sequence
<220> FEATURE:
<223> OTHER INFORMATION: Amino acid sequence of VHH(Anti-CLD18A2-hu6V3)-
      CD8 hinge-CD28a-CD28b- CD3?

<400> SEQUENCE: 137

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Phe Ser Ile Gly
            20                  25                  30

Val Met Gly Trp Tyr Arg Gln Ala Pro Gly Lys Gly Leu Glu Leu Val
        35                  40                  45

Ala Thr Ile Thr Ser Arg Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Asp Leu Ile Arg Pro Gly Asp Phe Tyr Gly Met Asp Tyr Trp Gly
            100                 105                 110

Gln Gly Thr Leu Val Thr Val Ser Ser Thr Thr Pro Ala Pro Arg
        115                 120                 125

Pro Pro Thr Pro Ala Pro Thr Ile Ala Ser Gln Pro Leu Ser Leu Arg
    130                 135                 140

Pro Glu Ala Cys Arg Pro Ala Ala Gly Gly Ala Val His Thr Arg Gly
145                 150                 155                 160

Leu Asp Phe Ala Cys Asp Phe Trp Val Leu Val Val Val Gly Gly Val
                165                 170                 175

Leu Ala Cys Tyr Ser Leu Leu Val Thr Val Ala Phe Ile Ile Phe Trp
            180                 185                 190

Val Arg Ser Lys Arg Ser Arg Leu Leu His Ser Asp Tyr Met Asn Met
        195                 200                 205
```

Thr Pro Arg Arg Pro Gly Pro Thr Arg Lys His Tyr Gln Pro Tyr Ala
            210                 215                 220

Pro Pro Arg Asp Phe Ala Ala Tyr Arg Ser Arg Val Lys Phe Ser Arg
225                 230                 235                 240

Ser Ala Asp Ala Pro Ala Tyr Gln Gln Gly Gln Asn Gln Leu Tyr Asn
                245                 250                 255

Glu Leu Asn Leu Gly Arg Arg Glu Glu Tyr Asp Val Leu Asp Lys Arg
            260                 265                 270

Arg Gly Arg Asp Pro Glu Met Gly Gly Lys Pro Gln Arg Arg Lys Asn
            275                 280                 285

Pro Gln Glu Gly Leu Tyr Asn Glu Leu Gln Lys Asp Lys Met Ala Glu
            290                 295                 300

Ala Tyr Ser Glu Ile Gly Met Lys Gly Glu Arg Arg Arg Gly Lys Gly
305                 310                 315                 320

His Asp Gly Leu Tyr Gln Gly Leu Ser Thr Ala Thr Lys Asp Thr Tyr
                325                 330                 335

Asp Ala Leu His Met Gln Ala Leu Pro Pro Arg
            340                 345

<210> SEQ ID NO 138
<211> LENGTH: 389
<212> TYPE: PRT
<213> ORGANISM: Artificial Sequence
<220> FEATURE:
<223> OTHER INFORMATION: Amino acid sequence of VHH(Anti-CLD18A2-hu6V3)-
      CD8 hinge-CD28a-CD28b-CD137-CD3?

<400> SEQUENCE: 138

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Phe Ser Ile Gly
            20                  25                  30

Val Met Gly Trp Tyr Arg Gln Ala Pro Gly Lys Gly Leu Glu Leu Val
        35                  40                  45

Ala Thr Ile Thr Ser Arg Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Asp Leu Ile Arg Pro Gly Asp Phe Tyr Gly Met Asp Tyr Trp Gly
            100                 105                 110

Gln Gly Thr Leu Val Thr Val Ser Ser Thr Thr Pro Ala Pro Arg
        115                 120                 125

Pro Pro Thr Pro Ala Pro Thr Ile Ala Ser Gln Pro Leu Ser Leu Arg
130                 135                 140

Pro Glu Ala Cys Arg Pro Ala Ala Gly Gly Ala Val His Thr Arg Gly
145                 150                 155                 160

Leu Asp Phe Ala Cys Asp Phe Trp Val Leu Val Val Val Gly Gly Val
                165                 170                 175

Leu Ala Cys Tyr Ser Leu Leu Val Thr Val Ala Phe Ile Ile Phe Trp
            180                 185                 190

Val Arg Ser Lys Arg Ser Arg Leu Leu His Ser Asp Tyr Met Asn Met
        195                 200                 205

Thr Pro Arg Arg Pro Gly Pro Thr Arg Lys His Tyr Gln Pro Tyr Ala
    210                 215                 220

Pro Pro Arg Asp Phe Ala Ala Tyr Arg Ser Lys Arg Gly Arg Lys Lys
225                 230                 235                 240

Leu Leu Tyr Ile Phe Lys Gln Pro Phe Met Arg Pro Val Gln Thr Thr
                245                 250                 255

Gln Glu Glu Asp Gly Cys Ser Cys Arg Phe Pro Glu Glu Glu Glu Gly
            260                 265                 270

Gly Cys Glu Leu Arg Val Lys Phe Ser Arg Ser Ala Asp Ala Pro Ala
        275                 280                 285

Tyr Gln Gln Gly Gln Asn Gln Leu Tyr Asn Glu Leu Asn Leu Gly Arg
290                 295                 300

Arg Glu Glu Tyr Asp Val Leu Asp Lys Arg Arg Gly Arg Asp Pro Glu
305                 310                 315                 320

Met Gly Gly Lys Pro Gln Arg Arg Lys Asn Pro Gln Glu Gly Leu Tyr
                325                 330                 335

Asn Glu Leu Gln Lys Asp Lys Met Ala Glu Ala Tyr Ser Glu Ile Gly
            340                 345                 350

Met Lys Gly Glu Arg Arg Arg Gly Lys Gly His Asp Gly Leu Tyr Gln
        355                 360                 365

Gly Leu Ser Thr Ala Thr Lys Asp Thr Tyr Asp Ala Leu His Met Gln
370                 375                 380

Ala Leu Pro Pro Arg
385

<210> SEQ ID NO 139
<211> LENGTH: 346
<212> TYPE: PRT
<213> ORGANISM: Artificial Sequence
<220> FEATURE:
<223> OTHER INFORMATION: Amino acid sequence of VHH(Anti-CLD18A2-
      hu19V3)-CD8 hinge-CD28a-CD28b- CD3?

<400> SEQUENCE: 139

Gln Val Gln Leu Val Glu Ser Gly Gly Gly Leu Val Gln Pro Gly Gly
1               5                   10                  15

Ser Leu Arg Leu Ser Cys Ala Ala Ser Gly Val Asp Ile Ser Ser Asp
            20                  25                  30

Val Met Ala Trp Tyr Arg Gln Ala Pro Gly Lys Gly Leu Glu Phe Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Leu Val Thr Val Ser Ser Thr Thr Pro Ala Pro Arg Pro
        115                 120                 125

Pro Thr Pro Ala Pro Thr Ile Ala Ser Gln Pro Leu Ser Leu Arg Pro
130                 135                 140

Glu Ala Cys Arg Pro Ala Ala Gly Gly Ala Val His Thr Arg Gly Leu
145                 150                 155                 160

Asp Phe Ala Cys Asp Phe Trp Val Leu Val Val Gly Gly Val Leu
                165                 170                 175

Ala Cys Tyr Ser Leu Leu Val Thr Val Ala Phe Ile Ile Phe Trp Val
            180                 185                 190

Arg Ser Lys Arg Ser Arg Leu Leu His Ser Asp Tyr Met Asn Met Thr
        195                 200                 205

Pro Arg Arg Pro Gly Pro Thr Arg Lys His Tyr Gln Pro Tyr Ala Pro
    210                 215                 220

Pro Arg Asp Phe Ala Ala Tyr Arg Ser Arg Val Lys Phe Ser Arg Ser
225                 230                 235                 240

Ala Asp Ala Pro Ala Tyr Gln Gln Gly Gln Asn Gln Leu Tyr Asn Glu
                245                 250                 255

Leu Asn Leu Gly Arg Arg Glu Glu Tyr Asp Val Leu Asp Lys Arg Arg
            260                 265                 270

Gly Arg Asp Pro Glu Met Gly Gly Lys Pro Gln Arg Arg Lys Asn Pro
        275                 280                 285

Gln Glu Gly Leu Tyr Asn Glu Leu Gln Lys Asp Lys Met Ala Glu Ala
    290                 295                 300

Tyr Ser Glu Ile Gly Met Lys Gly Glu Arg Arg Arg Gly Lys Gly His
305                 310                 315                 320

Asp Gly Leu Tyr Gln Gly Leu Ser Thr Ala Thr Lys Asp Thr Tyr Asp
                325                 330                 335

Ala Leu His Met Gln Ala Leu Pro Pro Arg
            340                 345

<210> SEQ ID NO 140
<211> LENGTH: 388
<212> TYPE: PRT
<213> ORGANISM: Artificial Sequence
<220> FEATURE:
<223> OTHER INFORMATION: Amino acid sequence of VHH(Anti-CLD18A2-
      hu19V3)-CD8 hinge-CD28a-CD28b-CD137-CD3?

<400> SEQUENCE: 140

Gln Val Gln Leu Val Glu Ser Gly Gly Gly Leu Val Gln Pro Gly Gly
1               5                   10                  15

Ser Leu Arg Leu Ser Cys Ala Ala Ser Gly Val Asp Ile Ser Ser Asp
            20                  25                  30

Val Met Ala Trp Tyr Arg Gln Ala Pro Gly Lys Gly Leu Glu Phe Val
        35                  40                  45

Ser Gly Leu Thr Arg Gly Gly Ser Ile Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Glu Ile Tyr Thr Gly Thr Phe Tyr Pro Arg Ser Tyr Trp Gly Gln
            100                 105                 110

Gly Thr Leu Val Thr Val Ser Ser Thr Thr Thr Pro Ala Pro Arg Pro
        115                 120                 125

Pro Thr Pro Ala Pro Thr Ile Ala Ser Gln Pro Leu Ser Leu Arg Pro
    130                 135                 140

Glu Ala Cys Arg Pro Ala Ala Gly Gly Ala Val His Thr Arg Gly Leu
145                 150                 155                 160

```
Asp Phe Ala Cys Asp Phe Trp Val Leu Val Val Gly Gly Val Leu
                165                 170                 175
Ala Cys Tyr Ser Leu Leu Val Thr Val Ala Phe Ile Ile Phe Trp Val
            180                 185                 190
Arg Ser Lys Arg Ser Arg Leu Leu His Ser Asp Tyr Met Asn Met Thr
        195                 200                 205
Pro Arg Arg Pro Gly Pro Thr Arg Lys His Tyr Gln Pro Tyr Ala Pro
    210                 215                 220
Pro Arg Asp Phe Ala Ala Tyr Arg Ser Lys Arg Gly Arg Lys Lys Leu
225                 230                 235                 240
Leu Tyr Ile Phe Lys Gln Pro Phe Met Arg Pro Val Gln Thr Thr Gln
                245                 250                 255
Glu Glu Asp Gly Cys Ser Cys Arg Phe Pro Glu Glu Glu Glu Gly Gly
            260                 265                 270
Cys Glu Leu Arg Val Lys Phe Ser Arg Ser Ala Asp Ala Pro Ala Tyr
        275                 280                 285
Gln Gln Gly Gln Asn Gln Leu Tyr Asn Glu Leu Asn Leu Gly Arg Arg
    290                 295                 300
Glu Glu Tyr Asp Val Leu Asp Lys Arg Arg Gly Arg Asp Pro Glu Met
305                 310                 315                 320
Gly Gly Lys Pro Gln Arg Arg Lys Asn Pro Gln Glu Gly Leu Tyr Asn
                325                 330                 335
Glu Leu Gln Lys Asp Lys Met Ala Glu Ala Tyr Ser Glu Ile Gly Met
            340                 345                 350
Lys Gly Glu Arg Arg Arg Gly Lys Gly His Asp Gly Leu Tyr Gln Gly
        355                 360                 365
Leu Ser Thr Ala Thr Lys Asp Thr Tyr Asp Ala Leu His Met Gln Ala
    370                 375                 380
Leu Pro Pro Arg
385
```

<210> SEQ ID NO 141
<211> LENGTH: 1617
<212> TYPE: DNA
<213> ORGANISM: Artificial Sequence
<220> FEATURE:
<223> OTHER INFORMATION: Sequence containing a CD8 signal peptide and a
      CD8 hinge-CD28a-CD28b-CD3-T2A-egfp structure

<400> SEQUENCE: 141

```
ggatccaggc taagcttac gcgtgccacc atggcttac agtgaccgc cttgctcctg      60 ccgctggcct tgctgctcca cgccgccagg ccgctgcagc atcatcatca tcatcatcat    120
atgaccacga cgccagcgcc gcgaccacca acaccggcgc ccaccatcgc gtcgcagccc    180
ctgtccctgc gcccagaggc gtgtcggcca gcggcggggg cgcagtgca cacgaggggg    240 ctggacttcg cctgtgattt ttgggtgctg gtggtggttg gtgagtcct ggcttgctat     300 agcttgctag taacagtggc ctttattatt ttctgggtga ggagtaagag gagcaggctc    360
ctgcacagtg actacatgaa catgactccc gccgccccg ggccaacccg caagcattac    420
cagccctatg cccccaccacg cgacttcgca gcctatcgct ccagagtgaa gttcagcagg    480
agcgcagacg cccccgcgta ccagcagggc agaaccagc tctataacga actcaatcta    540
ggacgaagag aggagtacga tgttttggac aagagacgtg gccgggaccc tgagatgggg    600
ggaaagccgc agagaaggaa gaaccctcag gaaggcctgt acaatgaact ccagaaagat    660
```

| | |
|---|---|
| aagatggcgg aggcctacag tgagattggg atgaaaggcg agcgcagaag gggcaagggg | 720 |
| cacgatggcc tttaccaggg tctcagtaca gccaccaagg acacctacga cgcccttcac | 780 |
| atgcaggccc tgcccctcg cggaagcgga gagggcagag gaagtctgct aacatgcggt | 840 |
| gacgtcgagg agaatcctgg acctatggtg agcaagggcg aggagctgtt caccggggtg | 900 |
| gtgcccatcc tggtcgagct ggacggcgac gtaaacggcc acaagttcag cgtgtccggc | 960 |
| gagggcgagg gcgatgccac ctacggcaag ctgaccctga agttcatctg caccaccggc | 1020 |
| aagctgcccg tgccctggcc caccctcgtg accaccctga cctacggcgt gcagtgcttc | 1080 |
| agccgctacc ccgaccacat gaagcagcac gacttcttca gtccgccat gcccgaaggc | 1140 |
| tacgtccagg agcgcaccat cttcttcaag gacgacggca actacaagac ccgcgccgag | 1200 |
| gtgaagttcg agggcgacac cctggtgaac cgcatcgagc tgaagggcat cgacttcaag | 1260 |
| gaggacggca acatcctggg gcacaagctg gagtacaact acaacagcca caacgtctat | 1320 |
| atcatggccg acaagcagaa gaacggcatc aaggtgaact tcaagatccg ccacaacatc | 1380 |
| gaggacggca gcgtgcagct cgccgaccac taccagcaga acacccccat cggcgacggc | 1440 |
| cccgtgctgc tgcccgacaa ccactacctg agcacccagt ccgccctgag caaagacccc | 1500 |
| aacgagaagc gcgatcacat ggtcctgctg gagttcgtga ccgccgccgg gatcactctc | 1560 |
| ggcatggacg agctgtacaa gtgataagtc gacctcgagg gaattccgat aatcaac | 1617 |

<210> SEQ ID NO 142
<211> LENGTH: 1743
<212> TYPE: DNA
<213> ORGANISM: Artificial Sequence
<220> FEATURE:
<223> OTHER INFORMATION: Sequence containing a CD8 signal peptide and a CD8 hinge-CD28a-CD28b-CD137-CD3-T2A-egfp

<400> SEQUENCE: 142

| | |
|---|---|
| ggatccaggc ctaagcttac gcgtgccacc atggccttac cagtgaccgc cttgctcctg | 60 |
| ccgctggcct tgctgctcca cgccgccagg ccgctgcagc atcatcatca tcatcatcat | 120 |
| atgaccacga cgccagcgcc gcgaccacca acaccggcgc ccaccatcgc gtcgcagccc | 180 |
| ctgtccctgc gcccagaggc gtgtcggcca gcggcggggg gcgcagtgca cacgagggg | 240 |
| ctggacttcg cctgtgattt ttgggtgctg gtggtggttg gtggagtcct ggcttgctat | 300 |
| agcttgctag taacagtggc ctttattatt ttctgggtga ggagtaagag gagcaggctc | 360 |
| ctgcacagtg actacatgaa catgactccc cgccgccccg gccaacccg caagcattac | 420 |
| cagccctatg ccccaccacg cgacttcgca gcctatcgct ccaaacgggg cagaaagaaa | 480 |
| ctcctgtata tattcaaaca accatttatg agaccagtac aaactactca agaggaagat | 540 |
| ggctgtagct gccgatttcc agaagaagaa gaaggaggat gtgaactgag agtgaagttc | 600 |
| agcaggagcg cagacgcccc cgcgtaccag cagggccaga accagctcta taacgaactc | 660 |
| aatctaggac gaagagagga gtacgatgtt ttggacaaga cgtggccg ggaccctgag | 720 |
| atgggggaa agccgcagag aaggaagaac cctcaggaag gcctgtacaa tgaactccag | 780 |
| aaagataaga tggcggaggc ctacagtgag attgggatga aggcgagcg cagaagggc | 840 |
| aaggggcacg atggccttta ccagggtctc agtacagcca ccaaggacac ctacgacgcc | 900 |
| cttcacatgc aggccctgcc cctcgcgga agcggagagg gcagaggaag tctgctaaca | 960 |
| tgcggtgacg tcgaggagaa tcctggacct atggtgagca agggcgagga gctgttcacc | 1020 |
| ggggtggtgc ccatcctggt cgagctggac ggcgacgtaa acggccacaa gttcagcgtg | 1080 |

```
tccggcgagg gcgagggcga tgccacctac ggcaagctga ccctgaagtt catctgcacc    1140
accggcaagc tgcccgtgcc ctggcccacc ctcgtgacca ccctgaccta cggcgtgcag    1200
tgcttcagcc gctaccccga ccacatgaag cagcacgact tcttcaagtc cgccatgccc    1260
gaaggctacg tccaggagcg caccatcttc ttcaaggacg acggcaacta caagacccgc    1320
gccgaggtga agttcgaggg cgacaccctg gtgaaccgca tcgagctgaa gggcatcgac    1380
ttcaaggagg acggcaacat cctggggcac aagctggagt acaactacaa cagccacaac    1440
gtctatatca tggccgacaa gcagaagaac ggcatcaagg tgaacttcaa gatccgccac    1500
aacatcgagg acggcagcgt gcagctcgcc gaccactacc agcagaacac ccccatcggc    1560
gacggccccg tgctgctgcc cgacaaccac tacctgagca cccagtccgc cctgagcaaa    1620
gaccccaacg agaagcgcga tcacatggtc ctgctggagt tcgtgaccgc cgccgggatc    1680
actctcggca tggacgagct gtacaagtga taagtcgacc tcgagggaat tccgataatc    1740
aac                                                                  1743

<210> SEQ ID NO 143
<211> LENGTH: 49
<212> TYPE: DNA
<213> ORGANISM: Artificial Sequence
<220> FEATURE:
<223> OTHER INFORMATION: Forward primer

<400> SEQUENCE: 143
cttgctgctc cacgccgcca ggccgcaggt gcagctcgtg gagtctggg                49

<210> SEQ ID NO 144
<211> LENGTH: 50
<212> TYPE: DNA
<213> ORGANISM: Artificial Sequence
<220> FEATURE:
<223> OTHER INFORMATION: Reverse primer

<400> SEQUENCE: 144
ggtcgcggcg ctggcgtcgt ggtagaagac acggtgacca gggtcccctg              50
```